US008440414B2

(12) United States Patent
Watanabe

(10) Patent No.: US 8,440,414 B2
(45) Date of Patent: May 14, 2013

(54) METHOD FOR MONITORING THE REGULATORY ACTIVITY OF CHROMOSOME SEGREGATION

(75) Inventor: Yoshinori Watanabe, Tokyo (JP)

(73) Assignee: Japan Science & Technology Agency, Kawaguchi-shi (JP)

( * ) Notice: Subject to any disclaimer, the term of this patent is extended or adjusted under 35 U.S.C. 154(b) by 5 days.

(21) Appl. No.: 13/150,312

(22) Filed: Jun. 1, 2011

(65) Prior Publication Data

US 2011/0250612 A1 Oct. 13, 2011

Related U.S. Application Data

(60) Continuation of application No. 12/427,159, filed on Apr. 21, 2009, now abandoned, which is a division of application No. 10/581,158, filed as application No. PCT/JP2004/017428 on Nov. 24, 2004, now Pat. No. 7,538,191.

(30) Foreign Application Priority Data

Dec. 1, 2003 (JP) ................................ 2003-401943
Sep. 27, 2004 (JP) ................................ 2004-279450

(51) Int. Cl.
*G01N 33/53* (2006.01)

(52) U.S. Cl.
USPC .......................................................... 435/7.1

(58) Field of Classification Search ........................ None
See application file for complete search history.

(56) References Cited

U.S. PATENT DOCUMENTS

2003/0108888 A1 6/2003 Scanlan et al.
2003/0233675 A1 12/2003 Cao et al.

FOREIGN PATENT DOCUMENTS

WO WO 01/88091 10/2001

OTHER PUBLICATIONS

Ouspenski et al., Experimental Cell Research (2003), 285: 175-188.*

Buonomo, S.B. et al., "Disjunction of Homologous Chromosomes in Meiosis I Depends on Proteolytic Cleavage of The Meiotic Cohesin Rec8 By Separin," *Cell*, vol. 103, No. 3, pp. 387-398, (2000).

Database EMBL [Online], "*Arabidopsis thaliana* cDNA Clone:RAFL14-23-C12, 3'-end." XP-002408320 retrived from EBI accession No. EM_PRO:AU226306, Database accession No. AU226306, abstract, Mar. 19, 2002.

Database EMBL [Online], "*Arabidopsis thaliana* T-DNA Flanking Sequence, Left Border, Clone 324A03" XP-002408319 retrieved from EBI accession No. EM_PRO:AJ551939, Database accession No. AJ551939, abstract, Mar. 29, 2003.

Database EMBL [Online], "*Homo sapiens* mRNA; cDNA DKFZp686P11149, (fron clone DKFZp686P11149)" XP-002408321 retrieved from EBI accession No. EM_PRO:BX647433, Database accession No. BX647433, abstract, Aug. 30, 2003.

Database EMBL [Online], "Human CGDD-50 Encoding DNA." XP-002408323 retrieved from EBI accession No. EM_PRO:ACC90627, Database accession No. ACC90627, abstract, Aug. 12, 2003.

Database EMBL [Online], "*Mus musculus* Shugoshin-like 2 (*S. pombe*), mRNA (cDNA Clone MGC:63378 Image:6833875), complete cds." XP-002408318 retrieved from EBI accession No. EM_PRO:BC052742, Database accession No. BC052742, abstract, May 21, 2003.

Database EMBL [Online], "*Neurospora crassa* DNA Linkage Group II BAC Contig B23G1" XP-002408317 retrieved from EBI accession No. EM_PRO:BX284754, Database accession No. BX284754, abstract, Mar. 6, 2003.

Database EMBL [Online], Novel centrimeric protein SHUGOSIN XP-002408314 retrived from EBI accession No. EM_PRO:DD173495, Database accession No. DD173495, abstract, Dec. 23, 2005.

Database EMBL [Online], "*S. cerevisiae* Choromosome XV Reading Frame ORF YORO73W" XP-002408316 retrieved from EBI accession No. EM_PRO:Z74981, Database accession No. Z74981, abstract, Jul. 9, 1996.

Database EMBL [Online], "*S. pombe* chromosome I cosmid c15A10." XP-002408315 retrieved from EBI accession No. EM_PRO:Z97208, Database accession No. Z97208, abstract, Jul. 1, 1997.

Database EMBL [Online], "*Schizosaccharomyces pombe* cosmid 855, complete sequence." XP-002408313 retrieved from EBI accession No. EM_PRO:U23749 Database accession No. U23729, abstract, Apr. 21, 1995.

Database EMBL [Online], "UI-M-HJO-cmu-p-13-0-UI. rl NIH_ BMAP_HJO *Mus musculus* cDNA Clone Image:30633108 5', mRNA Sequence." XP-002408322 retrieved from EBI accession No. EM_PRO:CF950315, Database accession No. CF950315, abstract, Nov. 21, 2003.

Kitajima, T.S. et al., "Rec8 Cleavage by Separase Is Required For Meiotic Nuclear Divisions In Fission Yeast," *EMBO J.*, vol. 22, No. 20, pp. 5643-5653 (2003).

(Continued)

*Primary Examiner* — Ilia Ouspenski
(74) *Attorney, Agent, or Firm* — Locke Lord LLP

(57) ABSTRACT

The present invention is to provide meiosis-specific novel kinetochore protein Sgo1 (shugoshin) derived from fission yeast *Schizosaccharomyces pombe*, and a homologue or paralogue thereof having a regulatory activity of chromosome segregation; and DNAs encoding them; as a factor ensuring the retention of unidirection and cohesion in sister centromere at meiosis I in cooperation with cohesin. To elucidate the proteins protecting Rec8 during anaphase, the present inventor screened in fission yeast genes for a gene that inhibits mitotic growth and prevents sister chromatid from the separation at anaphase, when co-expressed with Rec8. In this approach, meiosis-specific protein Sgo1 that protects (Shugo) centromeric Rec8 from the degradation at anaphase I was indentified. Further, a budding yeast Sgo1 homologue and a fission yeast mitotic paralogue Sgo2 were identified.

1 Claim, 13 Drawing Sheets

OTHER PUBLICATIONS

Kitajima, T.S. et al., "The Conserved Kinetochore Protein Shugoshin Protects Centromeric Cohesion During Meiosis," *Nature,* vol. 427, pp. 510-517, Feb. 5, 2004.

Kitajima, T.S. et al., "The Conserved Kinetochore Protein Shugoshin Protects Centromeric Cohesion During Meiosis (Horizon sareta Dogentai Tanpakushitsu Shugoshin Wa Wensu Bunresu Ni Oite Shimai Dogentaikan No Sechaku O Hogosuru)," Experimental Medicine (Jikken Igaku), vol. 22, No. 7, pp. 959-961, (May 2004), with English translation.

Watanabe et al. "Shugoshin: Guardian Spirit at the Centromere," *Current Opinion in Cell Biology, Current Science,* London, GB, vol. 17, No. 6, pp. 590-595, XP005136506 ISSN: 0955-0674, Dec. 2005

Wood, V. et al., "The Genome Sequence of *Schizosaccharomyces pombe,*" *Nature,* vol. 415, pp. 871-880 (Feb. 21, 2002).

Database GenBank [online], *"Schizosaccharomyces pombe* chromosome II, complete sequence;" NCBI Accession No. NC_003423; Mar. 5, 2002 referenced to Wood, V. et al., "The Genome Sequence of *Schizosaccharomyces Pombe,*" *Nature,* vol. 415, pp. 871-880 (Feb. 21, 2002; already cited on Apr. 21, 2009).

Database GenBank [online], "hypothetical protein [*Schizosaccharomyces pombe*];" NCBI Accession No. NP_595378; Mar. 5, 2002 referenced to Wood, V. et al., "The Genome Sequence of *Schizosaccharomyces pombe,*" *Nature,* vol. 415, pp. 871-880 (Feb. 21, 2002; already cited on Apr. 21, 2009).

Tang et al., "Maintenance of sister-chromatid cohesion at the centromere by the *Drosophila* MEI-S332 protein", Genes Dev. 1998, 12: 3843-3856.

Shonn et al., "Spo13 protects meiotic cohesin at centromeres in meiosis 1", Genes Dev, 2002, 16: 1659-1671.

Canadian Office Action for corresponding Application 2,547,655, dated Jun. 1, 2011.

Sigma Catalog, 1993, Product No. G5149, p. 1089 (cited in U.S. Appl. No. 12/427,205).

* cited by examiner

METHOD FOR MONITORING THE REGULATORY ACTIVITY OF CHROMOSOME SEGREGATION

This application is a continuation application of U.S. patent application Ser. No. 12/427,159 filed Apr. 21, 2009, which is a divisional application of U.S. patent application Ser. No. 10/581,158 filed Jan. 30, 2007 and issued as U.S. Pat. No. 7,538,191 B2 on May 26, 2009, which is national phase entry of International Application No. PCT/JP2004/017428 filed on Nov. 24, 2004, which claims priority benefit of Japanese Application No. JP 2003-401943 filed Dec. 1, 2003 and Japanese Application No. JP 2004-279450 filed Sep. 27, 2004, the contents of each of which are incorporated in their entireties.

TECHNICAL FIELD

The present invention relates to a protector protein Sgo1 (shugoshin) of cohesin Rec8 derived from fission yeast *Schizosaccharomyces pombe*, its homologue and paralogue having a regulatory activity of chromosome segregation, and DNAs encoding them.

BACKGROUND OF THE INVENTION

In eukaryotes, sister chromatid cohesion is established during S phase of cell cycle and, maintained throughout G2 until M phase. During mitosis, this cohesion is destroyed along the entire length of chromosome, allowing sister chromatid to segregate to the opposite sides of cell (equational division) and ensuring that each daughter cell receives one copy of each chromosome. In contrast, meiosis consists of two rounds of chromosome segregation following a single round of DNA replication, leading to the formation of four haploid gametes from one diploid germ cell. During meiosis I, homologous chromosomes (homologues) pair to recombine, forming chiasmata in which one sister chromatid from one homologue is covalently attached to a sister chromatid from the other homologue. Hence, in order for homologues to segregate at meiosis I, cohesion of sister chromatid is necessary to be dissociated along the chromosome arms to resolve chiasmata. However, sister chromatid cohesion is retained at centromere until meiosis II, and utilizes the residual centromeric cohesion when sister chromatid segregates, in the same manner as it does in mitosis. Thus, meiotic division requires sister chromatid cohesion to be dissociated in two steps. However, the molecular mechanism for protection of centromeric cohesion only during meiosis I and only at the centromere has remained to be elucidated (e.g., see *Annu Rev Genet* 35, 673-745 (2001)).

There are important clues as to the molecular nature of sister chromatid cohesion, and the mechanism dissociating sister chromatid cohesion at the onset of anaphase (e.g., see *Annu Rev Genet* 35, 673-745(2001); *Curr Opin Cell Biol* 12, 297-301(2000); *Curr Biol* 13, R104-14 (2003); *Annu Rev Cell Dev Biol* 17, 753-77(2001); *Genes Dev* 16, 399-414 (2002>>. In various eukaryotes, sister chromatid cohesion depends on a multisubunit cohesin complex including Scc1 (Rad21 in fission yeast *Schizosaccharomyces pombe*). Anaphase promoting complex (APC)-dependent degradation of the securin, Cut2/Pds1, allows to dissociate the Cut1/Esp1 endopeptidase (separase), which in turn cleaves Rad21/Scc1, dissociating sister chromatid cohesion. During meiosis, the cohesion subunit Rad21/Scc1 is replaced with a meiotic counterpart, Rec8 (e.g., see *Cell* 98, 91-103(1999); *Mol. Cell. Biol.* 19, 3515-3528(1999); *Nature* 400, 461-4(1999); *Genes Dev* 15, 1349-60(2001); *J Cell Biol* 160, 657-70(2003)). As Rec8 complex resides only at centromere after meiosis I and the depletion of Rec8 destroys centromeric cohesion, the presence of Rec8 at centromere has been thought to confer the persistence of cohesion throughout meiosis I (e.g., see *Nat Cell Biol* 1, E125-7 (1999)). Several lines of evidence suggest that Rec8 along chromosome arms is cleaved by separase at anaphase I while centromeric Rec8 is specifically protected until metaphase II (e.g., see *Cell* 103, 387-98(2000); *Embo J* 22, 5643-53(2003)). Budding yeast SP013 has been implicated in the protection of centromeric Rec8 (e.g., see *Genes Dev* 16, 1659-71(2002); *Genes Dev* 16, 1672-81(2002)), but SP013 is not centromeric and may function indirectly. *Drosophila* MEI-S332 is a protein residing at centromere, is required for the persistence of centromeric cohesion during meiosis I, and has features of a candidate protector of meiotic centromeric cohesion, although the details of such protection have so far not been elucidated (e.g., see *Annu Rev Cell Dev Biol* 17, 753-77(2001); *Cell* 83, 247-256(1995)). Despite the completion of genome sequencing projects on several organisms, no homologue of these proteins has emerged, preventing the formulation of a generalized view of the protection. Concurrently, studies in fission yeast have illuminated the importance of pericentromeric heterochromatin for recruiting centromeric Rec8 complexes and ensuring centromeric cohesion during meiosis I (e.g., see *Science* 300, 1152-5 (2003)). However, pericentromeric heterochromatin cannot alone confer the specific protection of Rec8 at meiosis I toward meiosis II.

DISCLOSURE OF THE INVENTION

Almost all the eukaryotes including human propagate offsprings by sexual reproduction evolutionarily predominant with a mixture of genome. Meiosis that reduces chromosome number in half is a core part of the sexual reproduction mechanism. In somatic mitosis, two kinetochores of sister chromatid are caught by spindle microtuble extended from the opposite poles, and sister chromatid is evenly segregated to the both poles by concurrently dissolving the cohesion of arms and centromeres (equational division). In contrast, in meiosis I kinetochores of sister chromatids are caught by spindle microtuble extended from the same pole, and segregated to the same pole while retaining the cohesion at centromere (meiotic division). Next, for the first time in meiosis II the cohesion of centromere site of sister chromatid is dissolved, and separated toward one pole or the other of the two poles respectively, which culminates in the generation of accurate four haploid gametes. Meiosis-specific meiotic division is a modality of chromosome segregation conserved in almost all the eukaryotes, from yeast to human, however regulatory mechanism at the molecular level has remained enigmatic for a long time. The present inventor has demonstrated that meiosis-specific chromosome cohesion factor, cohesin plays an essential role in this regulation by using fission yeast (*Nature* 400, 461-4(1999); *Science* 300, 1152-5 (2003); *Nature* 409, 359-363 (2001)). An object of the present invention is to provide meiosis-specific novel kinetochore protein Sgo1 (shugoshin) derived from fission yeast *Schizosaccharomyces pombe*, and a homologue or paralogue thereof having a regulatory activity of chromosome segregation; and DNAs encoding them; as a factor ensuring the retention of unidirection and cohesion in sister centromere at meiosis I in cooperation with cohesin.

Meiosis comprises two steps of specialized nuclear divisions for producing haploid gametes. To accomplish this, sister chromatid cohesion is necessary to be dissociated in a stepwise manner, first from chromosome arms at anaphase I and second from centromeres at anaphase II. In particular, the factors that protect centromeric cohesion during meiosis I have heretofore remained undissolved. To elucidate the proteins protecting Rec8 during anaphase, the present inventor screened in fission yeast genes for a gene that inhibits mitotic growth and prevents sister chromatid from the separation at anaphase, when co-expressed with Rec8. In this approach, meiosis-specific protein that is a protector of Rec8 in fission yeast and protects (Shugo) centromeric Rec8 from the degradation at anaphase I was indentified, and named Sgo1 (Shugoshin, a Japanese for "guardian spirit"). It was also identified that shugoshin plays an important role in mitotic chromosome segregation, and then identified a budding yeast Sg01 homologue and a fission yeast mitotic paralogue Sgo2. A marginal similarity between Sgo1 and *Drosophila* MEI-S332 was identified, and Sgo1 homologue in other eukaryotes was also identified. Shugoshin-like proteins in animal cells, which were predicted from the sequence, also have functional conservation with yeast shugoshin. The present invention has been thus completed based on this knowledge.

That is, the present invention relates to (1) a DNA encoding a following protein (a) or (b): (a) a protein consisting of an amino acid sequence shown in SEQ ID NO: 2, (b) a protein comprising an amino acid sequence where one or several amino acids are deleted, replaced or added in an amino acid sequence shown in SEQ ID NO: 2, and having a regulatory activity of chromosome segregation; (2) a DNA consisting of a base sequence shown in SEQ ID NO: 1 or a complementary sequence thereof; (3) a DNA containing part or whole of a base sequence shown in SEQ ID NO: 1 or a complementary sequence thereof, and encoding a protein that has a regulatory activity of chromosome segregation; (4) a DNA hybridizing with the DNA according to "2" under stringent conditions and encoding a protein that has a regulatory activity of chromosome segregation; (5) a protein consisting of an amino acid sequence shown in SEQ ID NO: 2; and (6) a protein consisting of an amino acid sequence where one or several amino acids are deleted, replaced or added in an amino acid sequence shown in SEQ ID NO: 2, and having a regulatory activity of chromosome segregation.

The present invention also relates to (7) a DNA encoding a following protein (a) or (b): (a) a protein consisting of an amino acid sequence shown in SEQ ID NO: 4, (b) a protein consisting of an amino acid sequence where one or several amino acids are deleted, replaced or added in an amino acid sequence shown in SEQ ID NO: 4, and having a regulatory activity of chromosome segregation; (8) a DNA consisting of a base sequence shown in SEQ ID NO: 3 or a complementary sequence thereof; (9) a DNA containing part or whole of a base sequence shown in SEQ ID NO: 3 or a complementary sequence thereof, and encoding a protein that has a regulatory activity of chromosome segregation; (10) a DNA hybridizing with the DNA according to "8" under stringent conditions and encoding a protein that has a regulatory activity of chromosome segregation; (11) a protein consisting of an amino acid sequence shown in SEQ ID NO: 4; and (12) a protein consisting of an amino acid sequence where one or several amino acids are deleted, replaced or added in an amino acid sequence shown in SEQ 10 NO: 4, and having a regulatory activity of chromosome segregation.

The present invention further relates to (13) a DNA encoding a following protein (a) or (b): (a) a protein consisting of an amino acid sequence shown in SEQ ID NO: 6, (b) a protein consisting of an amino acid sequence where one or several amino acids are deleted, replaced or added in an amino acid sequence shown in SEQ ID NO: 6, and having a regulatory activity of chromosome segregation; (14) a DNA consisting of a base sequence shown in SEQ ID NO: 5 or a complementary sequence thereof; (15) a DNA containing part or whole of a base sequence shown in SEQ ID NO: 5 or a complementary sequence thereof, and encoding a protein that has a regulatory activity of chromosome segregation; (16) a DNA hybridizing with the DNA according to "14" under stringent conditions and encoding a protein that has a regulatory activity of chromosome segregation; (17) a protein consisting of an amino acid sequence shown in SEQ ID NO: 6; and (18) a protein consisting of an amino acid sequence where one or several amino acids are deleted, replaced or added in an amino acid sequence shown in SEQ ID NO: 6, and having a regulatory activity of chromosome segregation.

The present invention still further relates to (19) a DNA encoding a following protein (a) or (b) that has a regulatory activity of chromosome segregation: (a) a protein consisting of an amino acid sequence shown in SEQ ID NO: 8, 10, 12, 14, 16, 18 or 20, (b) a protein consisting of an amino acid sequence where one or several amino acids are deleted, replaced or added in an amino acid sequence shown in SEQ ID NO: 8, 10, 12, 14, 16, 18 or 20; (20) a DNA consisting of a base sequence shown in SEQ ID NO: 7, 9, 11, 13, 15, 17 or 19 or a complementary sequence thereof, and encoding a protein that has a regulatory activity of chromosome segregation; (21) a DNA containing part or whole of a base sequence shown in SEQ ID NO: 7, 9, 11, 13, 15, 17 or 19 or a complementary sequence thereof, and encoding a protein that has a regulatory activity of chromosome segregation; (22) a DNA hybridizing with the DNA according to "7", "9", "11", "13", "15", "17" or "19" under stringent conditions and encoding a protein that has a regulatory activity of chromosome segregation; (23) a protein consisting of an amino acid sequence shown in SEQ ID NO: 8, 10, 12, 14, 16, 18 or 20, and having a regulatory activity of chromosome segregation; and (24) a protein consisting of an amino acid sequence where one or several amino acids are deleted, replaced or added in an amino acid sequence shown in SEQ ID NO: 8, 10, 12, 14, 16, 18 or 20, and having a regulatory activity of chromosome segregation.

Furthermore, the present invention relates to (25) a fusion protein in which the protein according to "5", "6", "11", "12", "23" or "24" is bound with a marker protein and/or a peptide tag; (26) an antibody specifically binding to the protein according to "5", "6", "11", "12", "23" or "24"; and (27) the antibody according to "26", which is a monoclonal antibody.

Figure 9:
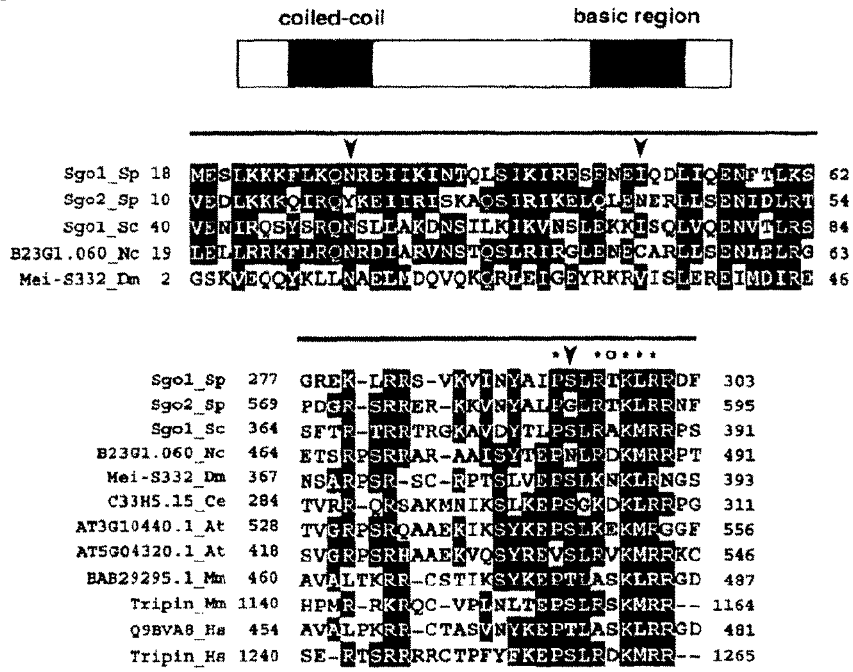
FIG. 9 is a set of pictures showing sequences of the amino terminal coiled-coil regions and carboxyl terminal basic regions of shugoshin-like proteins in various organisms. The primary sequences of the amino terminal regions of Sgo1 are conserved in *Schizosaccharomyces pombe* (Sgo1 and Sgo2), budding yeast (ScSgo1) and *Neurospora crassa* (B23G1.060), while the sequences containing ME1-S332 in other species are not conserved, all presumably carry coiled-coil motif (predicted by COILS program (*Science* 252, 1162-

4(1991))). See the arrowheads, asterisks and circles in the pictures. The sequences in FIG. 9 respectively correspond to the following SEQ ID NOs: Sg01_Sp18: SEQ ID NO: 21; Sg02_Sp10: SEQ ID NO: 22; Sg01_Sc40: SEQ ID NO:23; B23GI.060_Nc19: SEQ ID NO: 24; Mei-S332_Dm2: SEQ ID NO: 25; Sg01_Sp277: SEQ ID NO: 26; Sg01_Sp569: SEQ ID NO: 27; Sg01_Sc364: SEQ ID NO: 28; B23GI.060_Nc464: SEQ ID NO: 29; Mei-S332_Dm367: SEQ ID NO: 30; C33H5.15_Ce: SEQ ID NO: 31; AT3G10440.1_At: SEQ ID NO: 32; AT5G04320.1_At: SEQ ID NO: 33; BAB29295.1_Mm: SEQ ID NO: 34; Tripin_Mm: SEQ ID NO:35; Q9BVA8_Hs: SEQ ID NO: 36; Tripin_Hs: SEQ ID NO: 37.

Figure 10:
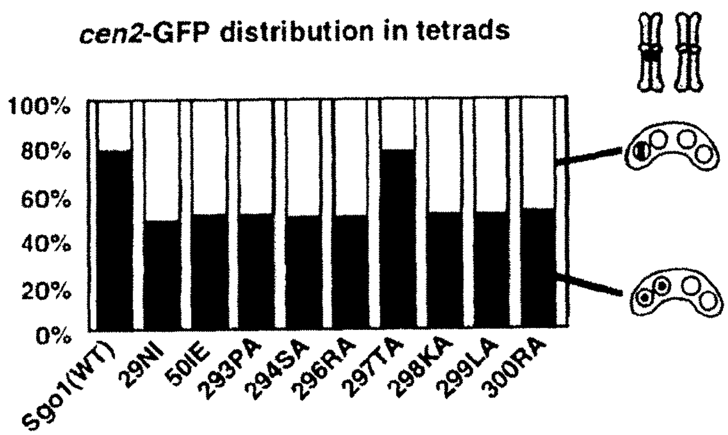

FIG. 10 is a picture showing the results of examination of sgo1 mutations that were generated within conserved regions. Both h+sgo1Δ and h−sgo1Δcen2-GFP cells transformed with the indicated plasmid, were mixed on SPA plates and monitored for segregation of cen2-GFP at meiosis II. A plasmid pREP81 bearing a weak version of the thiamine-repressible nmt1 promoter was used to express sgo1. Control cells carrying plasmid pREP81-sgo1 (wt) showed nearly 80% the segregation at meiosis II, whereas cells expressing non-segregation sgo1 allele showed random segregation (50% segregation). Any of the mutations tested, except a non-conserved site mutation 297TA, did not complement sgo1Δ in this assay. The means of two independent experiments are shown (n>100).

Figure 11:
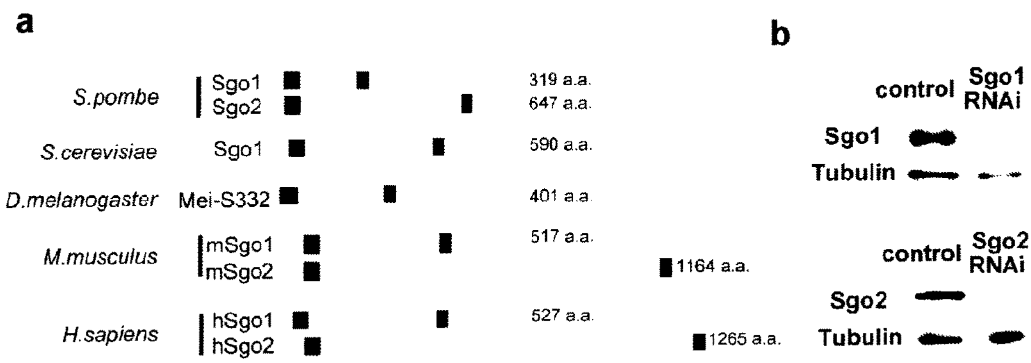

FIG. 11(*a*) is a picture showing schematic representation of the shugoshin family proteins. A predicted coiled-coil (red) and a conserved basic region (blue) exist in the N-terminal and C-terminal regions respectively. Further, FIG. 11(*b*) is a picture showing the result of analysis in HeLa cell extracts by western blotting after transfection with siRNA.

Figure 12:
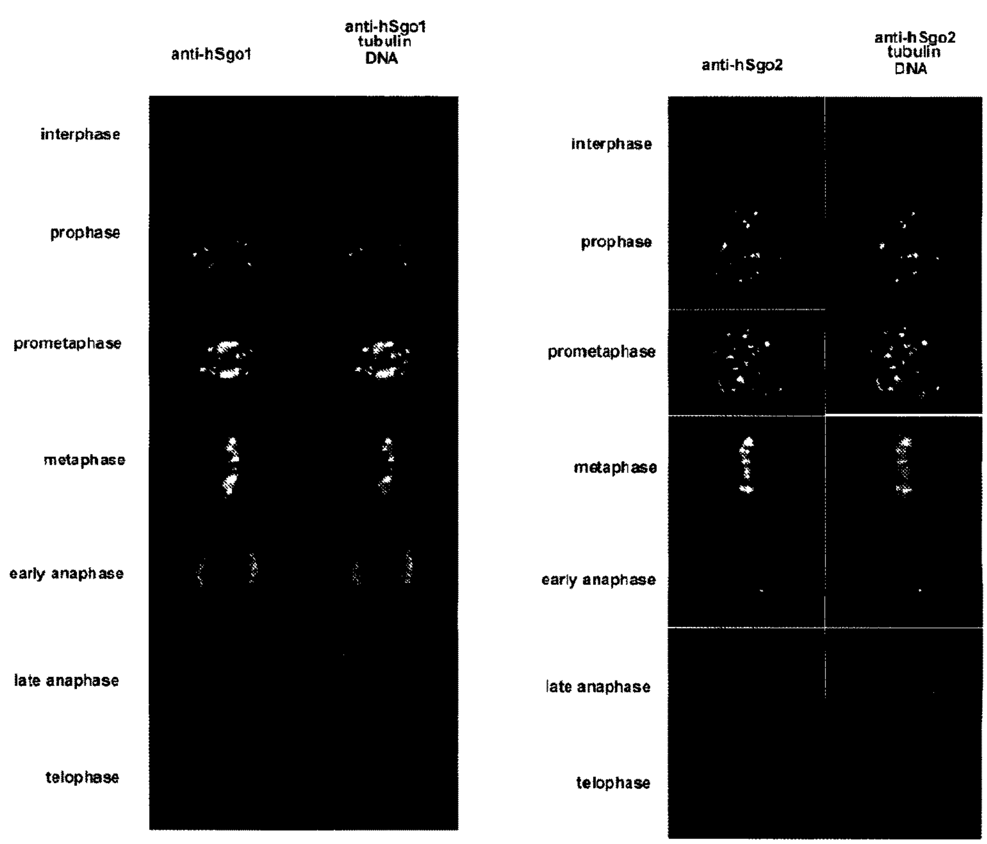

FIG. 12 is a set of pictures showing the results that HeLa cells were stained (green) with antibody against hSgo1 or hSgo2 prepared from rabbit, concurrently stained with tubulin antibody and DAPI, and then respectively co-stained with spindle (red) and chromosome DNA (blue). Meanwhile, the cells were fixed with paraformaldehyde.

Figure 13:
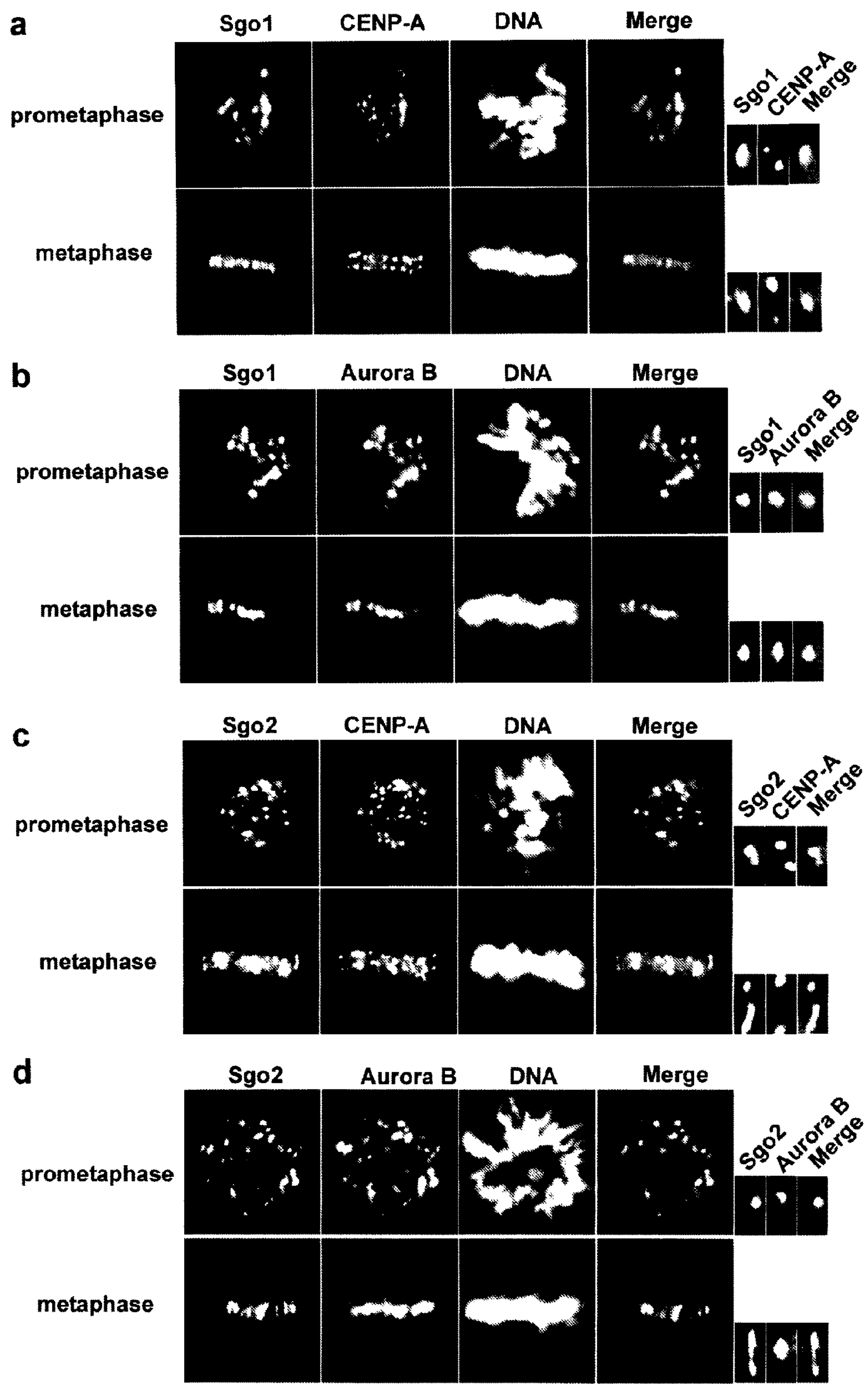

FIG. 13 is a set of pictures showing the results that HeLa cells at prometaphase and metaphase were stained with antibodies against hsgo1 or hSgo2 (green), and concurrently co-stained with antibodies against centromere protein CENP-A (a, c; red), antibodies against passenger protein Aurora B of chromosome localized within kinetochore from prophase to metaphase (b, d; red), and DAPI (blue). Both signals of hSgo1 and hSgo2 showed signals at the sites close to CENP-A dots on chromosome. From the above, it was revealed that both hsgo1 and hSgo2 are centromere proteins. Furthermore, both sites of Sgo1 and Aurora B were practically the same at prometaphase and metaphase, whereas Sgo2 was placed just outside Aurora B. From the above, it was revealed that both hsgo1 and hSgo2 are placed within kinetochore from prometaphase to metaphase.

Figure 14:
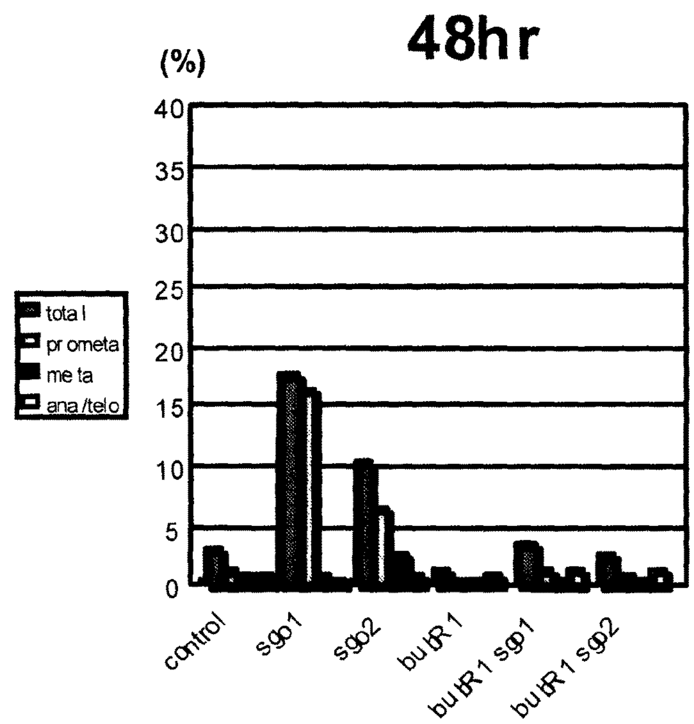

FIG. 14 is a picture showing the results of RNAi experiments that targeted hsgo1 and hSgo2 respectively. The expressions in any proteins were significantly suppressed after 48 hours, thereby the cells arrested in mitosis (total in the figure) were accumulated. As the accumulation was dissolved by suppressing a spindle checkpoint factor BubR1 by RNAi, it was suggested that hSgo1 and hSgo2 directly or indirectly function during the process where spindle take kinetochore properly at centromeres.

Figure 15:
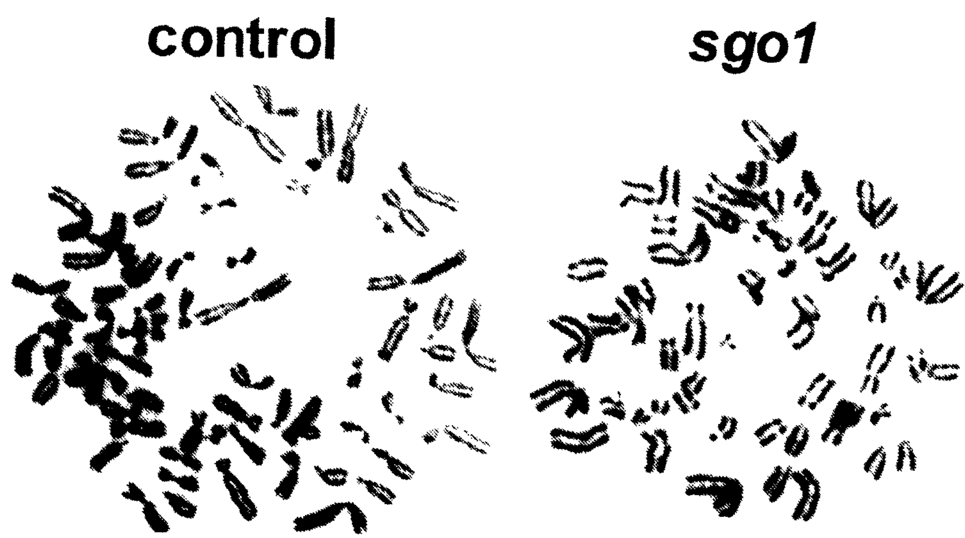

FIG. 15 is a set of pictures showing the results, where RNAi experiments targeting hsgo1 was performed by using HeLa cells, and then the cells were mounted on a slide glass and stained with Giemsa. It was revealed that sister chromatid strongly adhered at centromere site in control cells; but in cells suppressed hsgo1, the adhesion at centromere site was weak, and easily detached by the experiment operation.

Figure 16:
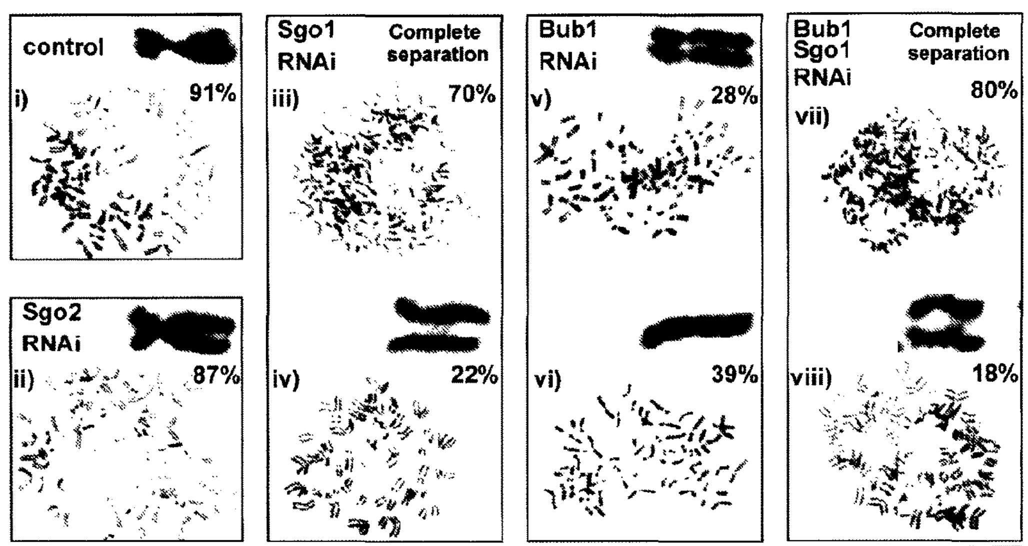
Figure 16:
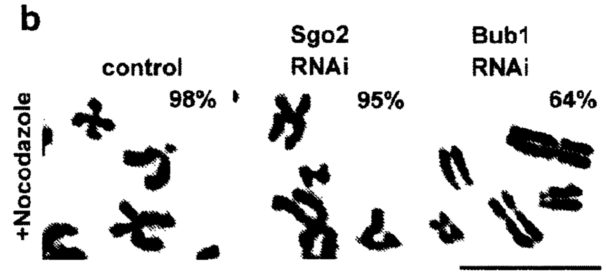
Figure 16:
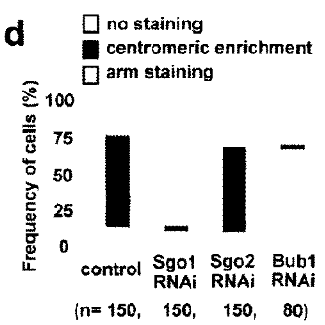
Figure 16:
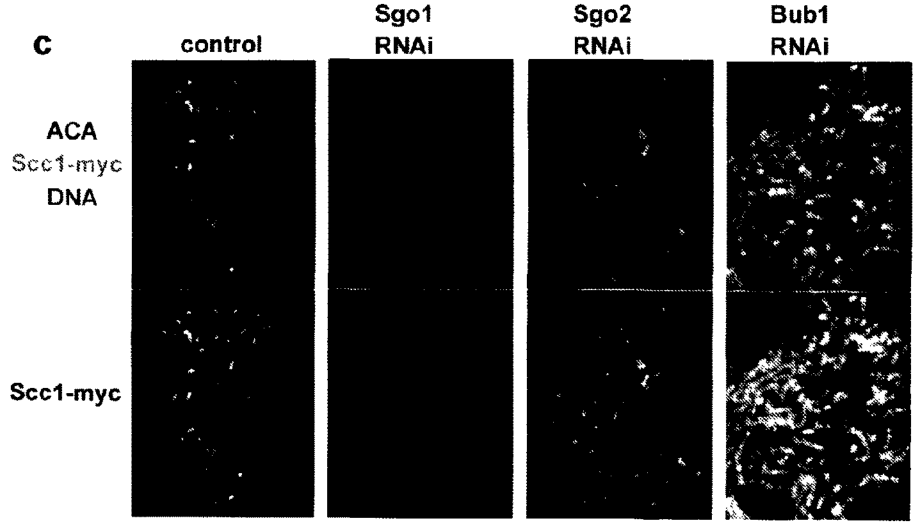

FIG. 16 is a set of pictures showing that Sgo1 and Bub1 are required for condensation at centromeres in mitosis. (a) By treatments with siRNA, chromosome spread was performed in mitotic HeLa cells stained with Giemsa. Representative spread is shown together with the occurrence rates. More than one hundred of the prophases and prometaphases were observed for each RNAi. An example of sister chromatid pair is magnified at the top. (b) After treatment with nocodazole for 4 hours, chromosome spread was observed in cells interfered with RNAi. Examples of the spread are shown with the frequency (n>100). (c) HeLa cells expressing Scc1-myc were fixed at 36 hours after the treatment with siRNAs. The cells were immunostained with anti-myc-antibody (green) and anti-centromere-antibody (ACA) (red). DNA was stained with DAPI (blue). (d) Rates of the cells showing Scc1-myc staining are shown. Cells expressing Scc1-myc in this cell line were less than 25%. Scale bar shows 10 μm.

Figure 17:
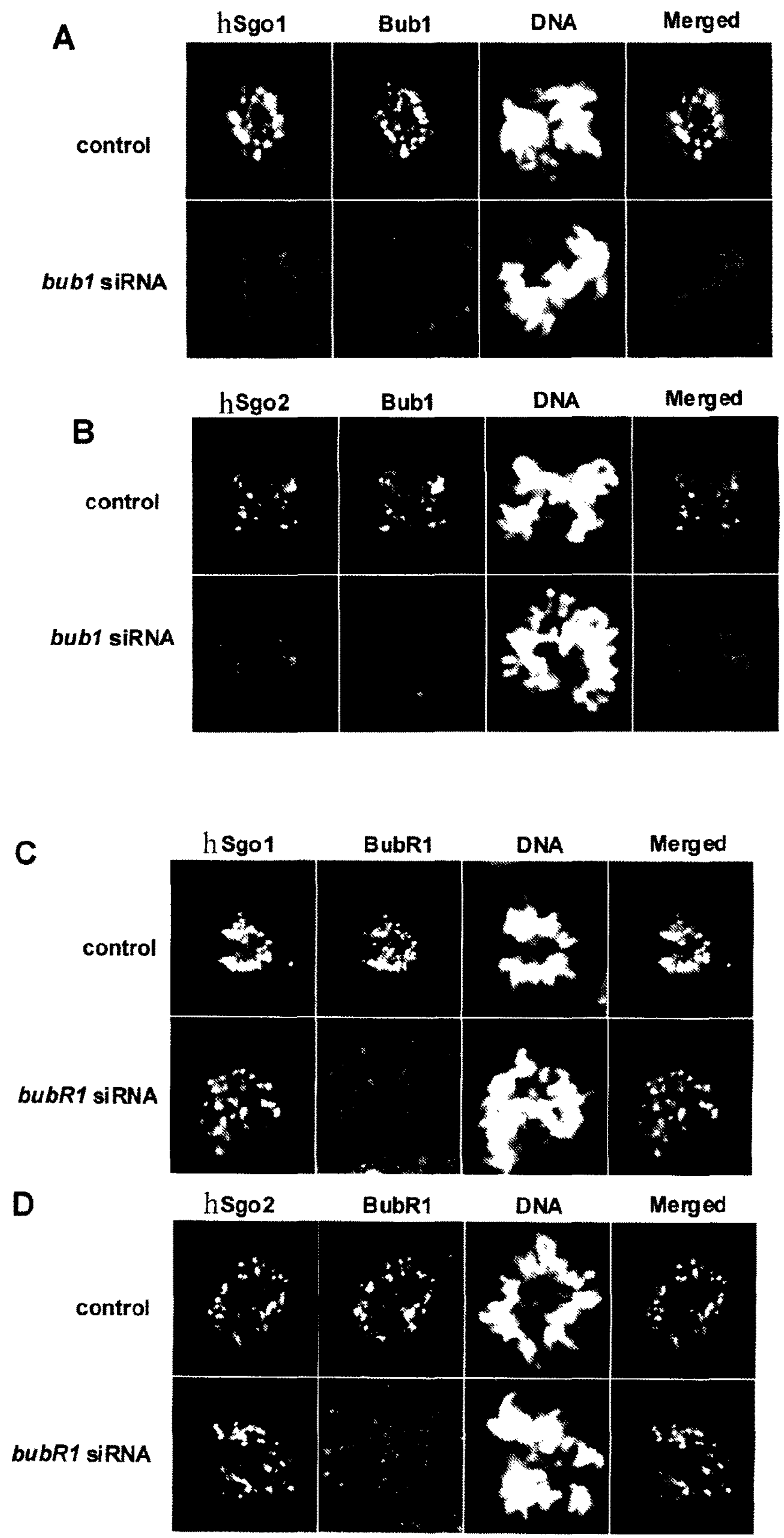

FIG. 17 is a set of pictures showing the results of RNAi experiments targeting Bub1, respectively. (A, B) RNAi experiments targeting Bub1 were performed respectively, and resulted in disappearance of the localization of both proteins, hSgo1 and hSgo2 at centromere. (C, D) As the localization of both proteins, hSgo1 and hSgo2 at centromere was normal in RNAi experiments targeting a control, BubR1; the significance of the results of Bub1 was ensured. It is shown that Bub1 and BubR1 are similar but different proteins, and the localization of hSgo1 and hSgo2 at centromere depends on Bub1 (A, B), but not on BubR1 (C, D).

Figure 18:
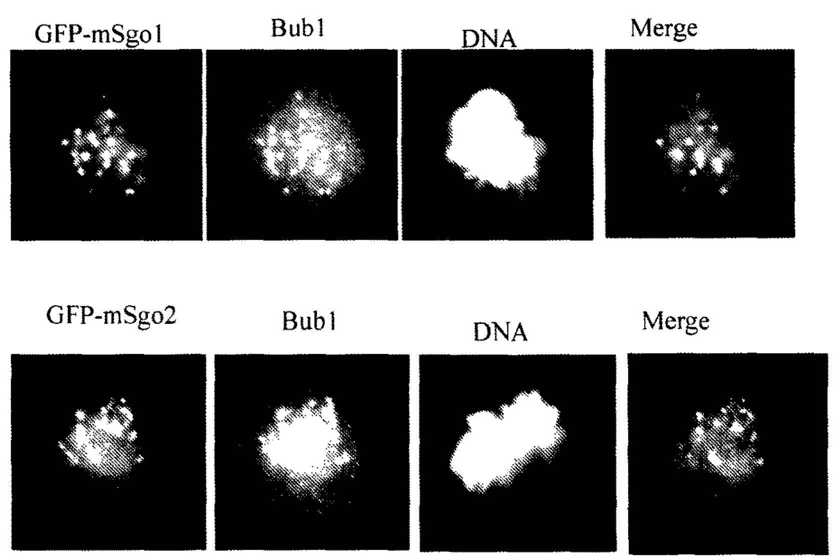

FIG. 18 is a set of pictures showing the results that a clone in which cDNA of mouse shugoshin homologous gene (SEQ ID NOs: 21 and 23) is fused with GFP gene was generated by using retroviral vector, and expressed in human HeLa cells. It was revealed that any of the GFP fusion proteins is co-localized with human kinetochore protein Bub1 in mitosis. The appended drawings of the figures are presented to further describe the invention and to assist in its understanding through clarification of its various aspects.

BEST MODE OF CARRYING OUT THE INVENTION

As for a protein of the present invention, a protein Sgo1 (shugoshin) comprising an amino acid sequence shown in SEQ ID NO: 2 and having a regulatory activity of chromosome segregation; a protein comprising the amino acid sequence shown in SEQ ID NO: 2 where one or several amino acids are deleted, replaced or added, and having a regulatory activity of chromosome segregation; a paralogue Sgo2 of protein Sgo1 comprising an amino acid sequence shown in SEQ ID NO: 4 and having a regulatory activity of chromosome segregation; a protein comprising the amino acid sequence shown in SEQ ID NO: 4 where one or several amino acids are deleted, replaced or added, and having a regulatory activity of chromosome segregation; a *Saccharomyces cerevisiae* homologue ScSgo1 of protein Sgo1 comprising an amino acid sequence shown in SEQ ID NO: 6 and having a regulatory activity of chromosome segregation; a protein comprising the amino acid sequence shown in SEQ ID NO: 6 where one or several amino acids are deleted, replaced or added, and having a regulatory activity of chromosome segregation; a protein (NC) comprising an amino acid sequence shown in SEQ ID NO: 8 and having a *Neurospora crassa*-derived regulatory activity of chromosome segregation; a protein comprising the amino acid sequence shown in SEQ ID NO: 8 where one or several amino acids are deleted, replaced or added, and having a regulatory activity of chromosome segregation; a protein (At) comprising an amino acid sequence shown in SEQ ID NO: 10 or 12 and having a *Arabidopsis*-derived regulatory activity of chromosome segregation; a protein comprising the amino acid sequence shown in SEQ ID NO: 10 or 12 where one or several amino acids are deleted, replaced or added, and having a regulatory activity of chromosome segregation; a protein (Mm) comprising an amino acid sequence shown in SEQ ID NO: 14 or 16 and having a mouse-derived regulatory activity of chromosome segregation; a protein comprising the amino acid sequence shown in SEQ ID NO: 14 or 16 where one or several amino acids are deleted, replaced or added, and having a regulatory activity of chromosome segregation; a protein (Hs) comprising an amino acid sequence shown in SEQ ID NO: 18 or 20 and having a human-derived regulatory activity of chromosome segregation; and a protein comprising the amino acid sequence shown in SEQ ID NO: 18 or 20 where one or several amino acids are deleted, replaced or added, and having a regulatory activity of chromosome segregation; can be exemplified. Further, as for the regulatory activity of chromosome segregation described in the above, although it is not especially limited as long as the activities regulate chromosome segregation, for example, activities correctly regulating chromosome segregation of germ cells and/or of somatic cell division are preferable, and activities protecting (Shugo) the centromere of sister chromatid from the separation in meiosis I is more preferable. In addition, proteins of the present invention can be prepared by known methods based on DNA-sequence information and the like, and the derivations are not limited to yeast, mouse, human and the like. Furthermore, for example, Sgo1 (shugoshin) mutant that is a protein comprising an amino acid sequence shown in SEQ ID NO: 2 where one or several amino acids are deleted, replaced or added, and having a regulatory activity of chromosome segregation, can be prepared by ordinary methods such as known gene manipulation, point mutation and the like.

As for a DNA of the present invention, a DNA encoding a protein of the present invention that has a regulatory activity of chromosome segregation: a DNA derived from fission yeast *Schizosaccharomyces pombe*, comprising a base sequence shown in SEQ ID NO: 1 or 3 or a complementary sequence thereof; and a DNA containing part or whole of these sequences, encoding a protein that has a regulatory activity of chromosome segregation: a DNA derived from *Saccharomyces cerevisiae*, comprising a base sequence shown in SEQ ID NO: 5 or a complementary sequence thereof; and a DNA containing part or whole of these sequences, encoding a protein that has a regulatory activity of chromosome segregation: a DNA derived from *Neurospora crassa*, comprising a base sequence shown in SEQ ID NO: 7 or a complementary sequence thereof, and encoding a protein that has a regulatory activity of chromosome segregation; and a DNA containing part or whole of these sequences, encoding a protein that has a regulatory activity of chromosome segregation: a DNA derived from *Arabidopsis*, comprising a base sequence shown in SEQ ID NO: 9 or 11 or a complementary sequence thereof, and encoding a protein that has a regulatory activity of chromosome segregation; and a DNA containing part or whole of these sequences, encoding a protein that has a regulatory activity of chromosome segregation: a DNA derived from mouse, comprising a base sequence shown in SEQ ID NO: 13 or 15 or a complementary sequence thereof, and encoding a protein that has a regulatory activity of chromosome segregation; and a DNA containing part or whole of these sequences, encoding a protein that has a regulatory activity of chromosome segregation: a DNA derived from human, comprising a base sequence shown in SEQ ID NO: 17 or 19 or a complementary sequence thereof, and encoding a protein that has a regulatory activity of chromosome segregation; and a DNA containing part or whole of these sequences, encoding a protein that has a regulatory activity of chromosome segregation: a DNA hybridizing with the above DNA under stringent conditions, encoding a protein that has a regulatory activity of chromosome segregation: and the like, can be exemplified.

These DNAs can be prepared by known methods based on DNA-sequence information, such as a gene or cDNA library of yeast, mouse, human and the like. Further, using a base sequence shown in SEQ ID NO: 1, 3, 5, 7, 9, 11, 13, 15, 17, 19, or others or a complementary sequence thereof, or part or whole of these sequences as a probe, DNA libraries of yeast, mouse, human and the like are hybridized under stringent conditions, and the intended DNA encoding a protein that has a regulatory activity of chromosome segregation can be obtained by isolating the DNAs that hybridized with the probes. As for a condition of hybridization to obtain the DNA; hybridization at 42° C., and washing treatment by a buffer containing 1×SSC and 0.1% SDS at 42° C.; preferably hybridization at 65° C., and washing treatment by a buffer containing 0.1×SSC and 0.1% SDS at 65° C.; can be exemplified. Moreover, as for an element affecting the stringency of hybridization, there are various elements other than the above described temperature conditions, those skilled in the art can actualize the stringency equivalent to that of hybridization as exemplified in the above with an appropriate combination of various elements.

As for a fusion protein of the present invention, any protein can be used as long as the protein of the present invention is bound to a marker protein and/or a peptide tag, as for a marker protein, it is not especially limited but a conventionally known marker protein, for example, alkaline phosphatase, Fc region of antibody, HRP, GFP and the like can be exemplified. Further, as for a peptide tag of the present invention, conventionally known peptide tags such as Myc, His, FLAG and GST tags can be specifically exemplified. The fusion protein can be produced by ordinary methods; and is useful for purification of protein Sgo1 and the like by using the affinity of Ni-NTA and His tag, and for a reagent for study in the art.

As for an antibody specifically binding to a protein of the present invention, immunospecific antibodies such as monoclonal antibody, polyclonal antibody, chimeric antibody, single-stranded antibody, humanized antibody and the like, can be specifically exemplified. These antibodies can be produced by ordinary methods with the use of proteins such as the above-mentioned Sgo1 or part thereof as an antigen, and among them a monoclonal antibody is preferable in terms of specificity. Antibodies such as a monoclonal antibody are useful for elucidating the localization of Sgo1 and others in vivo.

The above-mentioned antibodies of the present invention can be generated with the use of common protocol by administering proteins of the present invention or fragments containing epitope thereof, or cells expressing the protein on their membrane surfaces, to animals (preferably non-human). For example, for preparation of a monoclonal antibody any method such as hybridoma (*Nature* 256, 495-497, 1975), trioma, human B cell hybridoma (*Immunology Today* 4, 72, 1983) and EBV-hybridoma (*MONOCLONAL ANTIBODIES AND CANCER THERAPY*, pp. 77-96, Alan R. Liss, Inc., 1985), by which antibodies are generated from cultures of continuous cell lines, can be used.

To generate a single-stranded antibody against a protein of the present invention, a method for preparation of single-stranded antibody (U.S. Pat. No. 4,946,778) can be applied. Further, to express a humanized antibody, transgenic mouse or other mammals can be used, clones that express a protein of the present invention with the use of the above-mentioned antibody can be isolated/identified, and its polypeptide can be purified by affinity chromatography. Antibodies against peptide containing proteins of the present invention or antigen epitopes thereof can be possibly used for diagnosis and treatment of cancer, or of chromosome segregation diseases such as infertility or Down's syndrome using a regulatory factor of chromosome segregation as an index.

Functional analysis of a protein of the present invention can be performed by using fusion proteins fused with, for example; fluorescent substances such as FITC (fluorescein isocyanate) or tetramethyl rhodamine isocyanate; radioisotopes such as 125I, 32P, 14C, 35S or 3H; labelings with enzymes such as alkaline phosphatase, peroxidase, .beta.-galactosidase or phycoerythrin; fluorescence emission proteins such as green fluorescent protein (GFP); or the like, to antibodies such as the above-mentioned monoclonal antibodies. As an immunological assay method with the use of antibody of the present invention, methods such as RIA, ELISA, Fluorescent antibody method, Plaque forming cell assay, Spotting method, Hemagglutination testing, Ouchterlony method can be exemplified.

The present invention will be explained in detail in the following by referring to the examples, but the technical scope of the present invention will not be limited to these.

EXAMPLE 1

[Method]

(Screening of Rec8 Protector)

The present inventor examined a gene that is toxic only when co-expressed with Rec8 in vegetative cells. The Rec8 encoding sequence that was fused with GFP was cloned into pREP82 (ura4+ marker) under the thiamine-repressible nmt1+ promoter, to construct pREP82-rec8+-GFP. A *Schizosaccharomyces pombe* cDNA library constructed by mRNA that was prepared from meiotic cells, and a pREP3 vector (nmt1+ promoter, LEU2+ marker) (Y. Akiyoshi and Y. W., unpublished) were used. The leu1 ura4-D18 cells carrying pREP82-rec8+-GFP were transformed with the cDNA library, spread on agar plates containing thiamine (promoter-off) and incubated for 3 days at 30.degree. C. The colonies were then replicated on two thiamine-free agar plates: one that contains uracil and 5'-fluoroortoic acid (5'-FOA) where only cells lacked the plasmid pREP82-rec8+-CFP can grow (thereby expresses a library clone alone), and the other that does not contain 5'-FOA (allows co-expression of rec8+-GFP and a library clone). The present inventor added Phloxine B, a drug that stains dead cells red, onto the both agar plates, thereby illuminated sick colonies. After incubation for two days, the colonies exhibiting sickness only on the co-expression agar plate were picked up, and the library-derived plasmids were recovered and analyzed.

(*Schizosaccharomyces pombe* Strains)

Deletion and tagging of GFP or FLAG to endogenous sgo1+ and sgo2+ were performed by a PCR-based gene targeting method (*Yeast* 14, 943-951(1998)). By inserting GFP into the C-terminus of the PCR-amplified sgo1+-FLAG, sgo1+-FLAG-GFP was generated and integrated into the endogenous sgo1 locus. Further, a endogenous promoter of the sgo1+ was replaced with a nmt promoter to generate Pnmt-sgo1+ or Pnmt-sgo1+-FLAG-GFP by the PCR-based gene targeting method. The proteins tagged to Sgo1-GFP or Sgo1-FLAG was deleted depending on the purpose. A mei4Δ mutation was used to arrest meiotic cells prior to meiosis I (close to late prophase in meiosis I), and a mes1Δ mutation was used to arrest after meiosis I, as described previously (*Nature* 400, 461-4(1999)).

(Observation of Chromosomes Marked with GFP)

To observe the segregation patterns of homologues at meiosis I, h90 cells retaining cen2-GFP (*Embo J* 22, 2284-96(2003)) were spotted on meiosis-inducing medium, SPA. To examine the segregation patterns of sister chromatids, opposite mating type cells, one marked with cen2-GFP and the other not marked, were mixed and spotted on SPA. After incubation for one day, the zygotes were monitored for GFP. Images were obtained under a microscope (Axioplan2, Zeiss) equipped with a cooled CCD camera (Quantix, Photometrics) and by using Metamorph software (Universal Imaging Corporation). Seven Z-sections for GFP signals were converted to single two-dimensional images by taking the maximum signal at each pixel position in the images.

(Chromatin Immunoprecipitation; ChIP)

Diploid sgo1+-FLAG-GFP was used for ChIP with Sgo1. To achieve a highly synchronous culture, the endogenous slp1+ promoter was replaced with the rad21+ promoter that is not active during meiosis, and the cells were arrested at metaphase I. The cells were incubated in nitrogen-depleted medium for 17 hours at 30° C., and 60% the cells or less were arrested at metaphase I. For ChIP with Sgo2, nda3-KM311 sgo2+-GFP cells were proliferated at 30° C., and then shifted to 18° C. After incubation for 8 hours, most of the cells were arrested at metaphase. The cells were fixed with 3% paraformaldehyde for 30 minutes at 18° C., and extracts were prepared. The DNA was broken to an average size of 400 bp, and the extracts were immunoprecipitated with rabbit anti-GFP antibodies (Clontech). DNAs prepared from the whole cell crude extracts, or immunoprecipitated chromatin fractions were analyzed by quantitative PCR, with a LightCycler or a Lightcycler-DNA Master SYBR Green I kit (Roche Molecular Biochemicals). Antibody-minus samples were used as controls in each experiment to explain the nonspecific binding in the ChIP fractions.

(Preparation of Anti-Sgo1 Antibodies)

Sgo1+ ORF was PCR-amplified from an *Schizosaccharomyces pombe* cDNA library, and inserted into plasmids pGEX4T-2 (Pharmacia Biotech) and pET-19b (Novagen) respectively to prepare recombinant proteins GST-Sgo1 and His-Sgo1. GST-Sgo1 was used to immunize rabbit, and the raised antibodies were purified by His-Sgo1 as described previously (*Embo J* 22, 5643-53(2003)). Furthermore, for the purpose of analyzing proteins (SEQ ID NOs: 18 and 20; hSgo1 and hSgo2 respectively) encoding human shugoshin homologous gene (SEQ ID NOs: 17 and 19), part of hSgo1 and hSgo2 was expressed in *E. coli*, and antibodies against hSgo1 and hSgo2 were produced by injecting the protein into rabbit.

(Immunostaining)

To stain endogenous Sgo1, wild-type diploid cells cultured for 5 hours in MM-N were fixed with 3% formaldehyde for 40 min at 30° C., and stained by the method described previously (*Embo J* 22, 5643-53(2003)). To stain Sgo2-GFP and Mis6-HA, logarithmically growing cells were used. Sgo1 was detected by using rabbit anti-Sgo1 antibody at 1:50 and Alexa488-conjugated anti-rabbit antibody (Molecular Probes) at 1:100. Tubulin was detected by using mouse anti-tubulin antibody TAT-1 (provided by Keith Gull) at 1:200 and Cy3-tagged anti-mouse antibody (Chemicon) at 1:2000. Cells were counterstained with DAPI to visualize DNA. The Sgo2-GFP was detected by using mouse anti-GFP antibody (Roche) at 1:50 and BODIPY FL-conjugated anti-mouse antibody (Molecular Probes) at 1:100. The Mis6-HA was detected by using rabbit anti-HA antibody Y-11 (Santa Cruz) at 1:50 and Alexa488-conjugated anti-rabbit antibody at 1:100. Cells were counterstained with DAPI to visualize DNA. Further, immunostaining was performed by using rabbit anti-hSgo1 antibody and rabbit anti-hSgo2 antibody in the same manner as the above.

(Coimmunoprecipitation)

Padh-rec8+-3HA Pnmt41-sgo1+-FLAG-GFP strain cells and control Padh-rec8+-3HA strain cells were cultured without thiamine for 15 hours at 30° C., collected, and the extracts were prepared. To liberate chromatin-bound proteins, the extracts were treated with DNase I. After clarifying the extracts by centrifugation, the Sgo1-FLAG-GFP protein was immunoprecipitated with anti-FLAG antibody M2 (Sigma). The Rec8-3HA and Sgo1-FLAG-GFP were detected by anti-HA antibody Y-11 and anti-FLAG antibody M2, respectively.

(Analysis of Budding Yeast)

All sample strains except those for chromosome loss assay are derivative of SK1 (*Cell* 98, 91-103(1999)). The chromosome loss assay was performed as described previously (*Nature* 410, 955-9(2001)). The ScSGO1 gene was deleted or epitope-tagged by using PCR generated cassettes (*Yeast* 14, 953-961(1998)). Accurate gene targeting was checked by PCR. URA3-GFP dots marking chromosome V (cenV-GFP) were described previously (*Cell* 98, 91-103(1999)). Sporulation was induced by culturing diploid cells at 30° C. as described previously (*Dev Cell* 4, 535-48(2003)). In situ immunofluorescence was performed as described previously (*Dev Cell* 4, 535-48(2003)).

(Cell Culture)

HeLa cells were cultured in DMEM supplemented with 10% fetal bovine serum and 0.03% L-Glutamine. The HeLa cell strain expressing Scc1-myc was cultured with 200 μg/ml of G418 (Invitrogen) and 100 μg/ml of Hygromycin B (Wako). Expression of Scc1-myc was induced by incubation with 2 μg/ml of Doxycyclin (Sigma) for 48 hours.

(Preparation of Anti-Human Sgo Antibody)

As the information for N-terminal amino acid sequence of human Sgo1 was not obtained from the databases, the present inventor cloned a cDNA fragment that was amplified from a cDNA library (BD Biosciences) with the use of primers recognizing the cloning site of .lamda.TriplEx: CTCGGGAAGCGCGCCATTGTG (SEQ ID NO: 38) and the DNA sequence corresponding to the numbers 237-242 in amino acid sequence of Q9BVA8: CCTGGCTGAATCAGCTTTGGTG (SEQ ID NO: 39). The Sequencing revealed that the Sgo1 mRNA encodes a protein having 527 amino acids. To obtain polyclonal antibodies against Sgo1, a cDNA fragment encoding the numbers 109-491 in amino acid sequence of Sgo1 was amplified and inserted into the reading frames of plasmids pGEX4T-2 (Amersham) and pET19b (Novagen) to produce GST-Sgo1 and His-Sgo1 respectively, and followed by immunization of a rabbit (QIAGEN) (performed according to the manufacturer's instructions). His-Sgo1 was affinity-purified on CNBr-activated sepharose (Amersham). Antibodies against Sgo2 were raised with GST-Sgo2 (amino acid numbers 331-631) and purified with His-Sgo2 in the same manner as the above.

(Immunofluorescence Microscopy and Chromosome Spreading)

Immunofluorescent staining was performed as described in the above, by using anti-human Sgo1 (1:1000), anti-human Sgo2 antiserum (1:10000), anti-Bub1 (1:1000, MBL), anti-BubR1 (1:1000, MBL), anti-CENP-A (1:1000, MBL), anti-Aurora B AIM-1 (1:1000, BD Biosciences) and anti-tubulin DM1A (1:1000, Sigma). Immunostaining of Scc1-myc was performed as described in the above, by using anti-myc CM-100 (1:1000, Gramsch Laboratories) and ACA (1:1000, provided from Dr. Yoshinari Takasaki). As a secondary antibody, Alexa Fluor 488 goat anti-rabbit antibody (1:1000, Molecular Probes), Cy3 conjugated anti-mouse antibody (1:1000, CHEMICON), and Cy3 conjugated donkey anti-human antibody (1:1000, Jackson ImmunoResearch Laboratories. Inc) were used. 3 μg/ml of Hoechst 33342 or 0.5 μg/ml of DAPI were used for counter staining. Images were taken by using SlideBook or MetaMorph software.

(Chromosome Spreading)

HeLa cells during mitosis were collected by mitotic shake-off and incubated with 330 nM of nocodazole for 0 up to 4 hours. Chromosome spreading was performed as described in the above.

(Immunoblotting)

HeLa cells were boiled with the sample buffer and resolved by SDS-polyacrylamide gel electrophoresis. Proteins were transferred to Immobilon-P membrane (Millipore), followed by blocking with 5% Skim milk (Nacalai) in TBST (150 mM of NaCl, 20 mM of Tris-HCl pH7.4, 0.05% Tween-20). Antibody incubations were performed in 0.1% skim milk TBST supplemented with anti-Sgo1 antibody (1:1000), anti-Sgo2 antibody (1:1000), anti-Bub1 antibody (1:500) and anti-tubulin antibody (1:3000). Blots were produced by ECL (Amersham).

(RNAi)

As a siRNA target sequence, hSgo1: AAGUCUACUGAUAAUGUCUUATT (SEQ ID NO:40) and hSgo2: AAGCACUACCACUUUGAAUAATT (SEQ ID NO:41), and human Sgo1: GUGAGCCUCUGUGAAUCAATT (SEQ ID NO:42) and human Sgo2: GCUCUCAUGAACAAUAACUTT (SEQ ID NO:43) were respectively selected on hSgo1RNA or hSgo2RNA. Furthermore, as a siRNA target sequence, GAGUGAUCACGAUUUCUAATT (SEQ ID NO: 44) was selected on other siRNA target sequence, Bub1RNA; siRNA target sequence, AACGGGCAUUUGAAUAUGAAA (SEQ ID NO: 45, see *JCS*, 117, 1577-1589(2004)) was selected at 2 sites on a spindle checkpoint factor BubR1 RNA. These sequences were synthesized as double strand, and introduced into cells by using oligofectamine (Invitrogen). Furthermore similarly, when producing HIV vector, HeLa cells were transfected with HIV plasmid vector, pMD.G (VSV-G env expressing plasmid), pMDLg/p.RRE (the third generation packaging plasmid) and pRSV Rev (Rev expressing plasmid) by calcium phosphate method, collected the culture supernatant 48 hours after the transfection, and condensed to use as a virus vector.

EXAMPLE 2

[Results]

(Identification of Shugoshin Sgo1 in Fission Yeast)

Figure 1:
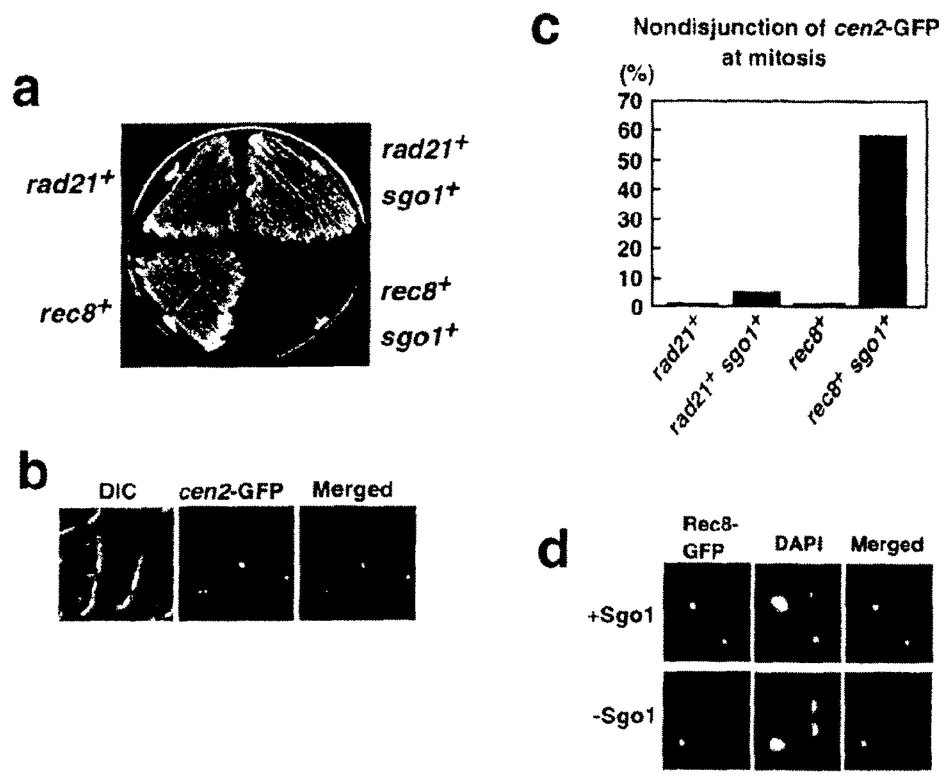
FIG. 1 is a set of pictures showing that sister chromatids are not segregated during mitosis by co-expression of Sgo1 and Rec8 in the present invention. a.) The cen2-GFP strains expressing the genes indicated by endogenous promoters (a constitutive chromatin promoter for rad21+ or rec8+, and a thiamine-repressible promoter Pnmt1 for Sgo1+) were streaked on a thiamine-depleted plate. b.) Samples of Padh1-rec8+Pnmt1-sgo1+ cells cultured for 15 hours at 30° C. after thiamine depletion. The non-segregation of cen2-GFP (asterisk) was identified in the septate junction cells. c.) The non-segregations of cen2-GFP were counted (n>100). d.) The Padh1-rec8+-GFP strains were cultured with or without the use of Pnmt1-sgo1+ in the same manner as (b). Samples of cells at interphase and anaphase are shown.
Figure 2:
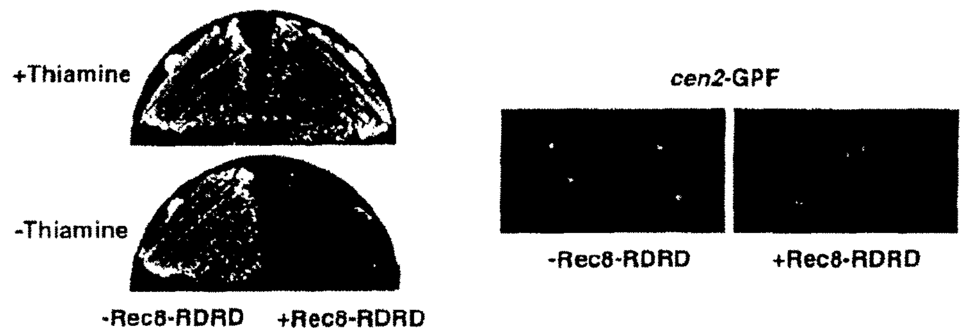
FIG. 2 is a set of pictures showing that sister chromatid segregation was undergone in mitosis by expression of non-cleavable Rec8. The plasmid pREP41-rec8-RDRD (expressing non-cleavable Rec8 (*Embo J* 22, 5643-53(2003))) was integrated into the chromosome of cen2-GFP cell strains (+Rec8-RDRD), and the cells were streaked on plates with or without the presence of thiamine. The host strain cells (−Rec8-RDRD) were similarly cultured as a control. Note that Rec8-RDRD is expressed only on the thiamine-free plate. Samples of cells cultured in culture medium for 15 hours at 30° C. after the depletion of thiamine.

The replacement of the mitotic cohesin, Rad21/Scc1, with the meiotic version, Rec8, is a prerequisite for protecting centromeric sister chromatid cohesion through anaphase of meiosis I ((*Cell* 103, 1155-68(2000), *Mol Cell Biol* 23, 3965-73(2003)). However, when Rec8 was expressed ectopically during mitosis, Rec8 was localized largely at centromeres but disappeared at anaphase, with sister chromatids segregating to opposite sides (FIGS. 1*c* and *d*). Moreover, the ectopic expression of non-cleavable Rec8 during mitosis (note that Rec8 is cleaved by separase Cut1 during meiosis (*Embo J* 22, 5643-53(2003))) resulted in an inability to separate sister chromatids (see FIG. 2). Thus, in contrast to the situation during meiosis I, centromeric Rec8 is cleaved by separase during mitosis, and results in separation of sister chromatids. The present inventor thus postulated a meiosis I specific centromeric protector of Rec8 from these observations. To identify this factor, the present inventor searched for a gene that generates toxicity during mitotic growth only when co-expressed with Rec8. This screening identified a novel gene, sgo1+ (ORF: SPBP35G2.03C). The hindrance of growth by Sgo1 was significantly dependent on Rec8, as Sgo1 had little effect on growth when co-expressed with Rad21 (FIG. 1*a*). Co-expression of rec8+ and sgo1+ resulted in high frequency of the blocked nuclear division, as centromere-associated green fluorescent protein markers (cen2-GFP) segregated to the same side of a septated cell highly frequently (see FIGS. b and c). To test the possibility that Sgo1 protects Rec8 from degradation at anaphase, the localization of Rec8 was examined in associated with Sgo1 expression, Rec8 tagged with GFP at its carboxyl terminus was expressed under the control of a constitutive adh1 promoter and induced Sgo1 by using a thiamine-repressible nmt1 promoter. Consequently it was found that the Rec8-GFP signal persisted through anaphase only when Sgo1 was co-expressed (FIG. 1*d*). As Sgo1 is expressed exclusively in meiosis (DNA micro array data (*Nat Genet* 32, 143-7(2002)), see below), it was found from the above-mentioned results, that Sgo1 is a protector of Rec8 during meiosis.

(Sgo1 Protects Centromeric Cohesion at Meiosis I)

Figure 3:
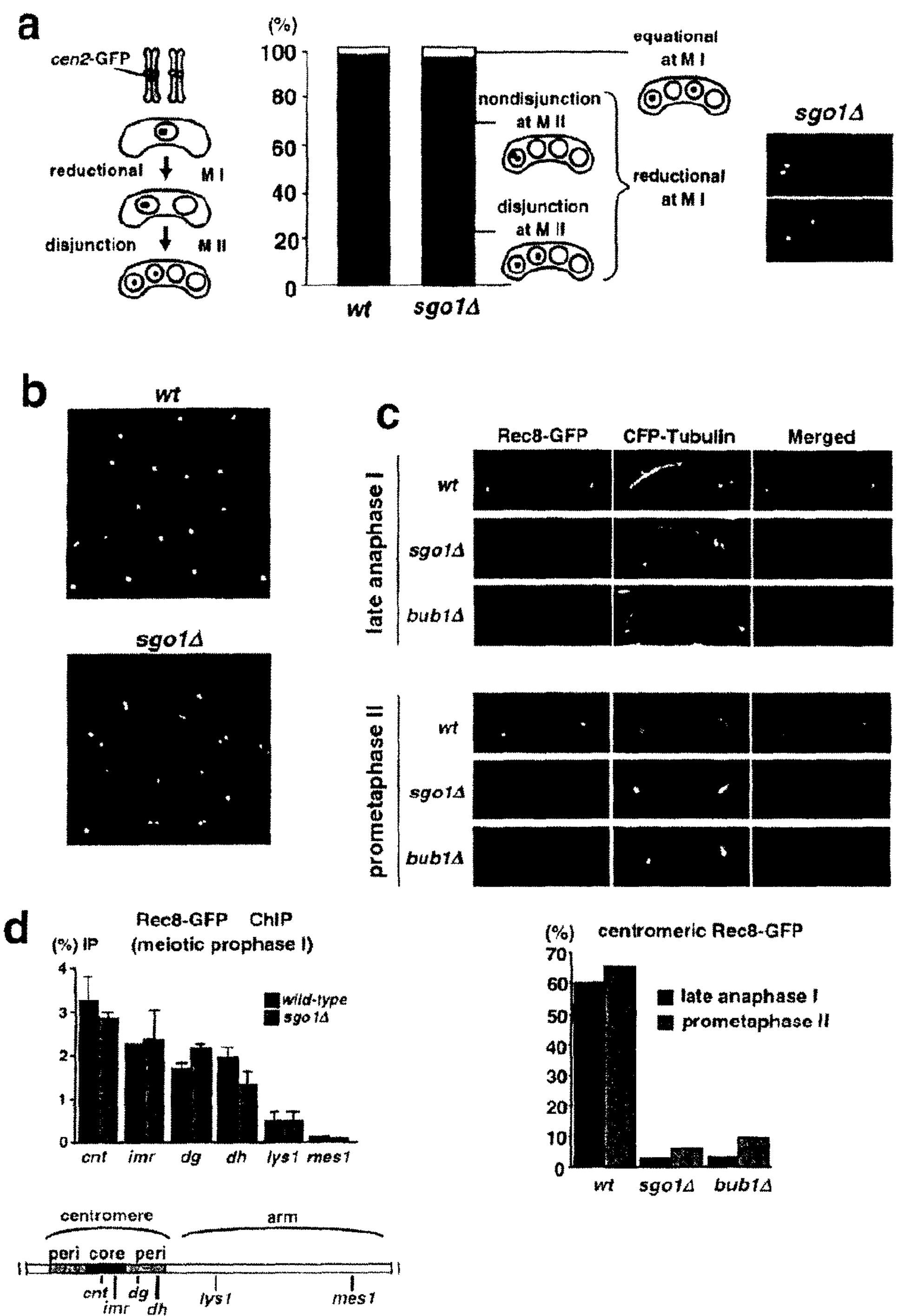
FIG. 3 is a set of pictures showing that sgo1 of the present invention is required to protect Rec8 and thereby cohesion at centromeres arises during anaphase of meiosis I. a.) As for one of the homologues marked with cen2-GFP, segregation during meiosis was observed in wild-type and sgo1Δ cells (n>170). A normal segregation pattern of cen2-GFP is illustrated (left). Samples of sgo1Δ cells are shown (right). b.) Separation of sister cen2-GFP dots after meiosis I (mes1Δarrest) is evident in sgo1Δ cells. c.) The Rec8-GFP signal was observed in the indicated cells at late anaphase I (n>30) and at prometaphase II (n>100), and the frequency of centromeric Rec8-GFP displayed in the cells was counted. The spindles were visualized by expressing CFP-Atb2 (a2-tubulin) (Curr Biol 11, 836-45(2001)). d.) Rec8-GFP levels throughout the indicated chromosome sites in the arrested cells were measured prior to meiosis I (mei4Δ arrest) by ChIP assay with the use of anti-GFP antibodies. The bottom panel shows *Schizosaccharomyces pombe* chromosome I schematically, and the primers (cnt, imr, dg, dh, lys1, mes1) were used there.

To examine whether Sgo1 is actually required for the protection of Rec8 during meiosis, the entire ORF encoding sgo1+ was deleted, and the phenotype was examined. Sgo1Δ cells are viable and showed normal vegetative growth, consistent with the concept that sgo1+ is a meiosis-specific gene. To examine the meiotic chromosome segregation of sgo1Δ cells, centromere-linked sequences were marked with GFP (cen2-GFP) on only one of the two homologues in a zygote, and the segregation of the GFP dots were monitored during meiosis I. It was revealed that meiosis I emerged normally in sgo1Δ cells, as sister chromatid pairs generally moved together to the same side of each zygote. Therefore, monopolar attachment was intact (FIG. 3*a*). Moreover, by marking cen2-GFP on both chromosomes, it was determined that accurate segregation was undergone with homologues at meiosis I (data not shown). However, sister chromatid pairs failed to segregate properly at meiosis II, non-segregation was caused in 50% of the cells or less (FIG. 3*a*). This value is consistent with random chromosome segregation at meiosis II.

To examine centromeric cohesion, cen2-GFP marked on both homologues was monitored in zygotes arrested prior to meiosis II via a mes1Δ mutation. Supporting the above results, sgo1Δ cells frequently showed precocious division of centromeres as split cen2-GFP signals prevailed in the dyad nuclei (FIG. 3*b*). Finally, it was examined whether protection of Rec8 at centromeres is dependent on Sgo1 by monitoring Rec8-GFP at late anaphase I and prometaphase II. While it is significant that Rec8 signals were centromeric in wild-type cells, the Rec8 signals had largely disappeared from the centromeres at these stages in sgo1Δ cells (FIG. 3*c*). Although all phenotypes of sgo1Δ cells are reminiscent of heterochromatin-deficient *Schizosaccharomyces pombe*, in which Rec8 localization to the pericentromeric regions is decreased and centromeric cohesion is lost during meiosis I, leading to random division at meiosis II (*Science* 300, 1152-5(2003)). Chromatin binding by Rec8 was examined in cells arrested prior to meiosis I by using a chromatin immunoprecipitation (ChIP) assay. In marked contrast to heterochromatin-deficient cells, Rec8 localization was intact in sgo1Δ cells at the pericentromeric regions as well as all other regions tested. These results suggest that the loss of centromeric Rec8 after meiosis I is caused not by an initial defect in Rec8 localization to centromeres but rather by a defect in the preservation of centromeric Rec8 during meiosis I. The above results indicated that the Cut1 separase becomes active at the onset of anaphase I and cleaves most chromosomal Rec8, leaving only centromeric Rec8 intact (*Embo J* 22, 5643-53(2003)). These results indicated that Sgo1 plays an essential role in protecting centromeric cohesion throughout meiosis I by protecting cohesin Rec8 from separase cleavage.

(Sgo1 Localizes at Centromeres During Meiosis I)

Figure 4:
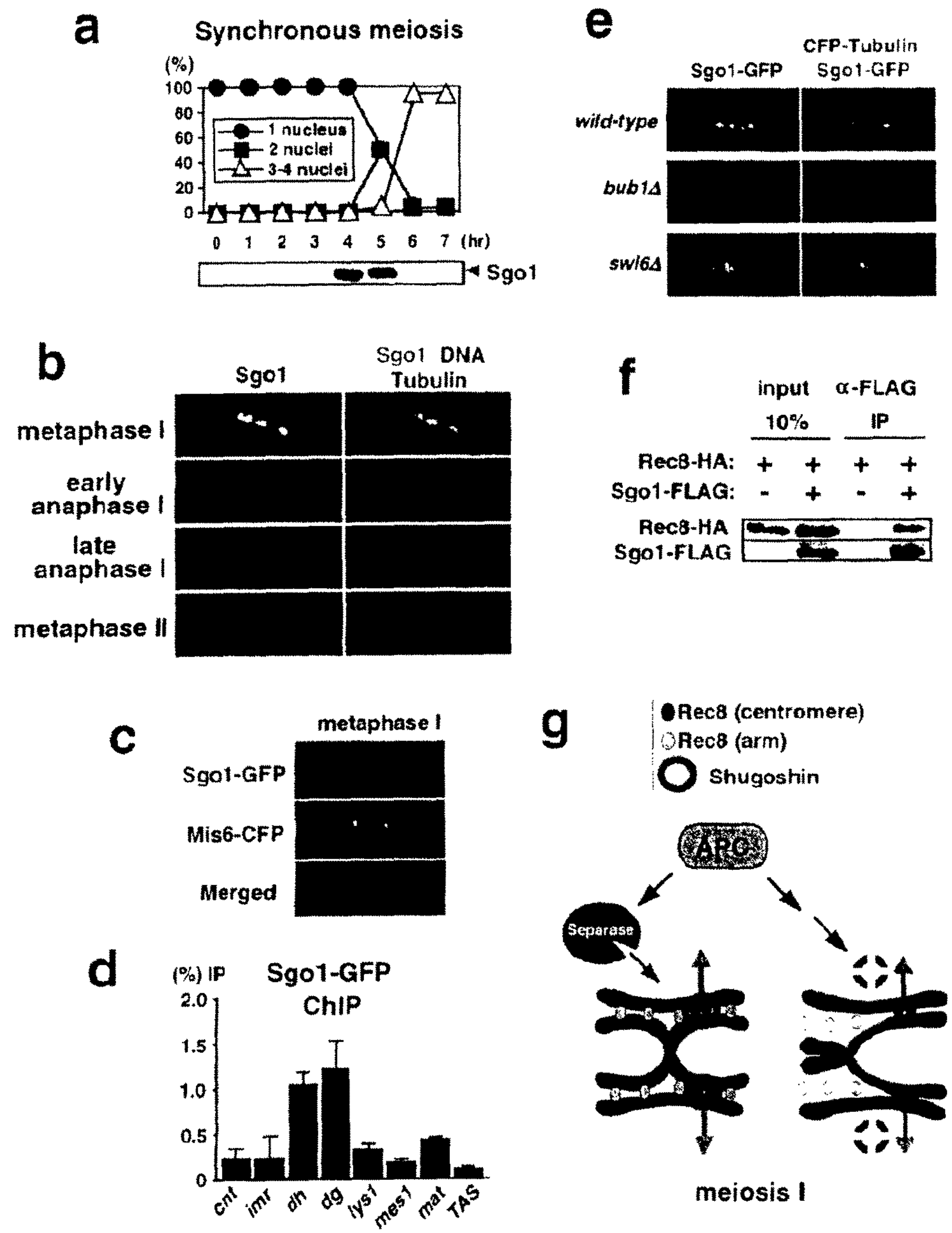
FIG. 4 is a set of pictures showing that Sgo1 of the present invention localizes at pericentromeric regions during meiosis I. a.) Synchronous meiosis of diploid pat1-114/pat1-114 cell strains (*Embo J* 22, 5643-53(2003)) was sampled, meiotic nuclear division was monitored by DAPI staining, and the protein level of Sgo1 was detected by Western blotting with the use of anti-Sgo1 antibodies. b.) Sgo1 (green) was counterstained with tubulin (red) and DAPI (4'6'-diamidino-2-phenylindole) (blue) at the indicated stages in meiotic cells. c.) A sgo1+-GFP cell co-expressing mis6+-CFP was examined under fluorescence microscopy. Sgo1-GFP (green) and Mis6-CFP (red) are merged. d.) Sgo1-GFP levels throughout the indicated chromosome sites in cells arrested at metaphase I were measured by ChIP assay with the use of anti-GFP antibodies. The same primers as for FIG. 2*d* in synchronism with additional primers at mat (heterochromatin region at the mating type locus) and TAS (telomere associated sequence) were used. e.) Sgo1-GFP (green) was detected at metaphase I in the indicated cells that express CFP Atb2 to visualize spindles (red). f.) Rec8-HA was expressed with or without Sgo1-FLAG in proliferating cells, and the extracts were immunoprecipitated with anti-FLAG antibody. g.) A model for the action of shugoshin in meiosis. Shugoshin protects centromeric Rec8 complexes from cleaving by separase at the onset of anaphase I, thereby preserves the centromeric cohesion until meiosis II. Shugoshin is degraded depending on APC during anaphase I.
Figure 5:
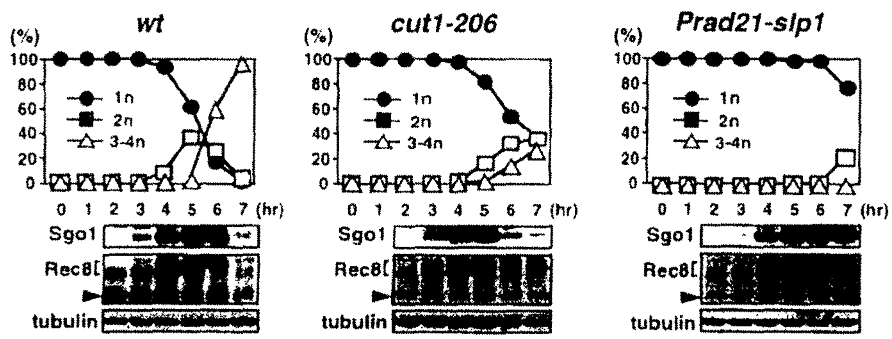
FIG. 5 is a set of pictures showing the time-dependent change of the expression levels of Sgo1 and Rec8 in synchronous culture of haploid pat1-114 cell strains (wt), and of cut1-206 or Prad21-slp1 cells. The expression of slp1+ (a fission yeast CDC20 homologue required for APC activation (*Mol Cell Biol* 17, 742-50(1997))) was repressed during meiosis in Prad21-slp1 cells where slp1 promoter was replaced with rad21. Meiotic nuclear division was monitored by DAPI staining, and the protein levels of Sgo1, Rec8, and tubulin (control) were measured by western blotting with the use of anti-Sgo1, anti-Rec8 and anti-tubulin antibodies, respectively. Although cut1-206 cells together with normal kinetics led to Sgo1 degradation, Rec8 degradation was delayed. Prad21-slp1 cells showed delayed degradation of Sgo1 as well as Rec8. Arrowheads indicate a cleavage product of Rec8 by separase Cut1.

To detect the Sgo1 protein, Sgo1-specific antibodies were produced, and the results of Western blotting indicated that Sgo1 is expressed only around at meiosis I (FIG. 4*a*). The results of immunofluorescence microscopy on cells at various stages of meiosis revealed that Sgo1 appears at late prophase of meiosis I and is fully localized as several punctuate dots by the point of metaphase I (FIG. 4*b*). These dots were co-localized with the Mis6 kinetochore protein (*Cell* 90, 131-143(1997)), and indicated that Sgo1 is a centromere-associating protein (FIG. 4*c*). At the onset of anaphase I, Sgo1 signals decrease dramatically. It was found that Sgo1 remains undegraded at centromeres in APC-depleted cells arrested at metaphase I but undergoes normal degradation in separase-defective cells (FIG. 5), and indicated that Sgo1 degradation at anaphase I is regulated more directly by the APC rather than through separase. Although residual Sgo1 signals were detectable at the centromeres in early anaphase I, they disappeared completely by the end of anaphase I (FIG. 4*b*). This indicates that a substantial amount of Sgo1 is required at the onset of anaphase I when separase is fully activated. However, it is considered that the amounts of Sgo1 required are smaller and smaller as anaphase I progressed. This idea is tenable when the separase, activity is quickly down-regulated or when the access to chromosomes is prevented during anaphase I. Sgo1 never reappears during meiosis II (FIG. 4*b*), and which is consistent with the idea that Sgo1 is required for the protection of Red8 only during meiosis I.

The present inventor has already reported that Rec8 localization at pericentromeric regions is especially important for the persistence of centromeric cohesion throughout meiosis I (*Science* 300, 1152-5(2003)). If Sgo1 is a centromeric protector of Rec8, then it might be expected to localize there as well. To test this possibility, Rec8 localization was delineated more precisely by using the ChIP assay. Sgo1 actually associated with pericentromeric heterochromatin regions rather than with central core regions along the centromere sequences (FIG. 4*d*). As the results of immunoprecipitation experiments indicated that Sgo1 interacts with Rec8 complexes in vivo (FIG. 4*f*), the protection was carried out through close interaction. Concurrently, these results indicate that Sgo1 resides at pericentromeric regions and acts to protect centromeric Rec8 from the cleavage of separase at anaphase I (FIG. 4*d*). It was found that the localization of Rec8 does not depend on Sgo1, and vice versa (FIG. 3*d*, figure not shown). Actually, the Rec8 and the Sgo1 are in fact independently generated at pericentromeric regions, as for the localization, the Rec8 and the Sgo1 depend on heterochromatin and Bub1 kinase respectively (FIG. 4*e*). In contrast, Rec8 and Sgo1 are localized at centromeres in swi6Δ (heterochromatin deficient) and bub1Δ cells respectively (FIG. 4*e*). Thus by localizing independently, it can be ensured that Rec8 is protected only at centromeres not along the chromosomal arm regions.

Further, it is indicated that shugoshin shields Rec8 physically from the action of separase and counteracts the effects.

Figure 6:
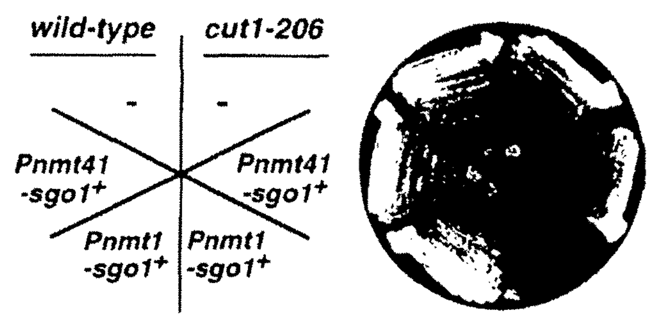
FIG. 6 is a set of pictures showing that ectopic expression of sgo1+ inhibits the growth of the cut1-206 mutant. Chromosomal sgo1+ promoter was replaced with Pnmt1 or Pnmt41 (a weaker version of Pnmt1), and the effect on the mitotic growth in cut1-206 temperature-sensitive cells was examined. The indicated cells were streaked on a plate without thiamine and cultured for 3 days at 28° C. The cut1-206 cells moderately expressing Sgo1 by Pnmt1, arrested mitotic growth even at the permissive temperature, whereas cut1+ cells grew normally.

On this point, even when the strong expression of Sgo1 dose not express Rec8, the mitotic growth was moderately disturbed (figure not shown); and even when the temperature is tolerated for cut1 allele, it was found that cut1 mutant was killed by moderate expression of Sgo1 (FIG. 6).

(Sgo2 is a Mitotic Sgo1 Paralogue in Fission Yeast)

Figure 7:
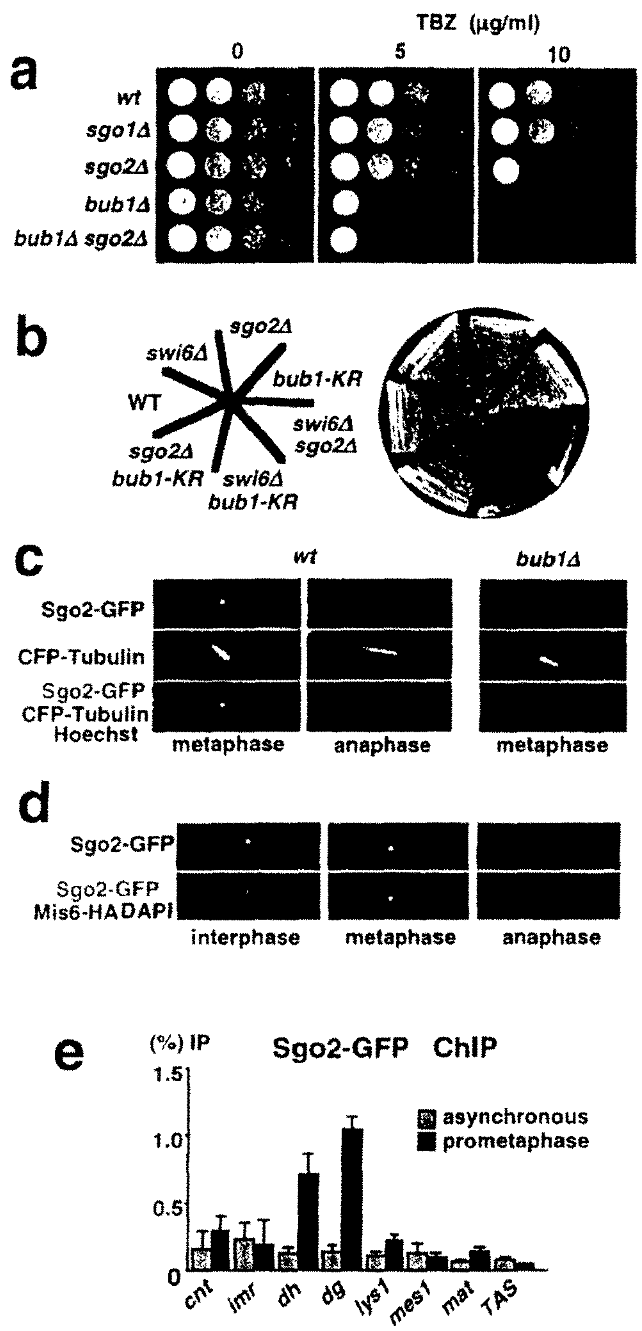
FIG. 7 is a set of pictures showing that Sgo2 of the present invention plays an important role in mitotic at centromere. a.) Serial dilutions of the indicated cultures were spotted onto YEA plates containing 0, 5 or 10 μg/ml of TBZ, and cultured for 3 days at 30° C. b.) The indicated strains were streaked on YEA plates and cultured for 3 days at 30° C. c.) Sgo2-GFP (green) was detected at anaphase I in wild-types and in bub1Δ cells that express CFP-Atb2 to visualize spindles (red). DNA was stained with Hoechst (blue). Wild-type cells at anaphase are also shown. d.) The sgo2+-GFP mis6+-HA cells were fixed and stained with anti-GFP and anti-HA antibodies. e.) Sgo2-GFP levels were measured throughout the indicated chromosome sites in cells arrested at prometaphase or in asynchronous cells by ChIP assay.

By a conventional BLAST search of genome databases, the present inventor identified Sgo1-like proteins from *Saccharomyces cerevisiae* and *Neurospora crassa*, and indicated that Sgo1 is a conserved protein (see below). In the same search, a *Schizosaccharomyces pombe* Sgo1 paralogue which the present inventor named Sgo2, was also identified (ORF: SPAC15A10.15). The sgo2+ gene was disrupted, and it was identified that sgo2Δ cells are viable but show sensitivity to the spindle destabilizing drug thiabendazole (TBZ) (FIG. 7*a*). As sgo1Δ cells never show such a defect, this phenotype is remarkable. To investigate its cellular distribution, the endogenous sgo2+ gene was tagged with GFP. In proliferating cells, Sgo2-GFP was observed as two or three dots in the nucleus (FIG. 7*d*). However, Sgo2-GFP co-localized with the centromere protein Mis6 at metaphase and disappeared during anaphase (FIGS. 7*c* and *d*). The results of ChIP assays showed that Sgo2 chromatin association is detectable only on synchronous populations of mitotic cells, and that chromatin association is localized to the pericentromeric regions (FIG. 7*e*). By enhancing this localization, sgo2 deletion confers a dramatic defect to chromosome segregation when the heterochromatin-deficient swi6Δ mutation was bound thereto, however which by itself impairs centromeric function slightly (*Science* 269, 1429-31(1995)) (FIG. 7*b*). These results indicate that Sgo2 cooperates with centromeric heterochromatin factors to ensure chromosome segregation at mitosis. Moreover, it was found that sgo2Δ cells have a modest increase (up to 15%) in non-segregation of homologues at meiosis I, and indicated that Sgo2 is also important for promoting proper meiosis I. However, the role of Sgo2 does not overlap with that of Sgo1, as sgo1Δ neither causes an apparent defect at meiosis I (FIG. 3*a*) nor enhances a defect of sgo2 in meiosis.

(Shugoshin Localization Controlled by Bub1)

As centromeric Rec8 cannot be detected after meiosis I in fission yeast bub1 mutants, a conserved centromere-associated kinase Bub1 is considered to function in protecting Rec8 during meiosis, (*Nat Cell Biol* 3, 522-6(2001)) (FIG. 3*c*). Although bub1 mutation has pleiotropic effects in meiotic chromosome segregation, it is considered that Sgo1 function can be targeted by Bub1 activity. To elucidate this problem, Sgo1-GFP signals were examined in bub1Δ cells undergoing meiosis. Obviously, Bub1Δ cells were almost completely devoid of accurate centromeric Sgo1-GFP signals, instead showed a diffuse fluorescence in the nucleus (FIG. 4*e*). Similar results were obtained by using the bub1-K762R point mutation that abolishes the kinase activity (Embo J 22, 1075-87(2003)). Although substantial levels of Sgo1 protein were detected in meiotic bub1Δ cells by Western blot analysis (figure not shown), Bub1 dose not influence protein stability of Sgo1. Thus, the kinase activity of Bub1 is required for incorporating Sgo1 to centromeres, and the observed defects in centromeric protection in bub1Δ cells can be explained by impaired localization of Sgo1.

In parallel experiments, it was identified that mitotic Sgo2 localization at centromeres was similarly disturbed in bub1 mutants (FIG. 7*c*). It has been indicated that loss of Bub1 function causes centromeric function to be weakened (J Cell Biol 143, 1775-87(1998)). In this regard, the bub1-K762R mutation shows co-lethality with swi6Δ, a mutation that also slightly impairs centromeric function via its role in pericentromeric heterochromatin formation. It was found that sgo2Δ similarly shows co-lethality with swi6Δ (FIG. 7*b*), and exhibits severe miss-segregation of chromosomes at mitosis (figure not shown). As the sgo2Δ bub1Δ double mutant showed no cumulative defects at all in growth or TBZ sensitivity (FIG. 7*a*), Sgo2 and Bub1 tandem function was confirmed to ensure chromosome segregation in mitosis by these genetic analyses. Taken all together, the above results revealed that the incorporation of Sgo1 and Sgo2 to centromeres is a crucial function of Bub1 kinase in meiosis and mitosis, respectively.

(Characteristics of a Budding Yeast Sgo1 Homologue)

Figure 8:
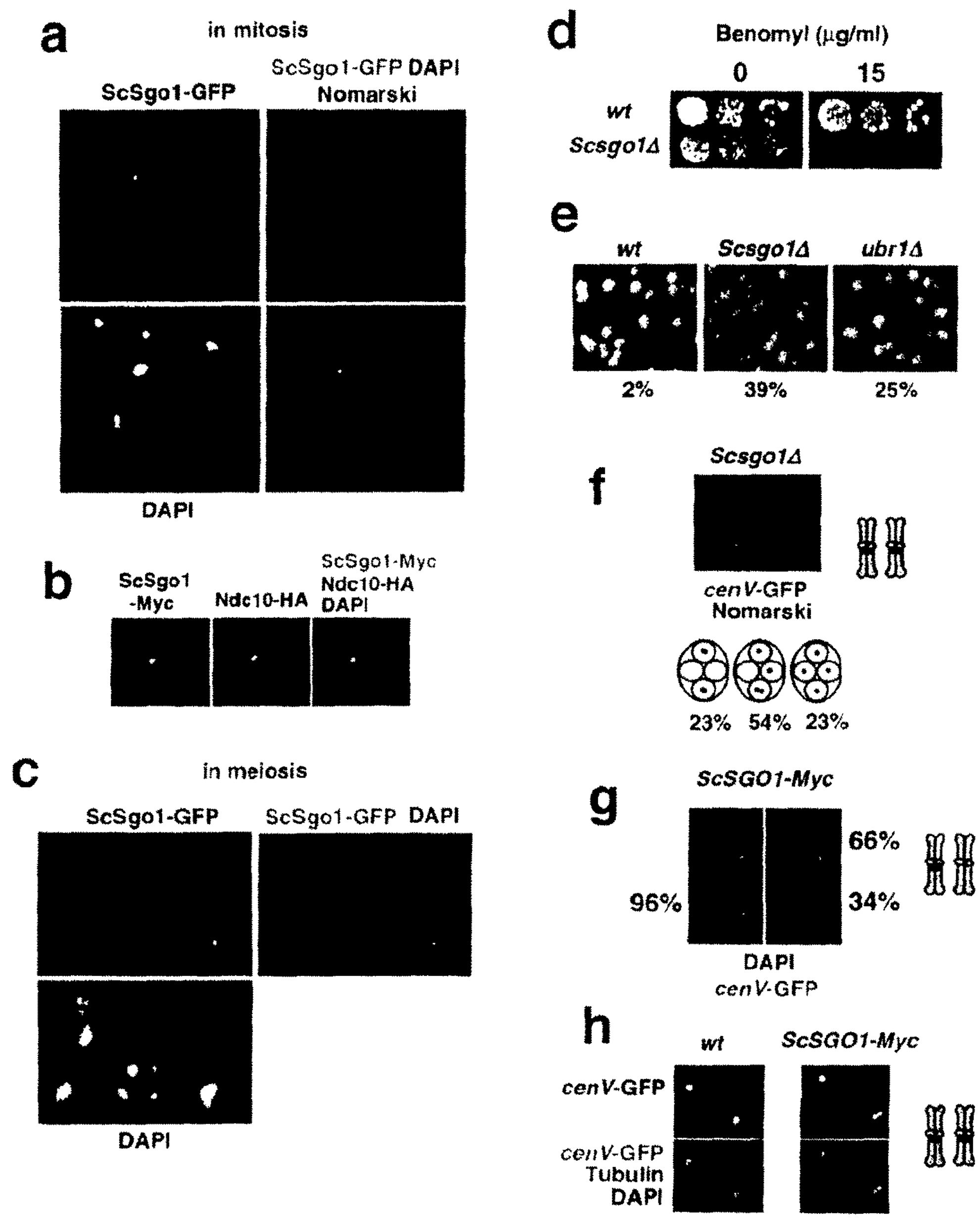
FIG. 8 is a set of pictures showing the results of analysis of budding yeast shugoshin ScSgo1 of the present invention. a.) Budding yeast ScSGO1-GFP diploids in proliferation were fixed with methanol and counterstained with DAPI. b.) ScSGO1-Myc NDC10-HA cells were fixed, and stained with DAPI and antibodies against Myc and HA. c.) ScSGO1-GFP diploids causing meiosis in culture medium were fixed with methanol and counterstained with DAPI. d.) Serial dilutions of the indicated cultures were spotted onto YPD plates containing 0 or 15 μg/ml of benomyl. e.) Chromosome loss was analyzed in wild-types (wt) and Scsgo1Δ mutants by a colony sectoring assay. The loss of nonessential chromosome fragments resulted in a red sector in a white colony. As a positive control, ubr1Δ mutant was used (*Nature* 410, 955-9(2001)). The frequency of sectoring colonies is shown at the bottom (n>120). f.) Samples of segregation of cenV-GFP in Scsgo1Δ tetrads. The segregation patterns in tetrads were mostly classified as one of the three shown at the bottom. The each population (n=200) is also shown. g.) ScSGO1-Myc diploids were induced by synchronous meiosis and were examined the segregation of cenV-GFP marked on one of two homologues at meiosis I and meiosis II. Although most of the cells caused reductional segregation pattern at meiosis I (96%, n=207), the incidence of non-segregation was high at meiosis II (34%, n=322). h.) The cells marked with cenV-GFP on both homologues were induced to meiosis, and counterstained with anti-tubulin antibody and DAPI. Cells at late anaphase I were examined for cenV-GFP dots. ScSGO1-Myc cells frequently showed split cenV-GFP dots at either pair of sister chromatids (72%, n=138), while control wild-type cells did not (<2%, n=106).

The present inventor identified a single Sgo1 homologue, ScSgo1 in budding yeast (ORF: YOR073W), which has so far not been analyzed. The cellular localization of ScSgo1 was examined by tagging endogenous ScSGO1 with GFP. ScSgo1-GFP was detected mainly as a single dot in proliferating cells, but only in a limited subset of the population (FIG. 8*a*). Scsgo1-GFP was not detected during the G1/S period (i.e. in cells with no bud or a small bud) but appeared as a dot in G2/M (cells with a large bud and a single nucleus) and disappeared at anaphase (cells with a large bud and a stretched nucleus) (FIG. 8*a*). The dot is co-localized with Ndc10 kinetochore protein (FIG. 8*b*). During meiosis, ScSgo1-GFP was detected at the kinetochore only at metaphase I, but never during anaphase I or meiosis II (FIG. 8*c*). Thus, the pattern of ScSgo1 localization closely resembles that of SpSgo2 in mitosis and SpSgo1 in meiosis.

The ScSGO1 gene was disrupted to examine the function of ScSgo1. Although the Scsgo1Δ cells were viable, they grew slowly and showed sensitivity to the spindle destabilizing drug benomyl (FIG. 8*d*), and indicated that centromeric function might be impaired. And then the chromosome loss rates in Scsgo1Δ cells were compared with those in wild-type cells by a colony sectoring assay. Whereas 40% of the Scsgo1Δ colonies contained red sectors (which indicate chromosome loss), less than 2% wild-type colonies contained such sectors (FIG. 8*e*). It was concluded that ScSgo1 plays a crucial role at centromeres to ensure mitotic chromosome segregation. At the onset of meiosis, Scsgo1Δ cells showed significant defects that many cells are arrested with a single nucleus in the meiotic condition. However, among the leaked tetranucleate products of meiosis, the distribution pattern of cenV-GFP was consistent with proper segregation at meiosis I with the exception of random segregation at meiosis II (FIG. 8*f*). It was also found that tagging chromosomal ScSGO1 with 13Myc at its carboxyl terminus, which by itself causes no detectable defects in mitotic growth or meiosis I, resulted in impaired segregation at meiosis II (34% non-segregation indicates 68% random segregation) (FIG. 8*g*). Moreover, the ScSGO1-Myc cells showed frequent separation of sister centromeres at late meiotic anaphase I (FIG. 8*h*), indicated that centromeric cohesion was not properly protected. Concurrently, these results support the idea that ScSgo1 plays a crucial role in protecting centromeric cohesion throughout meiosis I, and meiosis II was ensured thereby as is the case with fission yeast Sgo1.

(Conservation of Shugoshin Among Eukaryotes)

BLAST searches identified only three Sgo1-like proteins, which were all in fungi: *Schizosaccharomyces pombe* Sgo2, *Saccharomyces cerevisiae* ScSgo1, and *Neurospora crassa* B23G1.060. As the two conserved regions were found in these proteins, the related proteins are searched under conditions of two block sequences by the BLOCK MAKER and MAST programs (*Nucleic Acids Res* 26, 309-12(1998), *Bioinformatics* 14, 48-54(1998)). This approach extracted several candidate proteins from various eukaryotes including fly, worm, plant, mouse and human (see SEQ ID Nos: 21-37; *drosophila* Dm, Ce, *Arabidopsis* At, mouse Mm and human Hs, respectively, in FIG. 9). Especially, this list includes *Drosophila* ME1-S332, which is previously characterized as a protein essential for preserving centromeric cohesion in meiosis (*Cell* 83, 247-256(1995)), although the similarity score is marginal (E-value=10). All other proteins in the list show a short stretch of similarity in the carboxyl terminal basic regions, while the primary sequences in the first block are not conserved except that they all contain a putative coiled-coil. The space and sequences between these two blocks diverge among the proteins. As these blocks were previously identified to be important for ME1-S332 function (*Genes Dev.* 12, 3843-3856(1998)), the importance of the conserved regions in Sgo1 was investigated. Several amino acids were changed individually to alanines in these similarity blocks and the function of the mutant proteins in vivo was examined (FIG. 10). It was found that three conserved amino acids known to be important for ME1-S332 function were also required for Sgo1 function (13N, 34V and 368S in ME1-S332; 29N, 501 and 294S in Sgo1) (marked as arrowheads in FIG. 9). Further, other conserved amino acids in the second block (293P, 296R, 298K, 299L and 300R in Sgo1) were also all required for Sgo1 function (asterisks in FIG. 9), and non-conserved residue 297T could be changed to alanine without impairing function (circle in FIG. 9). These results indicated that the marginal structural similarity observed among *Schizosaccharomyces pombe* Sgo1 and other proteins in various eukaryotes is important. Plants and mammals carry two shugoshin-like proteins, suggesting the possibility that the function of shugoshin diverges to complete mitosis and meiosis as in fission yeast.

(Proteins Encoding Human Shugoshin Homologous Gene are Specifically Localized at Centromeres in Mitosis)

The present inventor previously identified two putative human Sgo proteins, Sgo1 and Sgo2 in the database, although their overall sequence homology to known Sgo proteins in any species other than human is marginal (FIG. 11*a*). To examine whether these proteins identified in the database are actually human Sgo homologs, the present inventor examined the localization of the proteins. For this end, the present inventor cultured rabbit polyclonal antibodies against recombinant proteins that were produced in bacteria. The obtained Sgo1 antibodies detected an up to 70 kD band (predicted molecular weight is 60 kD) in the HeLa cell extracts, and the signal was significantly reduced when cells were treated with siRNA that targets Sgo1 mRNA (FIG. 11*b*). Similarly, Sgo2 antibodies detected an up to 120 kD band (predicted molecular weight is 145 kD), the signal was reduced in extracts obtained from cells treated with Sgo2 siRNA (FIG. 11*b*). These data indicate that both Sgo1 and Sgo2 are expressed at least in proliferating HeLa cells. Next, for the purpose of analyzing proteins (SEQ ID NOs: 18 and 20, respectively hSgo1 and hSgo2) encoding human shugoshin homologous gene (SEQ ID NOs: 17 and 19) that was presumed to be human Sgo homologues, part of hSgo1 and hSgo2 was expressed in *E. coli*, and antibodies against hSgo1 and hSgo2 were produced by injecting the protein into rabbit, HeLa cells were stained with the antibodies and concurrently with tublin antibodies and DAPI, and co-stained with spindle and chromosome DNA respectively, and the expression of hSgo1 and hSgo2 proteins that were both endogenous in proliferating cells was examined. The results are shown in FIG. 12. As shown in FIG. 12, both signals of hsgo1 and hSgo2 were also observed as dots on chromosomes from prometaphase to metaphase. As a result of the immunostaining, it was identified that both proteins, hsgo1 and hSgo2 are specifically localized at centromeres at mitotic phase. Further, HeLa cells at prometaphase and metaphase were stained with antibodies against hsgo1 or hSgo2; concurrently co-stained with antibodies against centromere protein CENP-A, and DAPI; and examined the expression of hsgo1 and hSgo2 proteins. The results are shown in FIG. 13. As shown in FIG. 13, both signals of hSgo1 and hSgo2 were observed at sites close to CENP-A dots on chromosomes. As a result of the above, it was revealed that both hsgo1 and hSgo2 are centromere proteins. Further, to examine this possibility, Aurora B, which is a passenger protein of chromosome known to be localized within kinetochore from prophase to metaphase, was stained. The sites of Sgo1 and Aurora B were practically the same at prometaphase and metaphase, whereas Sgo2 was placed just outside Aurora B (see FIG. 13). As a result of the above, it was revealed that both hsgo1 and hSgo2 are placed within kinetochores from prometaphase to metaphase. Representative views of sister kinetochore are magnified on the right. Scale bar is 10 μm.

(Proteins Encoding Human Shugoshin Homologous Gene are Specifically Localized at Centromeres in Mitosis and Play an Important Role to Progress Chromosome Segregation)

RNAi experiments targeting hsgo1 and hSgo2 were performed respectively. The results are shown in FIG. 14. As a result, the expressions in any proteins were significantly suppressed 48 hours later, the cells arrested in mitosis (total, in figure) were accumulated as indicated in FIG. 14. As described above, it was strongly suggested that any protein localized at centromeres in mitosis plays an important role for progressing chromosome segregation. As the accumulation was dissolved by suppressing a spindle checkpoint factor BubR1 by RNAi, it was suggested that hsgo1 and hSgo2 are directly or indirectly function during the process where spindle properly takes the kinetochore at centromeres as described below.

Further, the cells for which RNAi experiments targeting hsgo1 was performed by using HeLa cells were mounted on a slide glass and stained with Giemsa. The results are shown in FIG. 15. It was revealed that sister chromatid at prophase strongly adhered at centromere site in control cells where RNAi was not performed; while in cells suppressing hsgo1 expression, where RNAi was performed, the adhesion was weak at centromere site, and easily detached. Consequently, it was demonstrated that hsgo1 has an important role to maintain the strong cohesion at centromere site in mitosis in proliferating cells. Mitotic cells where Sgo1 protein knockdown was performed by RNAi experiments were collected, and the chromosomes were spread to observe chromosome structure directly. In control cells, sister chromatids were resolved along the arm regions but showed the primary constriction at centromeres (FIG. 16*a* i). Amazingly, in Sgo1-depleted cells, sister chromatids were often separated along the whole chromosome length (FIG. 16*a* iii). In samples where sister chromatids stayed densely close, although sister chromatids did not indicate the primary constriction (FIG. 16*a* iv), this suggests that centromeric cohesion was lost selectively. Nocodazole treatment activates the spindle checkpoint; thereby the cell cycle is arrested at prometaphase. Such prolonged arrest in M phase causes the complete separation of the connectivity from the chromosomal arm regions. For this reason, sister chromatids are only connected at centromeres, and form 'Xshaped' chromosome (FIG. 16*b*, control). As expected, nocodazole-treatment caused the complete separation of sister chromatids along the chromosome length in Sgo1 RNAi cells (up to 97%) (FIGS. 16*c* and *d*). Consequently, it was demonstrated that hSgo1 plays an important role to maintain the strong cohesion at chromosomal centromere site in mitosis in proliferating cells.

RNAi experiments targeting Bub1 were performed respectively. The results are shown in FIG. 17. Consequently, the localization of either protein of the hsgo1 and hSgo2 to centromere was disappeared. This result means that the conclusion, "localization of shugoshin to centromere depends on Bub1 kinase", which was found in yeast by the present inventor, is also conserved in higher organisms.

Next, clone where cDNA of mouse shugoshin homologous genes (SEQ ID NOs: 21 and 23) was fused with GFP gene was produced by using retroviral vector and expressed in human HeLa cells. The results are shown in FIG. 18. Consequently, it was revealed that any of the GFP fusion proteins are also co-localized with human kinetochore protein Bub1 in mitosis.

The analysis of the above hsgo1 and hSgo2 and the analysis results obtained with the use of mouse shugoshin homologous genes were strongly suggested that shugoshin-like protein in animal cells, which were predicted from the sequence, also have functional conservation with yeast shugoshin.

INDUSTRIAL APPLICABILITY

Shugoshin of the present invention that is a regulatory factor of chromosome segregation widely conserved in eukaryotic cells, can be advantageously used for studies on the induction mechanism of cancer in somatic division, the chromosome segregation diseases such as infertility or Down's syndrome in meiotic division, and the like besides on the elucidation of mechanism in chromosome segregation.

What is claimed is:

1. A method for monitoring the regulatory activity of chromosome segregation, comprising administering a detectably-labeled monoclonal antibody, or a binding fragment thereof, that specifically recognizes human Sgo1 protein (SEQ ID NO: 18) to a cell, allowing the detectably-labeled antibody, or the binding fragment thereof, to bind to a human Sgo1 protein within the cell, monitoring the regulatory activity of chromosome segregation by following the detectably-labeled antibody in the cell.

* * * * *

SEQUENCE LISTING

```
<160> NUMBER OF SEQ ID NOS: 45

<210> SEQ ID NO 1
<211> LENGTH: 960
<212> TYPE: DNA
<213> ORGANISM: yeast

<400> SEQUENCE: 1

atgaactttc aatttataaa ttcaaatata aacaatgaag ataaattgcc gatggagtcg      60

ttgaaaaaga aatttttaaa acaaaatcgt gaaattataa aaataaatac tcagctttct     120

ataaaaatta gagaatctga aaacgaaatt caagatttga tacaagaaaa tttcactttg     180

aaaagttatt tggttaaact tgaagctcga tttcgcaatc aatctcaaac tgaggacttg     240

ttaaaaaact tctttcctga gatacaaacc attcacaaaa agatttcaca agtgcaaagt     300

ttactgaaga ttatagagaa aaagtgttca tcagatttcc tcgaagcgaa tgtaaaaagt     360

caatttacaa cctgtgaaaa taaagattcg aaagaagatt atcagatttt gcataataaa     420

cgcttggagt atgtatcatt taatgatgaa cttaaaagtc tcgaaacagg gcaaccattg     480

tattgttttc aagatttcca aaaaaaagtc catggtcctc cggctctatc tgaaaaacct     540

ggaaaatgta tattaaaaga taaaaccaat gcccacgtaa acaaaatacc acaagatgag     600

gtgaattact cattgccgca aaaaaatatc accatctttt caaaggaatt aaaagaaaac     660

gaatttgaat ccatcaacga gggcgaaact gaagaagaaa aggctaaaac atcaaatgtt     720

tgtgtttgta ttccttgtaa aagtgctgaa cagataactg accttaaagg acaagcaacc     780

ggagacagct ccccatgtga ttttgaagaa tctcaaccaa ggattaatgg acgtgaaaaa     840

ctaagacgat cagtcaaagt gataaactat gcaataccca gtttgcgaac taaactacga     900

cgagactttg acttaccatc tgatagaaaa cgcaaacgac atcccagagg caaagcataa     960

<210> SEQ ID NO 2
<211> LENGTH: 319
<212> TYPE: PRT
<213> ORGANISM: yeast

<400> SEQUENCE: 2

Met Asn Phe Gln Phe Ile Asn Ser Asn Ile Asn Asn Glu Asp Lys Leu
1               5                   10                  15

Pro Met Glu Ser Leu Lys Lys Lys Phe Leu Lys Gln Asn Arg Glu Ile
            20                  25                  30

Ile Lys Ile Asn Thr Gln Leu Ser Ile Lys Ile Arg Glu Ser Glu Asn
        35                  40                  45
```

```
Glu Ile Gln Asp Leu Ile Gln Glu Asn Phe Thr Leu Lys Ser Tyr Leu
    50                  55                  60

Val Lys Leu Glu Ala Arg Phe Arg Asn Gln Ser Gln Thr Glu Asp Leu
65                  70                  75                  80

Leu Lys Asn Phe Phe Pro Glu Ile Gln Thr Ile His Lys Lys Ile Ser
                85                  90                  95

Gln Val Gln Ser Leu Leu Lys Ile Ile Glu Lys Lys Cys Ser Ser Asp
            100                 105                 110

Phe Leu Glu Ala Asn Val Lys Ser Gln Phe Thr Thr Cys Glu Asn Lys
        115                 120                 125

Asp Ser Lys Glu Asp Tyr Gln Ile Leu His Asn Lys Arg Leu Glu Tyr
    130                 135                 140

Val Ser Phe Asn Asp Glu Leu Lys Ser Leu Glu Thr Gly Gln Pro Leu
145                 150                 155                 160

Tyr Cys Phe Gln Asp Phe Gln Lys Lys Val His Gly Pro Pro Ala Leu
                165                 170                 175

Ser Glu Lys Pro Gly Lys Cys Ile Leu Lys Asp Lys Thr Asn Ala His
            180                 185                 190

Val Asn Lys Ile Pro Gln Asp Glu Val Asn Tyr Ser Leu Pro Gln Lys
        195                 200                 205

Asn Ile Thr Ile Phe Ser Lys Glu Leu Lys Glu Asn Glu Phe Glu Ser
    210                 215                 220

Ile Asn Glu Gly Glu Thr Glu Glu Glu Lys Ala Lys Thr Ser Asn Val
225                 230                 235                 240

Cys Val Cys Ile Pro Cys Lys Ser Ala Glu Gln Ile Thr Asp Leu Lys
                245                 250                 255

Gly Gln Ala Thr Gly Asp Ser Ser Pro Cys Asp Phe Glu Glu Ser Gln
            260                 265                 270

Pro Arg Ile Asn Gly Arg Glu Lys Leu Arg Arg Ser Val Lys Val Ile
        275                 280                 285

Asn Tyr Ala Ile Pro Ser Leu Arg Thr Lys Leu Arg Arg Asp Phe Asp
    290                 295                 300

Leu Pro Ser Asp Arg Lys Arg Lys Arg His Pro Arg Gly Lys Ala
305                 310                 315


<210> SEQ ID NO 3
<211> LENGTH: 1944
<212> TYPE: DNA
<213> ORGANISM: yeast

<400> SEQUENCE: 3

atgtcgaaag catctctttc cccgaacgta gaagacttga aaaaaaagca aattcgacag      60

tataaggaaa ttatacgaat aagcaaggca caatcaatta gaattaaaga attgcagtta     120

gaaaatgaac ggttgctttc ggaaaatatc gatttgagga ctacagcgat aaacttggaa     180

gagcaactcg aaaccgtgca aaacgaaaac gaagaaaaca aaacaaagtt agctgcatta     240

cttaatcgat ttcatgaaga aacagataat tttttatcaa aattaagtct ttgtcagcaa     300

gaaatacaag acaccttcaa accagtggag gctaacttag cttacgatgt cgatacggat     360

tctgaagacc ttgacgagga atccgtcgtg aaagataccg aagaaataat tgagcaagct     420

cagcatgatg tttccttacg aaatttaagt ggaatagagg atgaaaatat aattgatgac     480

ggagaaactg ctataaatga acaaaaaaaa agagaagcta atgttttttc cgacacgcaa     540

tcagcacctc agctaaaatc cggcaaagcc ctcccagctg attttgaaaa tccttacaat     600

ctatccaatt cgaaacctgt aaataataat aatgaagata gagttgaagc ggttacttct     660
```

```
gaaaataaat ctatcgattc tgctcctcag gaaaaaaatc atgaatacga aatcgttagt     720

ccaaaatcat tatccaacaa aattaataat caagcagctg cacaaagaag aaccgaagaa     780

gataatgcaa atggagttgc tcaagaagaa aatgagggtt cacaagaagc tcattttcat     840

agcagaatac aatctgatac agtaatacaa agtacaccca ctaaacggaa atgggacgtt     900

gacattcaaa ataaacaaat taatctggct tctgcagcta ccaatgttac cggttatgta     960

tcggagaccg atagtcgccc caatcgcgca aactctttgg attctgctgt ccttcttgtg    1020

caatcttcaa ataaaagtaa ccgaaatggg catcatattt cagatcctaa tttaaatagc    1080

tccatatcgt tgaagtttgc gcctgaagat actgcgcata attcattaac ttcacaagag    1140

aatgttgggc ctcaggttac gacgacttct ctgtcaaata tgactgttgc tgaatctcct    1200

cgtacagaca ctccaaggga aataaacggg ttagtagact cttctgtcac taatgggaac    1260

gaaaaatttt ctgtagaaat aatgaatgac tctaacaaaa ttggactgaa tcctaaatct    1320

tttaccgacg aagagcggga aattttaaca ctttttcgaa atcctcccat gagactgtca    1380

agtgaacctc catcttcaaa tggattttca atagcccatc ccaataattc tccgttacgt    1440

ccgccatcgc tacaaggaat attgaatgct gaagatcgac cttacgaaat tgagccgtca    1500

cgtagctcct ttgctaccaa cgatacgggc tcctataata atttggaact tctgtcatct    1560

gtaacgaatt tgaaatcccc taatgagaac gatcgtgtga cgaaaactca gtcgcgaaga    1620

gaaacaaaag tgaaaaggcg aagaaaagct cggattcaag aaacttctga agaaagtaca    1680

gtagtcaatg agccaaatga aaaacctgat ggaaggagcc gaagggaacg gaaaaaggtt    1740

aattacgctt tgcctggatt aaggacgaaa ttaagacgga atttcgattt accttcagat    1800

catgtaaaag ctaaaaaaac gagacgtgct cctaagaact ctgagaatga ttcagctacc    1860

aaaacagaaa ccgcaaacat tacttctgaa gcacccacta cttcagaagt aacccttgaa    1920

aactccgaaa cccttaattt gtaa                                           1944
```

<210> SEQ ID NO 4
<211> LENGTH: 647
<212> TYPE: PRT
<213> ORGANISM: yeast

<400> SEQUENCE: 4

```
Met Ser Lys Ala Ser Leu Ser Pro Asn Val Glu Asp Leu Lys Lys Lys
1               5                   10                  15

Gln Ile Arg Gln Tyr Lys Glu Ile Ile Arg Ile Ser Lys Ala Gln Ser
            20                  25                  30

Ile Arg Ile Lys Glu Leu Gln Leu Glu Asn Glu Arg Leu Leu Ser Glu
        35                  40                  45

Asn Ile Asp Leu Arg Thr Thr Ala Ile Asn Leu Glu Glu Gln Leu Glu
    50                  55                  60

Thr Val Gln Asn Glu Asn Glu Glu Asn Lys Thr Lys Leu Ala Ala Leu
65                  70                  75                  80

Leu Asn Arg Phe His Glu Glu Thr Asp Asn Phe Leu Ser Lys Leu Ser
                85                  90                  95

Leu Cys Gln Gln Glu Ile Gln Asp Thr Phe Lys Pro Val Glu Ala Asn
            100                 105                 110

Leu Ala Tyr Asp Val Asp Thr Asp Ser Glu Asp Leu Asp Glu Glu Ser
        115                 120                 125

Val Val Lys Asp Thr Glu Glu Ile Ile Glu Gln Ala Gln His Asp Val
    130                 135                 140
```

```
Ser Leu Arg Asn Leu Ser Gly Ile Glu Asp Glu Asn Ile Ile Asp Asp
145                 150                 155                 160

Gly Glu Thr Ala Ile Asn Glu Gln Lys Lys Arg Glu Ala Asn Val Phe
                165                 170                 175

Ser Asp Thr Gln Ser Ala Pro Gln Leu Lys Ser Gly Lys Ala Leu Pro
            180                 185                 190

Ala Asp Phe Glu Asn Pro Tyr Asn Leu Ser Asn Ser Lys Pro Val Asn
        195                 200                 205

Asn Asn Asn Glu Asp Arg Val Glu Ala Val Thr Ser Glu Asn Lys Ser
    210                 215                 220

Ile Asp Ser Ala Pro Gln Glu Lys Asn His Glu Tyr Glu Ile Val Ser
225                 230                 235                 240

Pro Lys Ser Leu Ser Asn Lys Ile Asn Asn Gln Ala Ala Ala Gln Arg
                245                 250                 255

Arg Thr Glu Glu Asp Asn Ala Asn Gly Val Ala Gln Glu Glu Asn Glu
            260                 265                 270

Gly Ser Gln Glu Ala His Phe His Ser Arg Ile Gln Ser Asp Thr Val
        275                 280                 285

Ile Gln Ser Thr Pro Thr Lys Arg Lys Trp Asp Val Asp Ile Gln Asn
    290                 295                 300

Lys Gln Ile Asn Leu Ala Ser Ala Ala Thr Asn Val Thr Gly Tyr Val
305                 310                 315                 320

Ser Glu Thr Asp Ser Arg Pro Asn Arg Ala Asn Ser Leu Asp Ser Ala
                325                 330                 335

Val Leu Leu Val Gln Ser Ser Asn Lys Ser Asn Arg Asn Gly His His
            340                 345                 350

Ile Ser Asp Pro Asn Leu Asn Ser Ser Ile Ser Leu Lys Phe Ala Pro
        355                 360                 365

Glu Asp Thr Ala His Asn Ser Leu Thr Ser Gln Glu Asn Val Gly Pro
    370                 375                 380

Gln Val Thr Thr Thr Ser Leu Ser Asn Met Thr Val Ala Glu Ser Pro
385                 390                 395                 400

Arg Thr Asp Thr Pro Arg Glu Ile Asn Gly Leu Val Asp Ser Ser Val
                405                 410                 415

Thr Asn Gly Asn Glu Lys Phe Ser Val Glu Ile Met Asn Asp Ser Asn
            420                 425                 430

Lys Ile Gly Leu Asn Pro Lys Ser Phe Thr Asp Glu Glu Arg Glu Ile
        435                 440                 445

Leu Thr Leu Phe Arg Asn Pro Pro Met Arg Leu Ser Ser Glu Pro Pro
    450                 455                 460

Ser Ser Asn Gly Phe Ser Ile Ala His Pro Asn Asn Ser Pro Leu Arg
465                 470                 475                 480

Pro Pro Ser Leu Gln Gly Ile Leu Asn Ala Glu Asp Arg Pro Tyr Glu
                485                 490                 495

Ile Glu Pro Ser Arg Ser Ser Phe Ala Thr Asn Asp Thr Gly Ser Tyr
            500                 505                 510

Asn Asn Leu Glu Leu Leu Ser Ser Val Thr Asn Leu Lys Ser Pro Asn
        515                 520                 525

Glu Asn Asp Arg Val Thr Lys Thr Gln Ser Arg Arg Glu Thr Lys Val
    530                 535                 540

Lys Arg Arg Arg Lys Ala Arg Ile Gln Glu Thr Ser Glu Glu Ser Thr
545                 550                 555                 560

Val Val Asn Glu Pro Asn Glu Lys Pro Asp Gly Arg Ser Arg Arg Glu
                565                 570                 575
```

```
Arg Lys Lys Val Asn Tyr Ala Leu Pro Gly Leu Arg Thr Lys Leu Arg
            580                 585                 590

Arg Asn Phe Asp Leu Pro Ser Asp His Val Lys Ala Lys Lys Thr Arg
        595                 600                 605

Arg Ala Pro Lys Asn Ser Glu Asn Asp Ser Ala Thr Lys Thr Glu Thr
    610                 615                 620

Ala Asn Ile Thr Ser Glu Ala Pro Thr Thr Ser Glu Val Thr Leu Glu
625                 630                 635                 640

Asn Ser Glu Thr Leu Asn Leu
                645


<210> SEQ ID NO 5
<211> LENGTH: 1773
<212> TYPE: DNA
<213> ORGANISM: yeast

<400> SEQUENCE: 5

atgccgaaga gaaaaattgc tcctaacaag gaaagcagca ggcgtacggt ctcccacgat      60

gatttaaccc cacaaataca agaatttcaa aacctaatgg atctcgaatc gcaaaaagtg     120

gaaaacatca gacagtcgta ttcgaggcaa aactccctgc tggccaagga taactccata     180

ttaaaaatta aagttaatag cttggaaaaa aaaataagcc agctggtaca agaaaacgtg     240

actctacgat ctaaaacctc tataagcgaa gctatctaca gggaacggtt aagtaatcaa     300

ctacaagtca ttgaaaacgg tattattcaa agatttgacg aaattttta tatgtttgag      360

aacgtacgta aaaacgaaaa tttgcccagt tcgagcttaa gaacaatgtt gaagagaacg     420

agttccaggt caagatcatg ctcattgtca tcacccacat actcaaaaag ttacactagg     480

ttatcaaatc acgagaataa cctgtcgcat gaatcaagtt ttaacaagga cgatggtcca     540

gatcttgagc ctaaggctaa aaaaaggaag agttctaggc ggcaatctat gtttgtatcc     600

acgagtttag aacctgaaga cgaaaccggt gaaaacgaac ccatgatgga aaattcctct     660

gtagaggtac cggcagaatc acacgagtct gcgcaagtgg aggaaacaat agatgcctta     720

aaccctgaag aggaaaatag cgattctgtc agtaatttta ccaattcaat tatagaatac     780

tccataccag aggagaatcc gacagaaccc gagcattcat cttctaaact agaaatattc     840

aatgacagta caaatatgct aagtacagtg ccgtcaaatc ctttgccgtt gcctttacca     900

ggcccatccg caactttacc tactaccact agcgatgctt caacggtcta tccttcatca     960

agttcttcta ctaattctca tccaaagacc aaaattaagc attccatgaa gccgcctagg    1020

atagaactga agaaaaaggt tattgacgaa gtcatgcccg taagtaacat gagcagcaac    1080

agcgaaatat catttacgag aactagaaga actcgtggta aagctgtaga ttacactttg    1140

ccttctttaa gagccaaaat gaggaggcct tcagaaaaac ttgtggatgc tactactgtg    1200

attgatatac atgatctaca ggtttccaag agaaatcggg aaacttcaca taaaaggaaa    1260

agtttatccc aagattcaat acccgacgaa ccgcaattga gagaagtcgt cgtctcaaag    1320

gattatggaa ctccaaaagg gaaaaaaacg gaagatgaaa tacacgagga taccgctcat    1380

ctaatgacca cttccaacaa caacagcaac aacaaaaacg aaaaaaaact aactagcaac    1440

aatagcccta aaaaatcgtc gcctttactt gacattacaa ataaatcgga gaataagaaa    1500

aagtcaacaa gaactaaaaa attgttcaaa aatgcaattg tcaataattt atctgatgaa    1560

aattctacta cgcgaccctc caagtcgtca aagggaacca gtaataataa caacaattac    1620

aacaatttcg acaataacaa ttcaaacatt aataatgtta ataataaatc tgttagcttt    1680
```

```
agactaaatg aagatgattt agcagtattt gatttatttg gaaatggtaa ggcagtgaaa   1740

catcaaccaa aaacatatcg caccaaaaaa tga                                1773


<210> SEQ ID NO 6
<211> LENGTH: 590
<212> TYPE: PRT
<213> ORGANISM: yeast

<400> SEQUENCE: 6

Met Pro Lys Arg Lys Ile Ala Pro Asn Lys Glu Ser Ser Arg Arg Thr
1               5                   10                  15

Val Ser His Asp Asp Leu Thr Pro Gln Ile Gln Glu Phe Gln Asn Leu
            20                  25                  30

Met Asp Leu Glu Ser Gln Lys Val Glu Asn Ile Arg Gln Ser Tyr Ser
        35                  40                  45

Arg Gln Asn Ser Leu Leu Ala Lys Asp Asn Ser Ile Leu Lys Ile Lys
    50                  55                  60

Val Asn Ser Leu Glu Lys Lys Ile Ser Gln Leu Val Gln Glu Asn Val
65                  70                  75                  80

Thr Leu Arg Ser Lys Thr Ser Ile Ser Glu Ala Ile Tyr Arg Glu Arg
                85                  90                  95

Leu Ser Asn Gln Leu Gln Val Ile Glu Asn Gly Ile Ile Gln Arg Phe
            100                 105                 110

Asp Glu Ile Phe Tyr Met Phe Glu Asn Val Arg Lys Asn Glu Asn Leu
        115                 120                 125

Pro Ser Ser Ser Leu Arg Thr Met Leu Lys Arg Thr Ser Ser Arg Ser
    130                 135                 140

Arg Ser Cys Ser Leu Ser Ser Pro Thr Tyr Ser Lys Ser Tyr Thr Arg
145                 150                 155                 160

Leu Ser Asn His Glu Asn Asn Leu Ser His Glu Ser Ser Phe Asn Lys
                165                 170                 175

Asp Asp Gly Pro Asp Leu Glu Pro Lys Ala Lys Lys Arg Lys Ser Ser
            180                 185                 190

Arg Arg Gln Ser Met Phe Val Ser Thr Ser Leu Glu Pro Glu Asp Glu
        195                 200                 205

Thr Gly Glu Asn Glu Pro Met Met Glu Asn Ser Ser Val Glu Val Pro
    210                 215                 220

Ala Glu Ser His Glu Ser Ala Gln Val Glu Glu Thr Ile Asp Ala Leu
225                 230                 235                 240

Asn Pro Glu Glu Glu Asn Ser Asp Ser Val Ser Asn Phe Thr Asn Ser
                245                 250                 255

Ile Ile Glu Tyr Ser Ile Pro Glu Glu Asn Pro Thr Glu Pro Glu His
            260                 265                 270

Ser Ser Ser Lys Leu Glu Ile Phe Asn Asp Ser Thr Asn Met Leu Ser
        275                 280                 285

Thr Val Pro Ser Asn Pro Leu Pro Leu Pro Leu Pro Gly Pro Ser Ala
    290                 295                 300

Thr Leu Pro Thr Thr Thr Ser Asp Ala Ser Thr Val Tyr Pro Ser Ser
305                 310                 315                 320

Ser Ser Ser Thr Asn Ser His Pro Lys Thr Lys Ile Lys His Ser Met
                325                 330                 335

Lys Pro Pro Arg Ile Glu Leu Lys Lys Lys Val Ile Asp Glu Val Met
            340                 345                 350

Pro Val Ser Asn Met Ser Ser Asn Ser Glu Ile Ser Phe Thr Arg Thr
        355                 360                 365
```

```
Arg Arg Thr Arg Gly Lys Ala Val Asp Tyr Thr Leu Pro Ser Leu Arg
    370                 375                 380

Ala Lys Met Arg Arg Pro Ser Glu Lys Leu Val Asp Ala Thr Thr Val
385                 390                 395                 400

Ile Asp Ile His Asp Leu Gln Val Ser Lys Arg Asn Arg Glu Thr Ser
                405                 410                 415

His Lys Arg Lys Ser Leu Ser Gln Asp Ser Ile Pro Asp Glu Pro Gln
            420                 425                 430

Leu Arg Glu Val Val Val Ser Lys Asp Tyr Gly Thr Pro Lys Gly Lys
        435                 440                 445

Lys Thr Glu Asp Glu Ile His Glu Asp Thr Ala His Leu Met Thr Thr
    450                 455                 460

Ser Asn Asn Asn Ser Asn Asn Lys Asn Glu Lys Lys Leu Thr Ser Asn
465                 470                 475                 480

Asn Ser Pro Lys Lys Ser Ser Pro Leu Leu Asp Ile Thr Asn Lys Ser
                485                 490                 495

Glu Asn Lys Lys Lys Ser Thr Arg Thr Lys Lys Leu Phe Lys Asn Ala
            500                 505                 510

Ile Val Asn Asn Leu Ser Asp Glu Asn Ser Thr Thr Arg Pro Ser Lys
        515                 520                 525

Ser Ser Lys Gly Thr Ser Asn Asn Asn Asn Asn Tyr Asn Asn Phe Asp
    530                 535                 540

Asn Asn Asn Ser Asn Ile Asn Asn Val Asn Asn Lys Ser Val Ser Phe
545                 550                 555                 560

Arg Leu Asn Glu Asp Asp Leu Ala Val Phe Asp Leu Phe Gly Asn Gly
                565                 570                 575

Lys Ala Val Lys His Gln Pro Lys Thr Tyr Arg Thr Lys Lys
            580                 585                 590

<210> SEQ ID NO 7
<211> LENGTH: 2325
<212> TYPE: DNA
<213> ORGANISM: Neurospora crassa

<400> SEQUENCE: 7

atggcccgcc tcaacgaaca agccatgtcg tctgtcgcgt tgtcaacaga caatctcgag      60

ctcctgcgta ggaagttcct cagacaaaac agagatattg ctcgagtcaa ttccacacag     120

tcactccgta tccgtgggtt ggagaatgaa tgcgctcgtt tgctgtcgga aaacctcgaa     180

ctccgtggtc aggtcttgcg cctcgaaaag gagctccaag acaacgctgc gcgaagggtg     240

gccgatcatg cgctcgaggt caaggccaag atggagacgc agttggcgga actcagttcg     300

ctgctggcaa gcttagggga gccgccctcg aagcggcgcc tttcagaaga gaggcgatac     360

gcgcagcctc gaccgagcgt tcaccggagc cctcccttac gaagagcacg ccaggaggcc     420

gaccaggaac tactggctga gcaggaagga aggctaccgc cgatatacga gaacaagacg     480

tatgcgcgag ccacaatgaa cagtgaagaa atcctggcgc tgtgcatgca ggcagacgat     540

tcgaatgact cgccagatat cggaccgccg ccagtatcta ggtttgtcga ggatgatatg     600

gtcatacctt gttcaccatc gccaaacaag aacgccgagg ctgaagaaac ggaaactacc     660

gagcaagtgg aagagagccc tagggctctt caagtaccgc cgtcattatc gccgcctaaa     720

ctggactacg acaggagacc aaacatgatc ctattcagcc cacccaaaga atcgagagtg     780

gcagaaccct ccaaaatgtt cagtccccct ccgatggaac caccgaaaca gtccacatcg     840

gctgtaccga gtgagacaat acgagcaggc ctcaagcgaa agttgaacgg cgacaaccaa     900
```

```
aacgaaccca acaaggcaac caagcttcaa caaggaaagg agaatggcaa tgagactggg    960
atcaagaaag gactctctgc ccgcgacccg cacaagagga aaagcatcaa agagaccgca   1020
acgaaaccga gagccccgct gtcagcaaag agcacgaacg agcacattgt ctctccgaag   1080
aagccggcga agccccacca agtggccgac gattttaagc cggtgaaggt gcacaaggcg   1140
tcaaagggta aagagaaagt cgacctgccc gctccggaca agaagtcagc agtagaagaa   1200
acgcaaggaa attctacgtc ggcattcacg aaagtcgaga tcctcccgcc ggctctggaa   1260
cctactcctg aagttgcaga gattcctgaa accgatattc tgatcacacc tggaacacca   1320
gagcgcgcct ctgaaagcac tgttgtgacc cacgataccc cgccgccagc ccacatttca   1380
tccaatggag agacgtcgcg gcctagcagg cgtgctagag cggctatcag ctatacagag   1440
cccaatctgc gcgacaagat gcgacgaccg accaaagagc tctttgatgc cgtttctggg   1500
gagggcaagt tcctacacag gccgacatcg caacagcaac agcagcaacg caagggcgac   1560
gagtcagcac cgacgtcagt tagcaaggtc aaggtcgagc catcgccggc ggtggatata   1620
agtagtctga ccagcagtgc gctgtttgaa aaagagaagg agaaggaacc acagccggat   1680
gaaggaatat tatctccaaa cggcatcctc ccaagctcag tagacctggg aaggagaaga   1740
cgcgcctcat ccttctctac tgcagcccct gcaatgacaa ttccttcggt ccaagaacaa   1800
tcaactctaa acctcccagc cgcggacgag accgatgaaa acgccgcggt cgaggctcag   1860
attcagaagg agctgagtaa tagtattaca acacggccca ggggtggaaa ggggaggcaa   1920
tcaatgagcc gttccgtacc cacgatccca acagaaaatt acgagcacga ggacgcacaa   1980
ctctcgacga actcagcctc ggtggatctt tacgactttg ctagttgtgc gtctccggat   2040
agcgcagcac cccagctaga agcgactacc ggcgatgttc ctgttaataa gaaggcaccc   2100
aaaggttcaa gaagagcgtc ctcagctgct tcgaccgaga caacagcaac agcatccgca   2160
aagccaagat cttcccgaaa aagggcttcg atgctggtgc cgaagaaaag cttgtgggct   2220
gaagagttag cgcaggagga agaggatgag gaagatgtcg gcaatgacag tggcgggtcc   2280
ttgtccaagg ggagggcctc gaggaggaga agcatgatgc tttga                   2325
```

<210> SEQ ID NO 8
<211> LENGTH: 774
<212> TYPE: PRT
<213> ORGANISM: Neurospora crassa

<400> SEQUENCE: 8

```
Met Ala Arg Leu Asn Glu Gln Ala Met Ser Ser Val Ala Leu Ser Thr
1               5                   10                  15

Asp Asn Leu Glu Leu Leu Arg Arg Lys Phe Leu Arg Gln Asn Arg Asp
            20                  25                  30

Ile Ala Arg Val Asn Ser Thr Gln Ser Leu Arg Ile Arg Gly Leu Glu
        35                  40                  45

Asn Glu Cys Ala Arg Leu Leu Ser Glu Asn Leu Glu Leu Arg Gly Gln
    50                  55                  60

Val Leu Arg Leu Glu Lys Glu Leu Gln Asp Asn Ala Ala Arg Arg Val
65                  70                  75                  80

Ala Asp His Ala Leu Glu Val Lys Ala Lys Met Glu Thr Gln Leu Ala
                85                  90                  95

Glu Leu Ser Ser Leu Leu Ala Ser Leu Gly Glu Pro Pro Ser Lys Arg
            100                 105                 110

Arg Leu Ser Glu Glu Arg Arg Tyr Ala Gln Pro Arg Pro Ser Val His
        115                 120                 125
```

```
Arg Ser Pro Pro Leu Arg Arg Ala Arg Gln Glu Ala Asp Gln Glu Leu
    130                 135                 140

Leu Ala Glu Gln Glu Gly Arg Leu Pro Pro Ile Tyr Glu Asn Lys Thr
145                 150                 155                 160

Tyr Ala Arg Ala Thr Met Asn Ser Glu Glu Ile Leu Ala Leu Cys Met
                165                 170                 175

Gln Ala Asp Asp Ser Asn Asp Ser Pro Asp Ile Gly Pro Pro Pro Val
            180                 185                 190

Ser Arg Phe Val Glu Asp Asp Met Val Ile Pro Cys Ser Pro Ser Pro
        195                 200                 205

Asn Lys Asn Ala Glu Ala Glu Glu Thr Glu Thr Thr Glu Gln Val Glu
    210                 215                 220

Glu Ser Pro Arg Ala Leu Gln Val Pro Pro Ser Leu Ser Pro Pro Lys
225                 230                 235                 240

Leu Asp Tyr Asp Arg Arg Pro Asn Met Ile Leu Phe Ser Pro Pro Lys
                245                 250                 255

Glu Ser Arg Val Ala Glu Pro Ser Lys Met Phe Ser Pro Pro Pro Met
            260                 265                 270

Glu Pro Pro Lys Gln Ser Thr Ser Ala Val Pro Ser Glu Thr Ile Arg
        275                 280                 285

Ala Gly Leu Lys Arg Lys Leu Asn Gly Asp Asn Gln Asn Glu Pro Asn
    290                 295                 300

Lys Ala Thr Lys Leu Gln Gln Gly Lys Glu Asn Gly Asn Glu Thr Gly
305                 310                 315                 320

Ile Lys Lys Gly Leu Ser Ala Arg Asp Pro His Lys Arg Lys Ser Ile
                325                 330                 335

Lys Glu Thr Ala Thr Lys Pro Arg Ala Pro Leu Ser Ala Lys Ser Thr
            340                 345                 350

Asn Glu His Ile Val Ser Pro Lys Lys Pro Ala Lys Pro His Gln Val
        355                 360                 365

Ala Asp Asp Phe Lys Pro Val Lys Val His Lys Ala Ser Lys Gly Lys
    370                 375                 380

Glu Lys Val Asp Leu Pro Ala Pro Asp Lys Lys Ser Ala Val Glu Glu
385                 390                 395                 400

Thr Gln Gly Asn Ser Thr Ser Ala Phe Thr Lys Val Glu Ile Leu Pro
                405                 410                 415

Pro Ala Leu Glu Pro Thr Pro Glu Val Ala Glu Ile Pro Glu Thr Asp
            420                 425                 430

Ile Leu Ile Thr Pro Gly Thr Pro Glu Arg Ala Ser Glu Ser Thr Val
        435                 440                 445

Val Thr His Asp Thr Pro Pro Pro Ala His Ile Ser Ser Asn Gly Glu
    450                 455                 460

Thr Ser Arg Pro Ser Arg Arg Ala Arg Ala Ala Ile Ser Tyr Thr Glu
465                 470                 475                 480

Pro Asn Leu Arg Asp Lys Met Arg Arg Pro Thr Lys Glu Leu Phe Asp
                485                 490                 495

Ala Val Ser Gly Glu Gly Lys Phe Leu His Arg Pro Thr Ser Gln Gln
            500                 505                 510

Gln Gln Gln Gln Arg Lys Gly Asp Glu Ser Ala Pro Thr Ser Val Ser
        515                 520                 525

Lys Val Lys Val Glu Pro Ser Pro Ala Val Asp Ile Ser Ser Leu Thr
    530                 535                 540

Ser Ser Ala Leu Phe Glu Lys Glu Lys Glu Lys Glu Pro Gln Pro Asp
```

```
545                 550                 555                 560

Glu Gly Ile Leu Ser Pro Asn Gly Ile Leu Pro Ser Ser Val Asp Leu
                565                 570                 575

Gly Arg Arg Arg Arg Ala Ser Ser Phe Ser Thr Ala Ala Pro Ala Met
            580                 585                 590

Thr Ile Pro Ser Val Gln Glu Gln Ser Thr Leu Asn Leu Pro Ala Ala
        595                 600                 605

Asp Glu Thr Asp Glu Asn Ala Ala Val Glu Ala Gln Ile Gln Lys Glu
    610                 615                 620

Leu Ser Asn Ser Ile Thr Thr Arg Pro Arg Gly Gly Lys Gly Arg Gln
625                 630                 635                 640

Ser Met Ser Arg Ser Val Pro Thr Ile Pro Thr Glu Asn Tyr Glu His
                645                 650                 655

Glu Asp Ala Gln Leu Ser Thr Asn Ser Ala Ser Val Asp Leu Tyr Asp
            660                 665                 670

Phe Ala Ser Cys Ala Ser Pro Asp Ser Ala Ala Pro Gln Leu Glu Ala
        675                 680                 685

Thr Thr Gly Asp Val Pro Val Asn Lys Lys Ala Pro Lys Gly Ser Arg
    690                 695                 700

Arg Ala Ser Ser Ala Ala Ser Thr Glu Thr Thr Ala Thr Ala Ser Ala
705                 710                 715                 720

Lys Pro Arg Ser Ser Arg Lys Arg Ala Ser Met Leu Val Pro Lys Lys
                725                 730                 735

Ser Leu Trp Ala Glu Glu Leu Ala Gln Glu Glu Glu Asp Glu Glu Asp
            740                 745                 750

Val Gly Asn Asp Ser Gly Gly Ser Leu Ser Lys Gly Arg Ala Ser Arg
        755                 760                 765

Arg Arg Ser Met Met Leu
    770
```

<210> SEQ ID NO 9
<211> LENGTH: 1671
<212> TYPE: DNA
<213> ORGANISM: Arabidopsis thaliana

<400> SEQUENCE: 9

```
atggttcgag cgacggttct gaatgtcggt gatcacgcca gtgaaggtgt gcgtactaac      60

aaagctaaag gagagaaaat ggttctggaa cctccgatga acagtgcaca aagacgaaag     120

ttgggggata ttactaattt gcagaatcag aagaatctaa tgaatcaggg agcgaagcat     180

cagcaacaag ctatattaat ctcttctaaa gaaaacgctg aaaatcttca aaaggcactg     240

agaaattctt ctgaaaacac aaagctgatg aaagtcgtca tggagagaga tggaatcaaa     300

agtgatctga agaaacttag gattgaattt cagaaggttc aagaacagaa tttgctactt     360

gcccaggcta acactcgtat cttggcgctg aaggtacttc agcacgaact tggttgcaag     420

aatgggttag tcatggccag gaaaatgctg cttaaggctc aagcaaatgc ttgtggtggg     480

gcttgcaaaa cctttcagcc aaatgatgca gatcatgagc atgcttccgg gagctccaac     540

gctaactcat tgcaaagaaa tgagaaagcc aacagtaaaa ggagagtttc tggaaggaag     600

aatcccgcca attccgaggt attagatata attggcagat cgggagagac atgtcagatg     660

gaagacaaca ttgacaacaa gaagttggtc tctgatagtg acaatgatgc tgaaaaccat     720

ataaatgaca atgtccaaag caaaagatat tgtgcaggaa gacagagtag cagttctaag     780

actcgagaag ccagccaaac agaaaccttg caaaaggtgg ttgacgccaa agaaattaag     840
```

```
ggggatgcaa ggttttcttt gacaaagcat tctgactggt taaaatctca agaacctgag    900

ccatctgaaa gcctatacga gtcaaggttc cctttgagaa ggcgttctgc ccggttaaaa    960

tctcaagaac ctgagccatc tgaaagcttc catgactcaa tagagacaac caagaggagg   1020

aggtcggcaa taaggtctgc tatgtttaat atccaagagc tgggcgttat tcaaaacttg   1080

aacggtttac ctgatgatca agagattgct gcaaaggcca gatgctctgc acgtgaacag   1140

tctaccgggt ctaaacccga agcagtagaa ccacatgaca caaaagagat aatcgggaaa   1200

agcaggatat ctttgagaag acagtctgcg aggtttaatt tccaagagct gggcgtgact   1260

gaaaacttga atggtccaca tgatgatcaa acgattgctg caaatgccag atgctgtgca   1320

agtgaacagt ctatcgggtc taaacccgaa gcagtagaac cacatgacat tgaagagaga   1380

atcgggaaaa tcagagtctc ttcaagaaga caatctgcaa acattgaaac tccgagagcc   1440

atcaaagaac ctgcaaatcc gcctttgcat gatgacaatg ttgaggagtc tagtcagata   1500

tcatgttcag tttcaatgga gcttaaaaga gaatcaaaga agaaaccaac aggcgacgaa   1560

tcagaggaaa tgagaaaaac aactgttgga agaccttcaa ggcaagctgc tgaaaaaatc   1620

aaatcgtaca aggaaccttc acttaaggag aagatgcgag gggcttctg a             1671
```

<210> SEQ ID NO 10
<211> LENGTH: 556
<212> TYPE: PRT
<213> ORGANISM: Arabidopsis thaliana

<400> SEQUENCE: 10

```
Met Val Arg Ala Thr Val Leu Asn Val Gly Asp His Ala Ser Glu Gly
1               5                   10                  15

Val Arg Thr Asn Lys Ala Lys Gly Glu Lys Met Val Leu Glu Pro Pro
            20                  25                  30

Met Asn Ser Ala Gln Arg Arg Lys Leu Gly Asp Ile Thr Asn Leu Gln
        35                  40                  45

Asn Gln Lys Asn Leu Met Asn Gln Gly Ala Lys His Gln Gln Gln Ala
    50                  55                  60

Ile Leu Ile Ser Ser Lys Glu Asn Ala Glu Asn Leu Gln Lys Ala Leu
65                  70                  75                  80

Arg Asn Ser Ser Glu Asn Thr Lys Leu Met Lys Val Val Met Glu Arg
                85                  90                  95

Asp Gly Ile Lys Ser Asp Leu Lys Lys Leu Arg Ile Glu Phe Gln Lys
            100                 105                 110

Val Gln Glu Gln Asn Leu Leu Leu Ala Gln Ala Asn Thr Arg Ile Leu
        115                 120                 125

Ala Leu Lys Val Leu Gln His Glu Leu Gly Cys Lys Asn Gly Leu Val
    130                 135                 140

Met Ala Arg Lys Met Leu Leu Lys Ala Gln Ala Asn Ala Cys Gly Gly
145                 150                 155                 160

Ala Cys Lys Thr Phe Gln Pro Asn Asp Ala Asp His Glu His Ala Ser
                165                 170                 175

Gly Ser Ser Asn Ala Asn Ser Leu Gln Arg Asn Glu Lys Ala Asn Ser
            180                 185                 190

Lys Arg Arg Val Ser Gly Arg Lys Asn Pro Ala Asn Ser Glu Val Leu
        195                 200                 205

Asp Ile Ile Gly Arg Ser Gly Glu Thr Cys Gln Met Glu Asp Asn Ile
    210                 215                 220

Asp Asn Lys Lys Leu Val Ser Asp Ser Asp Asn Asp Ala Glu Asn His
225                 230                 235                 240
```

```
Ile Asn Asp Asn Val Gln Ser Lys Arg Tyr Cys Ala Gly Arg Gln Ser
                245                 250                 255

Ser Ser Ser Lys Thr Arg Glu Ala Ser Gln Thr Glu Thr Leu Gln Lys
            260                 265                 270

Val Val Asp Ala Lys Glu Ile Lys Gly Asp Ala Arg Phe Ser Leu Thr
        275                 280                 285

Lys His Ser Asp Trp Leu Lys Ser Gln Glu Pro Glu Pro Ser Glu Ser
    290                 295                 300

Leu Tyr Glu Ser Arg Phe Pro Leu Arg Arg Arg Ser Ala Arg Leu Lys
305                 310                 315                 320

Ser Gln Glu Pro Glu Pro Ser Glu Ser Phe His Asp Ser Ile Glu Thr
                325                 330                 335

Thr Lys Arg Arg Arg Ser Ala Ile Arg Ser Ala Met Phe Asn Ile Gln
            340                 345                 350

Glu Leu Gly Val Ile Gln Asn Leu Asn Gly Leu Pro Asp Asp Gln Glu
        355                 360                 365

Ile Ala Ala Lys Ala Arg Cys Ser Ala Arg Glu Gln Ser Thr Gly Ser
    370                 375                 380

Lys Pro Glu Ala Val Glu Pro His Asp Thr Lys Glu Ile Ile Gly Lys
385                 390                 395                 400

Ser Arg Ile Ser Leu Arg Arg Gln Ser Ala Arg Phe Asn Phe Gln Glu
                405                 410                 415

Leu Gly Val Thr Glu Asn Leu Asn Gly Pro His Asp Asp Gln Thr Ile
            420                 425                 430

Ala Ala Asn Ala Arg Cys Cys Ala Ser Glu Gln Ser Ile Gly Ser Lys
        435                 440                 445

Pro Glu Ala Val Glu Pro His Asp Ile Glu Glu Arg Ile Gly Lys Ile
    450                 455                 460

Arg Val Ser Ser Arg Arg Gln Ser Ala Asn Ile Glu Thr Pro Arg Ala
465                 470                 475                 480

Ile Lys Glu Pro Ala Asn Pro Pro Leu His Asp Asp Asn Val Glu Glu
                485                 490                 495

Ser Ser Gln Ile Ser Cys Ser Val Ser Met Glu Leu Lys Arg Glu Ser
            500                 505                 510

Lys Lys Lys Pro Thr Gly Asp Glu Ser Glu Glu Met Arg Lys Thr Thr
        515                 520                 525

Val Gly Arg Pro Ser Arg Gln Ala Ala Glu Lys Ile Lys Ser Tyr Lys
    530                 535                 540

Glu Pro Ser Leu Lys Glu Lys Met Arg Gly Gly Phe
545                 550                 555


<210> SEQ ID NO 11
<211> LENGTH: 1341
<212> TYPE: DNA
<213> ORGANISM: Arabidopsis thaliana

<400> SEQUENCE: 11

atggataaag aagagacgca gcagaaggaa aatatgctat tctcttccca ggaatatgct      60

gcaaagcttc aaaaggcatt tcctcttcac tttaatcttg aaaacatgac actgatgaaa     120

gctctagcac accgaaataa actcgtcgag ttgagcggta ttgagattca gaaactgagg     180

attaacttac ggagtgtgca ggaaaagaat ttgcagcttg ctcaggcaaa cagtcagatg     240

ttagcgctca aggatctcca gcatgaactt ggctgcaaga atgctttact taaagtcaag     300

aaacatcttg aggagcaagt acttccacgt acacatcatg aatcgaaaga caaggtttca     360
```

```
gcaagcgctt ctgatgggga ttgcaaatcc tttcaggtgc atgacataaa acataaagat    420

accaagagaa agcgaacaac aaggataaaa tcttcagtaa gtgccgacgt caagccaata    480

cctgtgaatg attctaacag taaagctaac cgtaaaagaa gagtttctgg agtaatagat    540

actactggta ttcccgaaga gatctgtcag actgaagatg acattgataa gggggttgtc    600

tctcgagggg taaaccaaga tattgacaat gttgtcaaca agaagtttgt tcctgatgca    660

gcaaacccgg taaaagagag tgtgcatcgc aagaggcaat gtacacgaag gcaatctacc    720

agatttgatg ttcaagaaac taaacaaacg gaaaagttgc ttgagatgga tggtgccaaa    780

gaaagtaaag aaaccgcaag cttctctttg agaagacggt ctgctcggtt aaggcacgaa    840

gaagctgaac catgtaaaag cttacatgag ggagacgaag tcagggagac aatcaagagg    900

agaagagtct ctttaagact gtctgcaagg tttgatatac aagaaccgca tgtgactgaa    960

acctcgaatg ctgacgatgc aagaagcata gtaatcgaag aatctgctgg atcaagatcg   1020

gaatctgtag aaccatccga aagcaggcat gaaacaaaag agataacccg gaaacgcagt   1080

ttctcaacga gaagacaatc aacaaagggt aaatctcaaa ccgatgaagc cattaaagaa   1140

atagcgacag acccatcttt ggtcaacacc atagttcaag agtgtgatca ggaaacagaa   1200

tcaaaggata agcctaaagc tgatgaaaac gaagggatga caagaagatc atctgtggga   1260

agaccatcga gacatgccgc agagaaagtc caatcataca gagaagtctc acttagagta   1320

aagatgcgac gaaaatgcta a                                              1341
```

<210> SEQ ID NO 12
<211> LENGTH: 446
<212> TYPE: PRT
<213> ORGANISM: Arabidopsis thaliana

<400> SEQUENCE: 12

```
Met Asp Lys Glu Glu Thr Gln Gln Lys Glu Asn Met Leu Phe Ser Ser
1               5                   10                  15

Gln Glu Tyr Ala Ala Lys Leu Gln Lys Ala Phe Pro Leu His Phe Asn
            20                  25                  30

Leu Glu Asn Met Thr Leu Met Lys Ala Leu Ala His Arg Asn Lys Leu
        35                  40                  45

Val Glu Leu Ser Gly Ile Glu Ile Gln Lys Leu Arg Ile Asn Leu Arg
    50                  55                  60

Ser Val Gln Glu Lys Asn Leu Gln Leu Ala Gln Ala Asn Ser Gln Met
65                  70                  75                  80

Leu Ala Leu Lys Asp Leu Gln His Glu Leu Gly Cys Lys Asn Ala Leu
                85                  90                  95

Leu Lys Val Lys Lys His Leu Glu Glu Gln Val Leu Pro Arg Thr His
            100                 105                 110

His Glu Ser Lys Asp Lys Val Ser Ala Ser Ala Ser Asp Gly Asp Cys
        115                 120                 125

Lys Ser Phe Gln Val His Asp Ile Lys His Lys Asp Thr Lys Arg Lys
    130                 135                 140

Arg Thr Thr Arg Ile Lys Ser Ser Val Ser Ala Asp Val Lys Pro Ile
145                 150                 155                 160

Pro Val Asn Asp Ser Asn Ser Lys Ala Asn Arg Lys Arg Arg Val Ser
                165                 170                 175

Gly Val Ile Asp Thr Thr Gly Ile Pro Glu Glu Ile Cys Gln Thr Glu
            180                 185                 190

Asp Asp Ile Asp Lys Gly Val Val Ser Arg Gly Val Asn Gln Asp Ile
```

```
        195                 200                 205

Asp Asn Val Val Asn Lys Lys Phe Val Pro Asp Ala Ala Asn Pro Val
    210                 215                 220

Lys Glu Ser Val His Arg Lys Arg Gln Cys Thr Arg Arg Gln Ser Thr
225                 230                 235                 240

Arg Phe Asp Val Gln Glu Thr Lys Gln Thr Glu Lys Leu Leu Glu Met
                245                 250                 255

Asp Gly Ala Lys Glu Ser Lys Glu Thr Ala Ser Phe Ser Leu Arg Arg
            260                 265                 270

Arg Ser Ala Arg Leu Arg His Glu Glu Ala Glu Pro Cys Lys Ser Leu
        275                 280                 285

His Glu Gly Asp Glu Val Arg Glu Thr Ile Lys Arg Arg Arg Val Ser
    290                 295                 300

Leu Arg Leu Ser Ala Arg Phe Asp Ile Gln Glu Pro His Val Thr Glu
305                 310                 315                 320

Thr Ser Asn Ala Asp Asp Ala Arg Ser Ile Val Ile Glu Glu Ser Ala
                325                 330                 335

Gly Ser Arg Ser Glu Ser Val Glu Pro Ser Glu Ser Arg His Glu Thr
            340                 345                 350

Lys Glu Ile Thr Arg Lys Arg Ser Phe Ser Thr Arg Arg Gln Ser Thr
        355                 360                 365

Lys Gly Lys Ser Gln Thr Asp Glu Ala Ile Lys Glu Ile Ala Thr Asp
    370                 375                 380

Pro Ser Leu Val Asn Thr Ile Val Gln Glu Cys Asp Gln Glu Thr Glu
385                 390                 395                 400

Ser Lys Asp Lys Pro Lys Ala Asp Glu Asn Glu Gly Met Thr Arg Arg
                405                 410                 415

Ser Ser Val Gly Arg Pro Ser Arg His Ala Ala Glu Lys Val Gln Ser
            420                 425                 430

Tyr Arg Glu Val Ser Leu Arg Val Lys Met Arg Arg Lys Cys
        435                 440                 445
```

<210> SEQ ID NO 13
<211> LENGTH: 1554
<212> TYPE: DNA
<213> ORGANISM: mouse

<400> SEQUENCE: 13

```
atggctaagg aaaggtgtca gaaaaggtcc tttcaagata cccttgaaga cattaagaat     60

cgaatgaaag aaaaaaggaa taaaaatttg gcggggattg ggaaacgcaa gtcctttatt    120

gttgcaccgg gccaagtacc cactaacact gctacactac tgagatatta ccaagataac    180

aacaggttgt tagtcttggc tttggaaaat gagaaatcca aagtgagaga agcacaggat    240

gtcatcctgc aactgagaaa agaatgctac taccttactt gtcagctgta tgcattgaaa    300

gagaagctaa cttcccgaca aagtgaagaa actactcaga actggaaagg acgtccctca    360

gacgtggtct ccagcattga caatacgacc agggacttgt cagggaagtc cttacagcaa    420

attgctgttg aagaaactga ttgtccttac caaaccacag aaccaagtcc tgctgttact    480

ccagagacac agggttgcga ttttgattca ggtaaagttg agtctactga tgaagtctta    540

cccagaacta tatctatccg tcgccattta aggaaagatt ttagtaatat aagccactcc    600

acgactttgg aggattgtaa agccagtcca agagtggcac agtctctgga agttaaagga    660

agtagatgta gagaagtaac cgtaaccctg cacagacttg aaaatgtttg tctgtggaac    720

aaagaccaaa ttagcttatg ttctagactg attaacccag caaagattac tgaaacagaa    780
```

```
gtcattttat catctaaacc tgaacaaata gaaagcaagc ataaacgtgc acgaaaaaga    840

agagcagagc aaagaagaac caagcagaga tgcaaatcaa aatcctcatt gaggagtaag    900

gggaacaaaa acaaagataa gcagggttta ccccctacta cactggatgg aggtattggt    960

tcctgtgatg cttacgattt taatctaaaa gggacggtcc accccacccc tttccgacaa   1020

aaaatgaaca atggctgcaa caaagaaacg gatagcagca actcagaagt gagtgacctc   1080

gaatgcagta cctctgagga tgagtctgat gacctctacc tgcctccctc caagcgcttg   1140

cgagactaca gagagtcaga gagagcagtt accaggcctc ggtctaaaag aggacttcag   1200

tacccagatg ggaaagagag gaaggaggtg ctgccatcta cagctcctac tggtatccca   1260

cctgagactc aagagtcacc tcgttgtagc ctaaaggatg tcaccaatat cctgcagtgt   1320

cctagagtga agatcaggaa gccttctctg cctccaaagc ggcgtgaaga cagcccagca   1380

gtggctctga ctaaacgcag gtgtagcacc atcaaaagct ataaagagcc aacactcgct   1440

tcaaagctaa gaagagggga ccctttcacg gacttgtgtt tcttgaattc tcctattttc   1500

aagcagaaaa ggggtatgag atgtcctaaa agaagaacca agcaaacaca gtaa         1554
```

```
<210> SEQ ID NO 14
<211> LENGTH: 517
<212> TYPE: PRT
<213> ORGANISM: mosue

<400> SEQUENCE: 14

Met Ala Lys Glu Arg Cys Gln Lys Arg Ser Phe Gln Asp Thr Leu Glu
1               5                   10                  15

Asp Ile Lys Asn Arg Met Lys Glu Lys Arg Asn Lys Asn Leu Ala Gly
            20                  25                  30

Ile Gly Lys Arg Lys Ser Phe Ile Val Ala Pro Gly Gln Val Pro Thr
        35                  40                  45

Asn Thr Ala Thr Leu Leu Arg Tyr Tyr Gln Asp Asn Asn Arg Leu Leu
    50                  55                  60

Val Leu Ala Leu Glu Asn Glu Lys Ser Lys Val Arg Glu Ala Gln Asp
65                  70                  75                  80

Val Ile Leu Gln Leu Arg Lys Glu Cys Tyr Tyr Leu Thr Cys Gln Leu
                85                  90                  95

Tyr Ala Leu Lys Glu Lys Leu Thr Ser Arg Gln Ser Glu Glu Thr Thr
            100                 105                 110

Gln Asn Trp Lys Gly Arg Pro Ser Asp Val Val Ser Ser Ile Asp Asn
        115                 120                 125

Thr Thr Arg Asp Leu Ser Gly Lys Ser Leu Gln Gln Ile Ala Val Glu
    130                 135                 140

Glu Thr Asp Cys Pro Tyr Gln Thr Thr Glu Pro Ser Pro Ala Val Thr
145                 150                 155                 160

Pro Glu Thr Gln Gly Cys Asp Phe Asp Ser Gly Lys Val Glu Ser Thr
                165                 170                 175

Asp Glu Val Leu Pro Arg Thr Ile Ser Ile Arg Arg His Leu Arg Lys
            180                 185                 190

Asp Phe Ser Asn Ile Ser His Ser Thr Thr Leu Glu Asp Cys Lys Ala
        195                 200                 205

Ser Pro Arg Val Ala Gln Ser Leu Glu Val Lys Gly Ser Arg Cys Arg
    210                 215                 220

Glu Val Thr Val Thr Leu His Arg Leu Glu Asn Val Cys Leu Trp Asn
225                 230                 235                 240
```

```
Lys Asp Gln Ile Ser Leu Cys Ser Arg Leu Ile Asn Pro Ala Lys Ile
                245                 250                 255

Thr Glu Thr Glu Val Ile Leu Ser Ser Lys Pro Glu Gln Ile Glu Ser
            260                 265                 270

Lys His Lys Arg Ala Arg Lys Arg Arg Ala Glu Gln Arg Arg Thr Lys
        275                 280                 285

Gln Arg Cys Lys Ser Lys Ser Ser Leu Arg Ser Lys Gly Asn Lys Asn
    290                 295                 300

Lys Asp Lys Gln Gly Leu Pro Pro Thr Thr Leu Asp Gly Gly Ile Gly
305                 310                 315                 320

Ser Cys Asp Ala Tyr Asp Phe Asn Leu Lys Gly Thr Val His Pro Thr
                325                 330                 335

Pro Phe Arg Gln Lys Met Asn Asn Gly Cys Asn Lys Glu Thr Asp Ser
            340                 345                 350

Ser Asn Ser Glu Val Ser Asp Leu Glu Cys Ser Thr Ser Glu Asp Glu
        355                 360                 365

Ser Asp Asp Leu Tyr Leu Pro Pro Ser Lys Arg Leu Arg Asp Tyr Arg
    370                 375                 380

Glu Ser Glu Arg Ala Val Thr Arg Pro Arg Ser Lys Arg Gly Leu Gln
385                 390                 395                 400

Tyr Pro Asp Gly Lys Glu Arg Lys Glu Val Leu Pro Ser Thr Ala Pro
                405                 410                 415

Thr Gly Ile Pro Pro Glu Thr Gln Glu Ser Pro Arg Cys Ser Leu Lys
            420                 425                 430

Asp Val Thr Asn Ile Leu Gln Cys Pro Arg Val Lys Ile Arg Lys Pro
        435                 440                 445

Ser Leu Pro Pro Lys Arg Arg Glu Asp Ser Pro Ala Val Ala Leu Thr
    450                 455                 460

Lys Arg Arg Cys Ser Thr Ile Lys Ser Tyr Lys Glu Pro Thr Leu Ala
465                 470                 475                 480

Ser Lys Leu Arg Arg Gly Asp Pro Phe Thr Asp Leu Cys Phe Leu Asn
                485                 490                 495

Ser Pro Ile Phe Lys Gln Lys Arg Gly Met Arg Cys Pro Lys Arg Arg
            500                 505                 510

Thr Lys Gln Thr Gln
        515
```

```
<210> SEQ ID NO 15
<211> LENGTH: 3495
<212> TYPE: DNA
<213> ORGANISM: mouse

<400> SEQUENCE: 15

atggagtacc cagggataaa agttgacact gttacctctg gaattcagag acgagtgaag      60

ggcagaattg caaagacaaa tttgaatgtt tctcttgctt caaagatcaa agcaaaaata     120

ttaaacaatt cttctatttt caagatctct ctaaagcaca acaacagagc attagcgcgg     180

gcccttagta aagagaaaga gaattctcga agaattacta ccgaaaagat gcaattacag     240

aaagaagtag agaaactgaa ttttgagaat acctttcttc gcttaaagtt aaataccttg     300

aataagaagc ttgtagaaat agaatcgcat gtgagcaatg atttgttaac tgcaattgaa     360

ataagcagtc tttctgagtt ccaccaaggt tcttttctcc tgtcagctac caagaaacaa     420

aggaacagta agcagtgcaa gcctgcgcat cttccatatg caagagttct gttaacttca     480

gaaaatgatg atgatgatgg tgctgatgat aaatggcaga caaagtgtaa caacagaact     540
```

-continued

```
atatcaaaga cctcacctga tagtacctct tcagtatcaa gacaaccttc atccttacat    600
cagtgcaatt tgaaagcatt ccctcctaaa gaagataatc agaagacatg tgggtcaggt    660
catttagaac atacttcaag tgttgatata cttcctaatg agagccactc agatcaaagt    720
cctaagagtt ctctgagtga gatgaaaact gctccatctc ccagcctcag aagggaaaaa    780
ttatcacatg gtaatgtgac tatgaggaag aagtgtgtgt cttcaactcc agacattctg    840
tatgtgacag atttagatca ccaaccaact tcaagtccag gatcaaattg gaataatgag    900
atacatggtc atactaatga aaccagcaat aacacgcaaa gaaatgccga gtgttttctt    960
gacttacctt ctgagtcttc cagtgagcct gacgcaaagc gcatggagct agtgcagaag   1020
aacaccgata gctttcactt ccagaaaact gtatatgatg ccgctgatat ggagttaact   1080
gctactgaca taggcaagat tgtagcagtt tcaaaaagca agaaaaatca aaataagaaa   1140
aaggcagact gtagaaagga gactttcaga aaagtgaaag gtgcaagctc tgataaaaag   1200
agagaaagct caaagagaga atgtaaagat ggttcagaag taggtgctga ggaagaggct   1260
gatgcagcca gagcagaaag aggcgctggt gtcctggatg gcagagggga ttcagaagag   1320
ccaaactgca tttccagtac tgagcagcca tctcaggtaa acacgcaaaa gaaaagaacc   1380
ctccagaaca gctcagatca ggagaacatt caaaatacga agaggaggca aacatatacg   1440
acagatgagc aagaggaaac aaaccctttc tccagacatt cagtcaaatt tcttcaagat   1500
ggtaaatttg atctgtgtca gaaaacccta catcataatt taagtaagcc ttctcgacag   1560
acatttgtga ttcgtaagtc agaaaaagat aacttatttc caaatcaaga agataaagac   1620
accatttctg aaaacctaga agttacaaat gaatttcata tagatgatct ttccatcgaa   1680
gctaatgaaa atgtatgtga ccatgagact cagacaatgt tggacttgaa aaagtctgtc   1740
agtgctcaac aaaatcaaac aaaaataaat aagactaagc agaaaataaa tcgaaggaca   1800
aaaataattt ctgtcatgag ccaagtatat gaggacaatg ataaagatat tcacgtccta   1860
gaaaaagaca actttccctt tcatacccaa gcaaataaag aaaccaccag tggaaaccta   1920
gaaagttcaa aagaatttga atcacctctt cttttcacaa gagacaacgg aagcttacgt   1980
gactgtaaga cccagaatgt tctggatctg cacaagcaaa ttcctgatct ataccctgat   2040
cggaatgagt cccagattag caaaatccct aggcaaaaag taaatcgcaa gacagaagta   2100
atttctggag tgaaatgttt tagtaatgac caaggtgttc attgctcaga aaaggataag   2160
tctttgttac tacaaaagga taaagacttc ccaggaactt taaaagactt aagtgagttt   2220
gatacgcctg ctttttgtaa caaagatagt gcaaagtcgt gtgattataa gtctgaaatg   2280
ctcttggggt tgaaaaaaca tgaccctaat atgcaacctg cttgtcaaga tgattcaaaa   2340
gcaggtaaga aacttagaca aaaggtaaat cgaaaaacag aaataatttc taaaatcacc   2400
caaatacatg aaaatgatag aggaagtaca catgactcat taaataagaa gctctgtcag   2460
aaggttaata tatcaaaaat catttctcaa atgaaccaaa tatatgagac tattaatgaa   2520
gatggaaatg gctttaaaag ctctatcaaa gattgcgaag atattaaaag ttgtgacttt   2580
ggggaaatca acagtaataa aaaggaaaat tatgatccaa ttcaagatcc ttgcacactg   2640
gttaaaaaaa caaagagaaa gggatcatgt aaagcaggga gcagtttggc aggagctaag   2700
aacaggtgtg gtttgcagtt aacagactct tcccaggtac agtctgtccc cttagactct   2760
ggcttaagac accatccaaa cgaagcagat tctggtcctg gagagcagac taacctgcca   2820
aagatgcaga aacaaagcgc tgggaggtca ctgggagatg ctttctctgt gagtctggga   2880
aaagaaggaa gccgcccagc caaagcagtt agtaaaatga cacccaaatc aaagaagaga   2940
```

```
aagctccctc tcggttgttc tcctgaaacc cacgggacgg tggagataac acccaacact   3000

gacctcgcta aggctgttga ctcccaacag actgagaagg agaactattt ggagaaggag   3060

aaaattgcca agaggaagcc agatttttgt acaaaggtgt tgaaaccttt atctgagaca   3120

tgttcatcta acataaagaa ttcttccttg gacagtatgt gtaagagttc gctacctttg   3180

agtatttctt ctagaaaaac cctgatgctg gaagaaagtt cttccctgga gagtacatgc   3240

atctttcaag taggtgatgc cgctcatgag aagataacga caggcacacg taatccccac   3300

cacaggacac agaagtcgac accgggtagc agaacgtccc tggtcttggt ggataccagt   3360

tctgtttcag ataccaaccc tgctaacccc gagaatgagt cagaagggca gtcttcacac   3420

ccaatgagaa ggaaaagaca gtgcgtccct ctcaacctga cagagccaag ccttagaagc   3480

aagatgagga gataa                                                    3495
```

```
<210> SEQ ID NO 16
<211> LENGTH: 1164
<212> TYPE: PRT
<213> ORGANISM: mouse

<400> SEQUENCE: 16

Met Glu Tyr Pro Gly Ile Lys Val Asp Thr Val Thr Ser Gly Ile Gln
1               5                   10                  15

Arg Arg Val Lys Gly Arg Ile Ala Lys Thr Asn Leu Asn Val Ser Leu
            20                  25                  30

Ala Ser Lys Ile Lys Ala Lys Ile Leu Asn Asn Ser Ser Ile Phe Lys
        35                  40                  45

Ile Ser Leu Lys His Asn Asn Arg Ala Leu Ala Arg Ala Leu Ser Lys
    50                  55                  60

Glu Lys Glu Asn Ser Arg Arg Ile Thr Thr Glu Lys Met Gln Leu Gln
65                  70                  75                  80

Lys Glu Val Glu Lys Leu Asn Phe Glu Asn Thr Phe Leu Arg Leu Lys
                85                  90                  95

Leu Asn Thr Leu Asn Lys Lys Leu Val Glu Ile Glu Ser His Val Ser
            100                 105                 110

Asn Asp Leu Leu Thr Ala Ile Glu Ile Ser Ser Leu Ser Glu Phe His
        115                 120                 125

Gln Gly Ser Phe Leu Leu Ser Ala Thr Lys Lys Gln Arg Asn Ser Lys
    130                 135                 140

Gln Cys Lys Pro Ala His Leu Pro Tyr Ala Arg Val Leu Leu Thr Ser
145                 150                 155                 160

Glu Asn Asp Asp Asp Asp Gly Ala Asp Asp Lys Trp Gln Thr Lys Cys
                165                 170                 175

Asn Asn Arg Thr Ile Ser Lys Thr Ser Pro Asp Ser Thr Ser Ser Val
            180                 185                 190

Ser Arg Gln Pro Ser Ser Leu His Gln Cys Asn Leu Lys Ala Phe Pro
        195                 200                 205

Pro Lys Glu Asp Asn Gln Lys Thr Cys Gly Ser Gly His Leu Glu His
    210                 215                 220

Thr Ser Ser Val Asp Ile Leu Pro Asn Glu Ser His Ser Asp Gln Ser
225                 230                 235                 240

Pro Lys Ser Ser Leu Ser Glu Met Lys Thr Ala Pro Ser Pro Ser Leu
                245                 250                 255

Arg Arg Glu Lys Leu Ser His Gly Asn Val Thr Met Arg Lys Lys Cys
            260                 265                 270

Val Ser Ser Thr Pro Asp Ile Leu Tyr Val Thr Asp Leu Asp His Gln
```

```
        275                 280                 285

Pro Thr Ser Ser Pro Gly Ser Asn Trp Asn Asn Glu Ile His Gly His
    290                 295                 300

Thr Asn Glu Thr Ser Asn Asn Thr Gln Arg Asn Ala Glu Cys Phe Leu
305                 310                 315                 320

Asp Leu Pro Ser Glu Ser Ser Ser Glu Pro Asp Ala Lys Arg Met Glu
                325                 330                 335

Leu Val Gln Lys Asn Thr Asp Ser Phe His Phe Gln Lys Thr Val Tyr
            340                 345                 350

Asp Ala Ala Asp Met Glu Leu Thr Ala Thr Asp Ile Gly Lys Ile Val
        355                 360                 365

Ala Val Ser Lys Ser Lys Lys Asn Gln Asn Lys Lys Lys Ala Asp Cys
    370                 375                 380

Arg Lys Glu Thr Phe Arg Lys Val Lys Gly Ala Ser Ser Asp Lys Lys
385                 390                 395                 400

Arg Glu Ser Ser Lys Arg Glu Cys Lys Asp Gly Ser Glu Val Gly Ala
                405                 410                 415

Glu Glu Glu Ala Asp Ala Ala Arg Ala Glu Arg Gly Ala Gly Val Leu
            420                 425                 430

Asp Gly Arg Gly Asp Ser Glu Glu Pro Asn Cys Ile Ser Ser Thr Glu
        435                 440                 445

Gln Pro Ser Gln Val Asn Thr Gln Lys Lys Arg Thr Leu Gln Asn Ser
    450                 455                 460

Ser Asp Gln Glu Asn Ile Gln Asn Thr Lys Arg Arg Gln Thr Tyr Thr
465                 470                 475                 480

Thr Asp Glu Gln Glu Glu Thr Asn Pro Phe Ser Arg His Ser Val Lys
                485                 490                 495

Phe Leu Gln Asp Gly Lys Phe Asp Leu Cys Gln Lys Thr Leu His His
            500                 505                 510

Asn Leu Ser Lys Pro Ser Arg Gln Thr Phe Val Ile Arg Lys Ser Glu
        515                 520                 525

Lys Asp Asn Leu Phe Pro Asn Gln Glu Asp Lys Asp Thr Ile Ser Glu
    530                 535                 540

Asn Leu Glu Val Thr Asn Glu Phe His Ile Asp Asp Leu Ser Ile Glu
545                 550                 555                 560

Ala Asn Glu Asn Val Cys Asp His Glu Thr Gln Thr Met Leu Asp Leu
                565                 570                 575

Lys Lys Ser Val Ser Ala Gln Gln Asn Gln Thr Lys Ile Asn Lys Thr
            580                 585                 590

Lys Gln Lys Ile Asn Arg Arg Thr Lys Ile Ile Ser Val Met Ser Gln
        595                 600                 605

Val Tyr Glu Asp Asn Asp Lys Asp Ile His Val Leu Glu Lys Asp Asn
    610                 615                 620

Phe Pro Phe His Thr Gln Ala Asn Lys Glu Thr Thr Ser Gly Asn Leu
625                 630                 635                 640

Glu Ser Ser Lys Glu Phe Glu Ser Pro Leu Leu Phe Thr Arg Asp Asn
                645                 650                 655

Gly Ser Leu Arg Asp Cys Lys Thr Gln Asn Val Leu Asp Leu His Lys
            660                 665                 670

Gln Ile Pro Asp Leu Tyr Pro Asp Arg Asn Glu Ser Gln Ile Ser Lys
        675                 680                 685

Ile Pro Arg Gln Lys Val Asn Arg Lys Thr Glu Val Ile Ser Gly Val
    690                 695                 700
```

```
Lys Cys Phe Ser Asn Asp Gln Gly Val His Cys Ser Glu Lys Asp Lys
705                 710                 715                 720

Ser Leu Leu Leu Gln Lys Asp Lys Asp Phe Pro Gly Thr Leu Lys Asp
                725                 730                 735

Leu Ser Glu Phe Asp Thr Pro Ala Phe Cys Asn Lys Asp Ser Ala Lys
            740                 745                 750

Ser Cys Asp Tyr Lys Ser Glu Met Leu Leu Gly Leu Lys Lys His Asp
        755                 760                 765

Pro Asn Met Gln Pro Ala Cys Gln Asp Asp Ser Lys Ala Gly Lys Lys
    770                 775                 780

Leu Arg Gln Lys Val Asn Arg Lys Thr Glu Ile Ile Ser Lys Ile Thr
785                 790                 795                 800

Gln Ile His Glu Asn Asp Arg Gly Ser Thr His Asp Ser Leu Asn Lys
                805                 810                 815

Lys Leu Cys Gln Lys Val Asn Ile Ser Lys Ile Ile Ser Gln Met Asn
            820                 825                 830

Gln Ile Tyr Glu Thr Ile Asn Glu Asp Gly Asn Gly Phe Lys Ser Ser
        835                 840                 845

Ile Lys Asp Cys Glu Asp Ile Lys Ser Cys Asp Phe Gly Glu Ile Asn
    850                 855                 860

Ser Asn Lys Lys Glu Asn Tyr Asp Pro Ile Gln Asp Pro Cys Thr Leu
865                 870                 875                 880

Val Lys Lys Thr Lys Arg Lys Gly Ser Cys Lys Ala Gly Ser Ser Leu
                885                 890                 895

Ala Gly Ala Lys Asn Arg Cys Gly Leu Gln Leu Thr Asp Ser Ser Gln
            900                 905                 910

Val Gln Ser Val Pro Leu Asp Ser Gly Leu Arg His His Pro Asn Glu
        915                 920                 925

Ala Asp Ser Gly Pro Gly Glu Gln Thr Asn Leu Pro Lys Met Gln Lys
    930                 935                 940

Gln Ser Ala Gly Arg Ser Leu Gly Asp Ala Phe Ser Val Ser Leu Gly
945                 950                 955                 960

Lys Glu Gly Ser Arg Pro Ala Lys Ala Val Ser Lys Met Thr Pro Lys
                965                 970                 975

Ser Lys Lys Arg Lys Leu Pro Leu Gly Cys Ser Pro Glu Thr His Gly
            980                 985                 990

Thr Val Glu Ile Thr Pro Asn Thr  Asp Leu Ala Lys Ala  Val Asp Ser
        995                 1000                1005

Gln Gln  Thr Glu Lys Glu Asn  Tyr Leu Glu Lys Glu  Lys Ile Ala
    1010                1015                1020

Lys Arg  Lys Pro Asp Phe Cys  Thr Lys Val Leu Lys  Pro Leu Ser
    1025                1030                1035

Glu Thr  Cys Ser Ser Asn Ile  Lys Asn Ser Ser Leu  Asp Ser Met
    1040                1045                1050

Cys Lys  Ser Ser Leu Pro Leu  Ser Ile Ser Ser Arg  Lys Thr Leu
    1055                1060                1065

Met Leu  Glu Glu Ser Ser Ser  Leu Glu Ser Thr Cys  Ile Phe Gln
    1070                1075                1080

Val Gly  Asp Ala Ala His Glu  Lys Ile Thr Thr Gly  Thr Arg Asn
    1085                1090                1095

Pro His  His Arg Thr Gln Lys  Ser Thr Pro Gly Ser  Arg Thr Ser
    1100                1105                1110

Leu Val  Leu Val Asp Thr Ser  Ser Val Ser Asp Thr  Asn Pro Ala
    1115                1120                1125
```

-continued

```
Asn Pro  Glu Asn Glu Ser Glu  Gly Gln Ser Ser His  Pro Met Arg
    1130                 1135                 1140

Arg Lys  Arg Gln Cys Val Pro  Leu Asn Leu Thr Glu  Pro Ser Leu
    1145                 1150                 1155

Arg Ser  Lys Met Arg Arg
    1160


<210> SEQ ID NO 17
<211> LENGTH: 1584
<212> TYPE: DNA
<213> ORGANISM: Homo sapiens

<400> SEQUENCE: 17

atggccaagg aaagatgcct gaaaaagtcc tttcaagata gtcttgaaga cataaagaag     60

cgaatgaaag agaaaaggaa taaaaacttg gcagagattg gcaaacgcag gtcttttata    120

gctgcaccat gccaaataat caccaacact tctacactgc tgaaaaatta ccaagacaac    180

aacaaaatgt tagttttagc tttggaaaat gaaaaatcca aagtgaaaga agcccaagat    240

atcatcctac agctgagaaa agaatgttac tatctcacat gtcagctata tgcattgaaa    300

ggaaaactta catcacaaca aacagtagaa cctgctcaga accaggaaat atgttcctct    360

ggaatggacc ccaatagtga tgacagctcc agaaatttat ttgtgaagga tttaccgcaa    420

attcctcttg aagaaactga acttccagga caaggagaat catttcaaat agaagatcag    480

atacctacta ttcctcaaga cacactggga gttgattttg attcaggtga agctaagtct    540

actgataatg tcttacctag aactgtatct gttcgtagca gtttaaagaa acattgtaac    600

agtatatgtc agtttgatag cttggatgat tttgaaacca gtcatttggc agggaagtct    660

tttgaattcg aaagagttgg atttttagac ccactagtaa acatgcacat acctgaaaat    720

gtacaacaca atgcttgtca atggagcaag gaccaagtta acttatcacc aaagctgatt    780

cagccaggaa cgtttactaa aacaaaagaa gacattttag aatctaaatc tgaacaaact    840

aaaagtaagc aaagagatac acaagaaaga aaaagagaag agaaaagaaa agctaacagg    900

agaaaatcaa aacgtatgtc aaaatataaa gagaataaaa gcgaaaataa aaaaactgtt    960

ccccaaaaaa aaatgcacaa atctgtcagt tccaatgatg cttacaattt taatttggaa   1020

gagggtgttc atcttactcc tttccgacaa aaagtgagca atgactctaa tagagaagaa   1080

aacaacgagt ctgaagtgag cctctgtgaa tcaagtggtt caggagatga ttccgatgac   1140

ctctatttgc ccacttgcaa gtacattcag aatcccacga gcaattcaga tagaccagtc   1200

accaggcctc tagctaaaag agcactgaaa tacacagatg aaaaagagac ggagggttct   1260

aagccaacaa aaactcctac cactacacca cctgaaactc agcagtcacc tcatcttagc   1320

ctgaaggata tcaccaatgt ctccttgtat cctgttgtga aaatcagaag actttctctt   1380

tctccaaaaa agaataaagc aagcccagca gtggctctgc ctaaacgtag gtgcacagcc   1440

agcgtgaact ataaggagcc caccctcgct tcgaaactga gaagagggga cccttttaca   1500

gatttgtgtt ttttgaattc tcctattttc aagcagaaaa aggatttgag acgttctaaa   1560

aaaagtatga aacaaataca atga                                          1584


<210> SEQ ID NO 18
<211> LENGTH: 527
<212> TYPE: PRT
<213> ORGANISM: Homo sapiens

<400> SEQUENCE: 18
```

-continued

```
Met Ala Lys Glu Arg Cys Leu Lys Lys Ser Phe Gln Asp Ser Leu Glu
1               5                   10                  15

Asp Ile Lys Lys Arg Met Lys Glu Lys Arg Asn Lys Asn Leu Ala Glu
            20                  25                  30

Ile Gly Lys Arg Arg Ser Phe Ile Ala Ala Pro Cys Gln Ile Ile Thr
        35                  40                  45

Asn Thr Ser Thr Leu Leu Lys Asn Tyr Gln Asp Asn Asn Lys Met Leu
    50                  55                  60

Val Leu Ala Leu Glu Asn Glu Lys Ser Lys Val Lys Glu Ala Gln Asp
65                  70                  75                  80

Ile Ile Leu Gln Leu Arg Lys Glu Cys Tyr Tyr Leu Thr Cys Gln Leu
                85                  90                  95

Tyr Ala Leu Lys Gly Lys Leu Thr Ser Gln Gln Thr Val Glu Pro Ala
            100                 105                 110

Gln Asn Gln Glu Ile Cys Ser Ser Gly Met Asp Pro Asn Ser Asp Asp
        115                 120                 125

Ser Ser Arg Asn Leu Phe Val Lys Asp Leu Pro Gln Ile Pro Leu Glu
    130                 135                 140

Glu Thr Glu Leu Pro Gly Gln Gly Glu Ser Phe Gln Ile Glu Asp Gln
145                 150                 155                 160

Ile Pro Thr Ile Pro Gln Asp Thr Leu Gly Val Asp Phe Asp Ser Gly
                165                 170                 175

Glu Ala Lys Ser Thr Asp Asn Val Leu Pro Arg Thr Val Ser Val Arg
            180                 185                 190

Ser Ser Leu Lys Lys His Cys Asn Ser Ile Cys Gln Phe Asp Ser Leu
        195                 200                 205

Asp Asp Phe Glu Thr Ser His Leu Ala Gly Lys Ser Phe Glu Phe Glu
    210                 215                 220

Arg Val Gly Phe Leu Asp Pro Leu Val Asn Met His Ile Pro Glu Asn
225                 230                 235                 240

Val Gln His Asn Ala Cys Gln Trp Ser Lys Asp Gln Val Asn Leu Ser
                245                 250                 255

Pro Lys Leu Ile Gln Pro Gly Thr Phe Thr Lys Thr Lys Glu Asp Ile
            260                 265                 270

Leu Glu Ser Lys Ser Glu Gln Thr Lys Ser Lys Gln Arg Asp Thr Gln
        275                 280                 285

Glu Arg Lys Arg Glu Glu Lys Arg Lys Ala Asn Arg Arg Lys Ser Lys
    290                 295                 300

Arg Met Ser Lys Tyr Lys Glu Asn Lys Ser Glu Asn Lys Lys Thr Val
305                 310                 315                 320

Pro Gln Lys Lys Met His Lys Ser Val Ser Ser Asn Asp Ala Tyr Asn
                325                 330                 335

Phe Asn Leu Glu Glu Gly Val His Leu Thr Pro Phe Arg Gln Lys Val
            340                 345                 350

Ser Asn Asp Ser Asn Arg Glu Glu Asn Asn Glu Ser Glu Val Ser Leu
        355                 360                 365

Cys Glu Ser Ser Gly Ser Gly Asp Asp Ser Asp Asp Leu Tyr Leu Pro
    370                 375                 380

Thr Cys Lys Tyr Ile Gln Asn Pro Thr Ser Asn Ser Asp Arg Pro Val
385                 390                 395                 400

Thr Arg Pro Leu Ala Lys Arg Ala Leu Lys Tyr Thr Asp Glu Lys Glu
                405                 410                 415

Thr Glu Gly Ser Lys Pro Thr Lys Thr Pro Thr Thr Thr Pro Pro Glu
            420                 425                 430
```

```
Thr Gln Gln Ser Pro His Leu Ser Leu Lys Asp Ile Thr Asn Val Ser
        435                 440                 445

Leu Tyr Pro Val Val Lys Ile Arg Arg Leu Ser Leu Ser Pro Lys Lys
    450                 455                 460

Asn Lys Ala Ser Pro Ala Val Ala Leu Pro Lys Arg Arg Cys Thr Ala
465                 470                 475                 480

Ser Val Asn Tyr Lys Glu Pro Thr Leu Ala Ser Lys Leu Arg Arg Gly
                485                 490                 495

Asp Pro Phe Thr Asp Leu Cys Phe Leu Asn Ser Pro Ile Phe Lys Gln
            500                 505                 510

Lys Lys Asp Leu Arg Arg Ser Lys Lys Ser Met Lys Gln Ile Gln
        515                 520                 525


<210> SEQ ID NO 19
<211> LENGTH: 3798
<212> TYPE: DNA
<213> ORGANISM: Homo sapiens

<400> SEQUENCE: 19

atggagtgcc cagtgatgga aactggctca ctttttacct caggaattaa gagacatttg      60

aaagacaaaa gaatttcaaa gactactaag ttgaatgttt ctcttgcttc aaaaataaaa     120

acaaaaatac taaataattc ttctattttc aaaatatctt taaagcacaa caacagggca     180

ttagctcagg ctcttagtag agaaaaagag aattctcgaa gaattacaac tgaaaagatg     240

ctattgcaaa aagaagtaga gaaactgaat tttgagaaca catttcttcg cctaaagcta     300

aataacttga ataagaagct tatagacata gaagctctca tgaacaataa cttgataact     360

gcaactgaaa tgagcagtct ttctgagttc catcagagtt cctttctact gtcagctagc     420

aagaagaaac gagttagtaa acagtgcaag ttgatgcgtc ttccatttgc aagggttcca     480

ttaacttcaa atgatgatga agatgaagat aaagagaaaa tgcagtgtga caacaatatt     540

aaatcaaaga cattacctga tattccctct tcaggatcaa caacacaacc tttatcaact     600

caggataatt cggaagtgtt atttcttaaa gaaaataatc aaaatgtata tggtttagat     660

gattcagaac atatttcttc tatagttgat gtacctccca gagaaagcca ttcccactca     720

gaccaaagtt ctaagacttc tctaatgagt gagatgagaa acgcccagtc tattggccgc     780

agatgggaga aaccatctcc tagtaatgtg actgaaagga agaagcgtgg gtcatcttgg     840

gaatcaaata atctttctgc agacactccc tgtgcaacag ttttagataa acaacacatt     900

tcaagtccag aattaaattg caataatgag ataaatggtc atactaatga aacaaatact     960

gaaatgcaaa gaaataaaca ggatcttcct ggcttatctt ctgagtctgc cagagaacct    1020

aatgcagagt gcatgaatca aattgaggat aatgatgact ttcaattgca gaaaactgtg    1080

tatgatgctg acatggattt aactgctagt gaagtcagca aaattgtcac agtctcaaca    1140

ggcattaaaa agaaaagtaa taaaaaaaca aatgaacatg gaatgaaaac tttcagaaaa    1200

gtgaaagatt ccagctctga aaaaaagaga gaaagatcaa agagacagtt taaaaatagt    1260

tcagatgtcg atattgggga aaagattgaa aacaggacag aaagatctga tgtcctggat    1320

ggcaaaaggg gtgcagaaga tcccggtttt attttcaata atgaacagct ggctcagatg    1380

aatgaacagc tggctcaggt gaatgaacta aagaaaatga cccttcaaac tggctttgaa    1440

caaggtgaca gagaaaatgt actgtgtaat aaaaaggaga aaagaataac aaatgagcaa    1500

gaggaaacat actctttatc ccaaagttca ggtaaatttc accaggagag taaatttgat    1560

aagggtcaga attccctaac ttgtaataaa agtaaagctt ctagacagac atttgtgatt    1620
```

-continued cacaaattag aaaaagataa cttactccca aaccaaaagg ataaagtaac catttatgaa 1680
aacctagacg tcacaaatga atttcacaca gccaatcttt ccaccaaaga taatggaaat 1740
ttatgtgatt atgggaccca caatatattg gatttgaaaa agtatgtcac tgatattcaa 1800
ccctcagagc aaaatgaatc aaacattaat aagcttagaa agaaagtaaa ccggaagaca 1860
gaaataattt ctggaatgaa ccacatgtat gaagataatg ataaagatgt ggtgcatggc 1920
ctaaaaaaag gtaatttttt tttcaaaacc caagaggata aagaacctat ctctgaaaac 1980
atagaagttt ccaaagagct tcaaatccca gctctttcta ctagagataa tgaaaatcaa 2040
tgtgactata ggacccagaa tgtgttgggt ttgcaaaagc agatcaccaa tatgtacccc 2100
gttcagcaaa atgaatcaaa agttaataag aagcttaggc agaaagtaaa tcggaagaca 2160
gaaataattt ctgaagtgaa tcatttagat aatgacaaaa gtatagaata cacagttaaa 2220
agtcactcac tctttttaac gcaaaaagat aaggaaataa tccccggaaa cctagaagac 2280
ccaagtgagt ttgaaacacc tgctctttct accaaagata gtggaaacct gtatgattct 2340
gagattcaaa atgttttggg ggtgaaacat ggccatgata tgcaacctgc ttgtcaaaat 2400
gattcaaaaa taggtaagaa gcctagacta aatgtatgtc aaaagtcaga aataattcct 2460
gaaaccaacc aaatatatga gaatgataac aaaggtgtac atgacctaga aaaagataac 2520
ttcttctctc taaccccaaa ggataaagaa acaatttctg aaaatctaca agtcacaaat 2580
gaatttcaaa cagttgatct tctcatcaaa gataatggaa atttatgtga ttatgacacc 2640
cagaatatat tggagttgaa aaagtatgtt actgatagga aatctgctga gcaaaatgaa 2700
tcaaaaataa ataagctcag gaataaagtg aattggaaga cagaaataat ttctgaaatg 2760
aaccagatat atgaggataa tgataaagat gcacatgtcc aagaaagcta tacaaaagat 2820
cttgatttta aagtaaataa atctaaacaa aaacttgaat gccaagacat tatcaataaa 2880
cactatatgg aagtcaacag taatgaaaag gaaagttgtg atcaaatttt agattcctac 2940
aaagtagtta aaaaacgtaa gaaagaatca tcatgcaagg caaagaacat tttgacaaaa 3000
gctaagaaca aacttgcttc acagttaaca gaatcttcac agacatctat ctccttagaa 3060
tctgatttaa aacatattac tagtgaagca gattctgatc caggaaaccc agttgaacta 3120
tgtaagactc agaagcaaag cactaccact ttgaataaaa aagatctccc ttttgtggaa 3180
gaaataaaag aaggagagtg tcaggttaaa aaggtaaata aaatgacatc taagtcaaag 3240
aaaaggaaga cctccataga tccttctcca gagagccatg aagtaatgga aagaatactt 3300
gacagcgttc agggaaagtc tactgtatct gaacaagctg ataaggaaaa caatttggag 3360
aatgagaaaa tggtcaaaaa taagccagac ttttacacaa aggcatttag atctttgtct 3420
gagatacatt cacctaacat acaagattct tcctttgaca gtgttcgtga aggtttagta 3480
cctttgagcg tttcttctgg taaaaatgtg ataataaaag aaaattttgc cttggagtgc 3540
tccccagcct ttcaagtaag tgatgatgag catgagaaga tgaacaagat gaaatttaaa 3600
gtcaaccgga gaacccaaaa atcaggaata ggtgatagac cattacagga cttgtcaaat 3660
accagttttg tttcaaataa cactgctgaa tctgaaaata agtcagaaga tctatcttca 3720
gaacggacaa gcagaagaag aaggtgtact cctttctatt ttaaagagcc aagcctcaga 3780
gacaagatga gaagatga 3798

<210> SEQ ID NO 20
<211> LENGTH: 1265
<212> TYPE: PRT
<213> ORGANISM: Homo sapiens

<400> SEQUENCE: 20

```
Met Glu Cys Pro Val Met Glu Thr Gly Ser Leu Phe Thr Ser Gly Ile
1               5                   10                  15

Lys Arg His Leu Lys Asp Lys Arg Ile Ser Lys Thr Thr Lys Leu Asn
            20                  25                  30

Val Ser Leu Ala Ser Lys Ile Lys Thr Lys Ile Leu Asn Asn Ser Ser
        35                  40                  45

Ile Phe Lys Ile Ser Leu Lys His Asn Asn Arg Ala Leu Ala Gln Ala
    50                  55                  60

Leu Ser Arg Glu Lys Glu Asn Ser Arg Arg Ile Thr Thr Glu Lys Met
65                  70                  75                  80

Leu Leu Gln Lys Glu Val Glu Lys Leu Asn Phe Glu Asn Thr Phe Leu
                85                  90                  95

Arg Leu Lys Leu Asn Asn Leu Asn Lys Lys Leu Ile Asp Ile Glu Ala
            100                 105                 110

Leu Met Asn Asn Asn Leu Ile Thr Ala Ile Glu Met Ser Ser Leu Ser
        115                 120                 125

Glu Phe His Gln Ser Ser Phe Leu Leu Ser Ala Ser Lys Lys Lys Arg
    130                 135                 140

Ile Ser Lys Gln Cys Lys Leu Met Arg Leu Pro Phe Ala Arg Val Pro
145                 150                 155                 160

Leu Thr Ser Asn Asp Asp Glu Asp Glu Asp Lys Glu Lys Met Gln Cys
                165                 170                 175

Asp Asn Asn Ile Lys Ser Lys Thr Leu Pro Asp Ile Pro Ser Ser Gly
            180                 185                 190

Arg Thr Thr Gln Pro Leu Ser Thr Gln Asp Asn Ser Gly Val Leu Phe
        195                 200                 205

Leu Lys Glu Asn Asn Gln His Val Tyr Gly Leu Asp Asp Ser Glu His
    210                 215                 220

Ile Ser Ser Ile Val Asp Val Pro Pro Arg Glu Ser His Ser His Ser
225                 230                 235                 240

Asp Gln Ser Ser Lys Thr Ser Leu Met Ser Glu Met Arg Asn Ala Gln
                245                 250                 255

Ser Ile Gly Arg Arg Trp Glu Lys Pro Ser Pro Ser Asn Val Thr Glu
            260                 265                 270

Arg Lys Lys Arg Gly Ser Ser Trp Glu Ser Asn Asn Leu Ser Ala Asp
        275                 280                 285

Thr Pro Cys Ala Thr Val Leu Asp Lys Gln His Ile Ser Ser Pro Glu
    290                 295                 300

Leu Asn Cys Asn Asn Glu Ile Asn Gly His Thr Asn Glu Thr Asn Thr
305                 310                 315                 320

Glu Met Gln Arg Asn Lys Gln Asp Leu Pro Gly Leu Ser Ser Glu Ser
                325                 330                 335

Ala Arg Glu Pro Asn Ala Glu Cys Met Asn Gln Ile Glu Asp Asn Asp
            340                 345                 350

Asp Phe Gln Leu Gln Lys Thr Val Tyr Asp Ala Asp Met Asp Leu Thr
        355                 360                 365

Ala Ser Glu Val Ser Lys Ile Val Thr Val Ser Thr Gly Ile Lys Lys
    370                 375                 380

Lys Ser Asn Lys Lys Thr Asn Glu His Gly Met Lys Thr Phe Arg Lys
385                 390                 395                 400

Val Lys Asp Ser Ser Ser Glu Lys Lys Arg Glu Arg Ser Lys Arg Gln
                405                 410                 415
```

```
Phe Lys Asn Ser Ser Asp Val Asp Ile Gly Glu Lys Ile Glu Asn Arg
            420                 425                 430

Thr Glu Arg Ser Asp Val Leu Asp Gly Lys Arg Gly Ala Glu Asp Pro
        435                 440                 445

Gly Leu Phe Phe Asn Asn Glu Gln Leu Ala Gln Met Asn Glu Gln Leu
    450                 455                 460

Ala Gln Val Asn Glu Leu Lys Lys Met Thr Leu Gln Thr Gly Phe Glu
465                 470                 475                 480

Gln Gly Asp Arg Glu Asn Val Leu Cys Asn Lys Lys Glu Lys Arg Val
                485                 490                 495

Thr Asn Glu Gln Glu Glu Thr Tyr Ser Leu Ser Gln Ser Ser Gly Lys
            500                 505                 510

Phe His Gln Glu Ser Lys Phe Asp Lys Gly Gln Asn Ser Leu Thr Cys
        515                 520                 525

Asn Lys Ser Lys Ala Ser Arg Gln Thr Phe Val Ile His Lys Leu Glu
    530                 535                 540

Lys Asp Asn Leu Leu Pro Asn Gln Lys Asp Lys Val Thr Ile Tyr Glu
545                 550                 555                 560

Asn Leu Asp Val Thr Asn Glu Phe His Thr Ala Asn Leu Ser Thr Lys
                565                 570                 575

Asp Asn Gly Asn Leu Cys Asp Tyr Gly Thr His Asn Ile Leu Asp Leu
            580                 585                 590

Lys Lys Tyr Val Thr Asp Ile Gln Pro Ser Glu Gln Asn Glu Ser Asn
        595                 600                 605

Ile Asn Lys Leu Arg Lys Lys Val Asn Arg Lys Thr Glu Ile Ile Ser
    610                 615                 620

Gly Met Asn His Met Tyr Glu Asp Asn Asp Lys Asp Val Val His Gly
625                 630                 635                 640

Leu Lys Lys Gly Asn Phe Phe Phe Lys Thr Gln Glu Asp Lys Glu Pro
                645                 650                 655

Ile Ser Glu Ser Ile Glu Val Ser Lys Glu Leu Gln Ile Pro Ala Leu
            660                 665                 670

Ser Thr Arg Asp Asn Glu Asn Gln Cys Asp Tyr Arg Thr Gln Asn Val
        675                 680                 685

Leu Gly Leu Gln Lys Gln Ile Thr Asn Met Tyr Pro Val Gln Gln Asn
    690                 695                 700

Glu Ser Lys Val Asn Lys Lys Leu Arg Gln Lys Val Asn Arg Lys Thr
705                 710                 715                 720

Glu Ile Ile Ser Glu Val Asn His Leu Asp Asn Asp Lys Ser Ile Glu
                725                 730                 735

Tyr Thr Val Lys Ser His Ser Leu Phe Leu Thr Gln Lys Asp Lys Glu
            740                 745                 750

Ile Ile Pro Gly Asn Leu Glu Asp Pro Ser Glu Phe Glu Thr Pro Ala
        755                 760                 765

Leu Ser Thr Lys Asp Ser Gly Asn Leu Tyr Asp Ser Glu Ile Gln Asn
    770                 775                 780

Val Leu Gly Val Lys His Gly His Asp Met Gln Pro Ala Cys Gln Asn
785                 790                 795                 800

Asp Ser Lys Ile Gly Lys Lys Pro Arg Leu Asn Val Cys Gln Lys Ser
                805                 810                 815

Glu Ile Ile Pro Glu Thr Asn Gln Ile Tyr Glu Asn Asp Asn Lys Gly
            820                 825                 830

Val His Asp Leu Glu Lys Asp Asn Phe Phe Ser Leu Thr Pro Lys Asp
```

```
        835                 840                 845

Lys Glu Thr Ile Ser Glu Asn Leu Gln Val Thr Asn Glu Phe Gln Thr
    850                 855                 860

Val Asp Leu Leu Ile Lys Asp Asn Gly Asn Leu Cys Asp Tyr Asp Thr
865                 870                 875                 880

Gln Asn Ile Leu Glu Leu Lys Lys Tyr Val Thr Asp Arg Lys Ser Ala
                885                 890                 895

Glu Gln Asn Glu Ser Lys Ile Asn Lys Leu Arg Asn Lys Val Asn Trp
            900                 905                 910

Lys Thr Glu Ile Ile Ser Glu Met Asn Gln Ile Tyr Glu Asp Asn Asp
        915                 920                 925

Lys Asp Ala His Val Gln Glu Ser Tyr Thr Lys Asp Leu Asp Phe Lys
    930                 935                 940

Val Asn Lys Ser Lys Gln Lys Leu Glu Cys Gln Asp Ile Ile Asn Lys
945                 950                 955                 960

His Tyr Met Glu Val Asn Ser Asn Glu Lys Glu Ser Cys Asp Gln Ile
                965                 970                 975

Leu Asp Ser Tyr Lys Val Val Lys Lys Arg Lys Lys Glu Ser Ser Cys
            980                 985                 990

Lys Ala Lys Asn Ile Leu Thr Lys  Ala Lys Asn Lys Leu  Ala Ser Gln
        995                 1000                1005

Leu Thr  Glu Ser Ser Gln Thr  Ser Ile Ser Leu Glu  Ser Asp Leu
    1010                 1015                 1020

Lys His  Ile Thr Ser Glu Ala  Asp Ser Asp Pro Gly  Asn Pro Val
    1025                 1030                 1035

Glu Leu  Cys Lys Thr Gln Lys  Gln Ser Thr Thr Thr  Leu Asn Lys
    1040                 1045                 1050

Lys Asp  Leu Pro Phe Val Glu  Glu Ile Lys Glu Gly  Glu Cys Gln
    1055                 1060                 1065

Val Lys  Lys Val Asn Lys Met  Thr Ser Lys Ser Lys  Lys Arg Lys
    1070                 1075                 1080

Thr Ser  Ile Asp Pro Ser Pro  Glu Ser His Glu Val  Met Glu Arg
    1085                 1090                 1095

Ile Leu  Asp Ser Val Gln Gly  Lys Ser Thr Val Ser  Glu Gln Ala
    1100                 1105                 1110

Asp Lys  Glu Asn Asn Leu Glu  Asn Glu Lys Met Val  Lys Asn Lys
    1115                 1120                 1125

Pro Asp  Phe Tyr Thr Lys Ala  Phe Arg Ser Leu Ser  Glu Ile His
    1130                 1135                 1140

Ser Pro  Asn Ile Gln Asp Ser  Ser Phe Asp Ser Val  Arg Glu Gly
    1145                 1150                 1155

Leu Val  Pro Leu Ser Val Ser  Ser Gly Lys Asn Val  Ile Ile Lys
    1160                 1165                 1170

Glu Asn  Phe Ala Leu Glu Cys  Ser Pro Ala Phe Gln  Val Ser Asp
    1175                 1180                 1185

Asp Glu  His Glu Lys Met Asn  Lys Met Lys Phe Lys  Val Asn Arg
    1190                 1195                 1200

Arg Thr  Gln Lys Ser Gly Ile  Gly Asp Arg Pro Leu  Gln Asp Leu
    1205                 1210                 1215

Ser Asn  Thr Ser Phe Val Ser  Asn Asn Thr Ala Glu  Ser Glu Asn
    1220                 1225                 1230

Lys Ser  Glu Asp Leu Ser Ser  Glu Arg Thr Ser Arg  Arg Arg Arg
    1235                 1240                 1245
```

```
Cys Thr  Pro Phe Tyr Phe Lys  Glu Pro Ser Leu Arg  Asp Lys Met
    1250                 1255                 1260

Arg Arg
    1265


<210> SEQ ID NO 21
<211> LENGTH: 45
<212> TYPE: PRT
<213> ORGANISM: yeast

<400> SEQUENCE: 21

Met Glu Ser Leu Lys Lys Lys Phe Leu Lys Gln Asn Arg Glu Ile Ile
1               5                   10                  15

Lys Ile Asn Thr Gln Leu Ser Ile Lys Ile Arg Glu Ser Glu Asn Glu
            20                  25                  30

Ile Gln Asp Leu Ile Gln Glu Asn Phe Thr Leu Lys Ser
        35                  40                  45


<210> SEQ ID NO 22
<211> LENGTH: 45
<212> TYPE: PRT
<213> ORGANISM: yeast

<400> SEQUENCE: 22

Val Glu Asp Leu Lys Lys Lys Gln Ile Arg Gln Tyr Lys Glu Ile Ile
1               5                   10                  15

Arg Ile Ser Lys Ala Gln Ser Ile Arg Ile Lys Glu Leu Gln Leu Glu
            20                  25                  30

Asn Glu Arg Leu Leu Ser Glu Asn Ile Asp Leu Arg Thr
        35                  40                  45


<210> SEQ ID NO 23
<211> LENGTH: 45
<212> TYPE: PRT
<213> ORGANISM: yeast

<400> SEQUENCE: 23

Val Glu Asn Ile Arg Gln Ser Tyr Ser Arg Gln Asn Ser Leu Leu Ala
1               5                   10                  15

Lys Asp Asn Ser Ile Leu Lys Ile Lys Val Asn Ser Leu Glu Lys Lys
            20                  25                  30

Ile Ser Gln Leu Val Gln Glu Asn Val Thr Leu Arg Ser
        35                  40                  45


<210> SEQ ID NO 24
<211> LENGTH: 45
<212> TYPE: PRT
<213> ORGANISM: Neurospora crassa

<400> SEQUENCE: 24

Leu Glu Leu Leu Arg Arg Lys Phe Leu Arg Gln Asn Arg Asp Ile Ala
1               5                   10                  15

Arg Val Asn Ser Thr Gln Ser Leu Arg Ile Arg Gly Leu Glu Asn Glu
            20                  25                  30

Cys Ala Arg Leu Leu Ser Glu Asn Leu Glu Leu Arg Gly
        35                  40                  45


<210> SEQ ID NO 25
<211> LENGTH: 45
<212> TYPE: PRT
<213> ORGANISM: Dactylicapnos macrocapnos
```

```
<400> SEQUENCE: 25

Gly Ser Lys Val Glu Gln Gln Tyr Lys Leu Leu Asn Ala Glu Leu Met
1               5                   10                  15

Asp Gln Val Gln Lys Gln Arg Leu Glu Ile Gly Glu Tyr Arg Lys Arg
            20                  25                  30

Val Ile Ser Leu Glu Arg Glu Ile Met Asp Ile Arg Glu
        35                  40                  45


<210> SEQ ID NO 26
<211> LENGTH: 27
<212> TYPE: PRT
<213> ORGANISM: yeast

<400> SEQUENCE: 26

Gly Arg Glu Lys Leu Arg Arg Ser Val Lys Val Ile Asn Tyr Ala Ile
1               5                   10                  15

Pro Ser Leu Arg Thr Lys Leu Arg Arg Asp Phe
            20                  25


<210> SEQ ID NO 27
<211> LENGTH: 27
<212> TYPE: PRT
<213> ORGANISM: yeast

<400> SEQUENCE: 27

Pro Asp Gly Arg Ser Arg Arg Glu Arg Lys Lys Val Asn Tyr Ala Leu
1               5                   10                  15

Pro Gly Leu Arg Thr Lys Leu Arg Arg Asn Phe
            20                  25


<210> SEQ ID NO 28
<211> LENGTH: 28
<212> TYPE: PRT
<213> ORGANISM: yeast

<400> SEQUENCE: 28

Ser Phe Thr Arg Thr Arg Arg Thr Arg Gly Lys Ala Val Asp Tyr Thr
1               5                   10                  15

Leu Pro Ser Leu Arg Ala Lys Met Arg Arg Pro Ser
            20                  25


<210> SEQ ID NO 29
<211> LENGTH: 28
<212> TYPE: PRT
<213> ORGANISM: Neurospora crassa

<400> SEQUENCE: 29

Glu Thr Ser Arg Pro Ser Arg Arg Ala Arg Ala Ala Ile Ser Tyr Thr
1               5                   10                  15

Glu Pro Asn Leu Arg Asp Lys Met Arg Arg Pro Thr
            20                  25


<210> SEQ ID NO 30
<211> LENGTH: 27
<212> TYPE: PRT
<213> ORGANISM: Dactylicapnos macrocapnos

<400> SEQUENCE: 30

Asn Ser Ala Arg Pro Ser Arg Ser Cys Arg Pro Thr Ser Leu Val Glu
1               5                   10                  15

Pro Ser Leu Lys Asn Lys Leu Arg Asn Gly Ser
            20                  25
```

```
<210> SEQ ID NO 31
<211> LENGTH: 28
<212> TYPE: PRT
<213> ORGANISM: Caenorhabditis elegans

<400> SEQUENCE: 31

Thr Val Arg Arg Gln Arg Ser Ala Lys Met Asn Ile Lys Ser Leu Lys
1               5                   10                  15

Glu Pro Ser Gly Lys Asp Lys Leu Arg Arg Pro Gly
            20                  25


<210> SEQ ID NO 32
<211> LENGTH: 29
<212> TYPE: PRT
<213> ORGANISM: Arabidopsis thaliana

<400> SEQUENCE: 32

Thr Val Gly Arg Pro Ser Arg Gln Ala Ala Glu Lys Ile Lys Ser Tyr
1               5                   10                  15

Lys Glu Pro Ser Leu Lys Glu Lys Met Arg Gly Gly Phe
            20                  25


<210> SEQ ID NO 33
<211> LENGTH: 29
<212> TYPE: PRT
<213> ORGANISM: Arabidopsis thaliana

<400> SEQUENCE: 33

Ser Val Gly Arg Pro Ser Arg His Ala Ala Glu Lys Val Gln Ser Tyr
1               5                   10                  15

Arg Glu Val Ser Leu Arg Val Lys Met Arg Arg Lys Cys
            20                  25


<210> SEQ ID NO 34
<211> LENGTH: 28
<212> TYPE: PRT
<213> ORGANISM: mouse

<400> SEQUENCE: 34

Ala Val Ala Leu Thr Lys Arg Arg Cys Ser Thr Ile Lys Ser Tyr Lys
1               5                   10                  15

Glu Pro Thr Leu Ala Ser Lys Leu Arg Arg Gly Asp
            20                  25


<210> SEQ ID NO 35
<211> LENGTH: 25
<212> TYPE: PRT
<213> ORGANISM: mouse

<400> SEQUENCE: 35

His Pro Met Arg Arg Lys Arg Gln Cys Val Pro Leu Asn Leu Thr Glu
1               5                   10                  15

Pro Ser Leu Arg Ser Lys Met Arg Arg
            20                  25


<210> SEQ ID NO 36
<211> LENGTH: 28
<212> TYPE: PRT
<213> ORGANISM: Homo sapiens

<400> SEQUENCE: 36

Ala Val Ala Leu Pro Lys Arg Arg Cys Thr Ala Ser Val Asn Tyr Lys
```

```
1               5                   10                  15

Glu Pro Thr Leu Ala Ser Lys Leu Arg Arg Gly Asp
            20                  25


<210> SEQ ID NO 37
<211> LENGTH: 26
<212> TYPE: PRT
<213> ORGANISM: Homo sapiens

<400> SEQUENCE: 37

Ser Glu Arg Thr Ser Arg Arg Arg Arg Cys Thr Pro Phe Tyr Phe Lys
1               5                   10                  15

Glu Pro Ser Leu Arg Asp Lys Met Arg Arg
            20                  25


<210> SEQ ID NO 38
<211> LENGTH: 21
<212> TYPE: DNA
<213> ORGANISM: Artificial Sequence
<220> FEATURE:
<223> OTHER INFORMATION: TriplEx

<400> SEQUENCE: 38

ctcgggaagc gcgccattgt g                                                21


<210> SEQ ID NO 39
<211> LENGTH: 22
<212> TYPE: DNA
<213> ORGANISM: Homo sapiens

<400> SEQUENCE: 39

cctggctgaa tcagctttgg tg                                               22


<210> SEQ ID NO 40
<211> LENGTH: 23
<212> TYPE: DNA
<213> ORGANISM: Artificial
<220> FEATURE:
<223> OTHER INFORMATION: hSgo1

<400> SEQUENCE: 40

aagucuacug auaaaugucuu att                                              23


<210> SEQ ID NO 41
<211> LENGTH: 23
<212> TYPE: DNA
<213> ORGANISM: Artificial Sequence
<220> FEATURE:
<223> OTHER INFORMATION: hSgo2

<400> SEQUENCE: 41

aagcacuacc acuuugaaua att                                              23


<210> SEQ ID NO 42
<211> LENGTH: 21
<212> TYPE: DNA
<213> ORGANISM: Artificial Sequence
<220> FEATURE:
<223> OTHER INFORMATION: hSgo1

<400> SEQUENCE: 42

gugagccucu gugaaucaat t                                                21


<210> SEQ ID NO 43
<211> LENGTH: 21
```

-continued

```
<212> TYPE: DNA
<213> ORGANISM: Artificial Sequence
<220> FEATURE:
<223> OTHER INFORMATION: hSgo2

<400> SEQUENCE: 43

gcucucauga acaauaacut t                                              21


<210> SEQ ID NO 44
<211> LENGTH: 21
<212> TYPE: DNA
<213> ORGANISM: Artificial Sequence
<220> FEATURE:
<223> OTHER INFORMATION: siRNA,Target1

<400> SEQUENCE: 44

gagugaucac gauuucuaat t                                              21


<210> SEQ ID NO 45
<211> LENGTH: 21
<212> TYPE: DNA
<213> ORGANISM: Artificial Sequence
<220> FEATURE:
<223> OTHER INFORMATION: siRNA,Target2

<400> SEQUENCE: 45

aacgggcauu ugaauaugaa a                                              21
```